US011730150B2

(12) United States Patent
Hunt et al.

(10) Patent No.: US 11,730,150 B2
(45) **Date of Patent: *Aug. 22, 2023**

(54) FIBRILLIN-1 MUTATIONS FOR MODELING NEONATAL PROGEROID SYNDROME WITH CONGENITAL LIPODYSTROPHY

(71) Applicant: Regeneron Pharmaceuticals, Inc., Tarrytown, NY (US)

(72) Inventors: Charleen Hunt, Dumont, NJ (US); Jason Mastaitis, Yorktown Heights, NY (US); Guochun Gong, Pleasantville, NY (US); Ka-Man Venus Lai, Seattle, WA (US); Jesper Gromada, Concord, MA (US); Aris N. Economides, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 803 days.

This patent is subject to a terminal disclaimer.

(21) Appl. No.: 16/717,597

(22) Filed: Dec. 17, 2019

(65) Prior Publication Data

US 2020/0107527 A1 Apr. 9, 2020

Related U.S. Application Data

(63) Continuation of application No. 15/663,410, filed on Jul. 28, 2017, now Pat. No. 10,548,302.

(60) Provisional application No. 62/368,924, filed on Jul. 29, 2016.

(51) Int. Cl.
*A01K 67/027* (2006.01)
*A61K 49/00* (2006.01)
*C07K 14/78* (2006.01)

(52) U.S. Cl.
CPC ...... *A01K 67/0275* (2013.01); *A61K 49/0008* (2013.01); *C07K 14/78* (2013.01); *A01K 2217/00* (2013.01); *A01K 2217/056* (2013.01); *A01K 2227/105* (2013.01); *A01K 2267/0306* (2013.01)

(58) Field of Classification Search
None
See application file for complete search history.

(56) References Cited

U.S. PATENT DOCUMENTS

| | | | |
|---|---|---|---|
| 5,942,435 | A | 8/1999 | Wheeler |
| 6,586,251 | B2 | 7/2003 | Economides et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 10,329,582 | B2 | 6/2019 | Lee et al. |
| 10,385,359 | B2 | 8/2019 | Lee et al. |
| 10,548,302 | B2 | 2/2020 | Hunt et al. |
| 2008/0078000 | A1 | 3/2008 | Poueymirou et al. |
| 2014/0178879 | A1 | 6/2014 | Economides et al. |
| 2014/0235933 | A1 | 8/2014 | Lee et al. |
| 2014/0310828 | A1 | 10/2014 | Lee et al. |
| 2015/0376628 | A1 | 12/2015 | Schoenherr et al. |
| 2015/0376651 | A1 | 12/2015 | Frendewey et al. |
| 2016/0145646 | A1 | 5/2016 | Frendewey et al. |
| 2018/0027782 | A1 | 2/2018 | Hunt et al. |

FOREIGN PATENT DOCUMENTS

| | | | |
|---|---|---|---|
| RU | 2425880 | C2 | 8/2011 |
| WO | WO 2004/063226 | A2 | 7/2004 |
| WO | WO 2014/130706 | A1 | 8/2014 |
| WO | WO 2014/172489 | A2 | 10/2014 |
| WO | WO 2015/084625 | A1 | 6/2015 |
| WO | WO 2015/088643 | A1 | 6/2015 |
| WO | WO 2015/200334 | A1 | 12/2015 |
| WO | WO 2015/200805 | A2 | 12/2015 |
| WO | WO 2016/081923 | A2 | 5/2016 |
| WO | WO 2018/023014 | A1 | 2/2018 |

OTHER PUBLICATIONS

Graham (Genome Biology, 2014, vol. 16, No. 260, p. 1-21).*

Database UniProtKB/Swiss-Prot [online], Accession No. Q61554, <https://www.ncbi.nlm.nih.gov/protein/1042782301?sat=46&satkey=42898217> Jul. 6, 2016 uploaded, [retrieved on Jun. 24, 2020] Definition: RecName: Full=Fibrillin-1; Contains: RecName: Full=Asprosin; Flags: Precursor.

"The FBNI mutations database: The gene," [Retrieved from the Internet Jul. 28, 201 7: <URL: http://www.umd.be/FBN1/W_FBN1/gene.shtml>].

Biggin et al., "Detection of Thirty Novel FBN1 Mutations in Patients With Marfan Syndrome or a Related Fibrillinopathy," Hum. Mutat. 23(1):99, (2004).

Brevini, et al., "No shortcuts to pig embryonic stem cells," Theriogenology, 74(4):544-550, (2010).

Campens et al., "Intrinsic cardiomyopathy in Marfan syndrome: results from in-vivo and ex-vivo studies of the Fbn1C1039G/+ model and longitudinal findings in humans," Pediatric Research, 78(3):256-263, (2015).

Cao, et al., "Isolation and Culture of Primary Bovine Embryonic Stem Cell Colonies by a Novel Method," J. Exp. Zool. A. Ecol. Genet. Physiol., 311 (5):368-376, (2009).

Caputi et al., "A nonsense mutation in the fibrillin-1 gene of a Marfan syndrome patient induces NMD and disrupts an exonic splicing enhancer," Genes Dev. 16(14):1754-1759, (2002).

(Continued)

*Primary Examiner* — Michael C Wilson
(74) *Attorney, Agent, or Firm* — Alston & Bird LLP

(57) ABSTRACT

Provided are non-human animals comprising a mutation in the Fbn1 gene to model neonatal progeroid syndrome with congenital lipodystrophy (NPSCL). Also provided are methods of making such non-human animal models. The non-human animal models can be used for screening compounds for activity in inhibiting or reducing NPSCL or ameliorating NPSCL-like symptoms or screening compounds for activity potentially harmful in promoting or exacerbating NPSCL as well as to provide insights in to the mechanism of NPSCL and potentially new therapeutic and diagnostic targets.

20 Claims, 11 Drawing Sheets

Specification includes a Sequence Listing.

(56) References Cited

OTHER PUBLICATIONS

Carta et al., "Fibrillins 1 and 2 Perform Partially Overlapping Functions during Aortic Development," J. Biol. Chem. 281(12):8016-8023, (2006).
Carta et al., "p38 MAPK Is an Early Determinant of Promiscuous Smad2/3 Signaling in the Aortas of Fibrillin-1 (Fbnl)-null mice," The Journal of Biological Chemistry, 284(9):5630-5636, (2009).
Charbonneau et al. "In Vivo Studies of Mutant Fibrillin-1 Microfibrils," J. Biol. Chem. 285(32):2493-24955, (2010).
Chen, M., et al., "Truncated C-terminus of fibrillin-1 induces Marfanoid-progeroid-lipodystrophy (MPL) syndrome in rabbit," Disease Models and Mechanisms, 11 (4):dmm031542, (Apr. 9, 2018).
Chopra, "The Role of FBN1 in mammalian energy balance" [Retrieved from the Internet May 5, 2016 <URL: http://grantome.com/grant/NIH/K08-DK102529-01>].
Clark, et al., "A future for transgenic livestock," Nat. Rev. Genet., 4(10):825-833, (2003).
Cook et al., "Generation of Fbn1 conditional null mice implicate the extracellular microfibrils in osteoprogenitor recruitment," Genesis 50(8):635-641, (2012).
Davis et al., "Expression of FBN1 during adipogenesis: Relevance to the lipodystrophy phenotype in Marfan syndrome and related conditions," Molecular Genetics and Metabolism, 119:174-185, (2016).
Dietz et al., "Four Novel FBN1 Mutations: Significance for Mutant Transcript Level and EGF-like Domain Calcium Binding in the Pathogenesis of Marfan Syndrome," Genomics 17:468-475, (1993).
Duerrschmid, C., et al., "Asprosin is a centrally acting orexigenic hormone," Nature Medicine, 23(12):1444-1453, (2017).
Eadie et al., "Genetic Analysis of a Family with a Novel Type I Fibrillinopathy," J Aapos 18(2):134-139, (2014).
Fernandes et al., "Identification of Loci Modulating the Cardiovascular and Skeletal Phenotypes of Marfan Syndrome in Mice," Sci. Rep. 6:22426, (2016).
Ferruzzi et al., "Mechanical assessment of elastin integrity in fibrillin-1-deficient carotid arteries: implications for Marfan syndrome," Cardiovascular Research 92:287-295, (2011).
Garg et al., "De Novo Heterozygous FBN1 Mutations in the Extreme C-Terminal Region Cause Progeroid Fibrillinopathy," American Journal of Medical Genetics Part A, 164A:1341-1345, (2014).
Goldblatt et al., "Further Evidence fora Marfanoid Syndrome with Neonatal Progeroid Features and Severe Generalized Lipodystrophy Due to Frameshift Mutations Near the 3' End of the FBN1 Gene," Am. J. Med. Genet. A. 155A(4):717-720, (2011).
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Graul-Neumann et al., "Marfan Syndrome with Neonatal Progeroid Syndrome-Like Lipodystrophy Associated with Novel Frameshift Mutation at the 3' Terminus of the FBN1-Gene," Am. J. Med. Genet. A. 152A(11):2749-2755, (2010).
Halliday et al., "Twelve novel FBN1 mutations in Marfan syndrome and Marfan related phenotypes test the feasibility of FBN1 mutation testing in clinical practice," J. Med. Genet. 39(8):589-593, (2002).
Horn and Robinson, "Progeroid Facial Features and Lipodystrophy Associated with a Novel Splice Site Mutation in the Final Intron of the FBN1 Gene," Am. J. Med. Genet. A. 155A(4):721-724, (2011).
Hou et al., "Natural Course of Neonatal Progeroid Syndrome," Pediatr. Neonatol. 50(3):102-109, (2009).
Jacquinet et al., "Neonatal progeroid variant of Marfan syndrome with congenital lipodystrophy results from mutations at the 3' end of FBN1 gene," Eur. J. Med. Genet. 57(5):230-234, (2014).
Jean, et al., "Pluripotent genes in avian stem cells," Dev. Growth Differ., 55(1): 41-51, (2013).
Jensen et al., "C-terminal propeptide is required for fibrillin-1 secretion and blocks premature assembly through linkage to domains cbEGF41-43," Proc. Natl. Acad. Sci. U.S.A. 111(28):10155-10160, (2014).
Jensen et al., "Dissecting the Fibrillin Microfibril: Structural Insights into Organization and Function," Structure 20(2):215-225, (2012).
Judge et al., "Evidence for a critical contribution of haploinsufficiency in the complex pathogenesis of Marfan syndrome," J. Clin. Invest. 114(2):172-181, (2004).
Kainulainen et al., "Two mutations in Marfan syndrome resulting in truncated fibrillin polypeptides," Proc. Natl. Acad. Sci. U.S.A. 89:5917-5921, (1992).
Le Gloan et al., "Neonatal Marfan Syndrome: Report of a Case with an Inherited Splicing Mutation outside the Neonatal Domain," Mol. Syndromol. 6:281-286, (2015).
Lee et al., "Losartan Attenuates Degradation of Aorta and Lung Tissue Micromechanics in a Mouse Model of Severe Marfan Syndrome," Ann. Biomed. Eng. 44(10):2994-3006, (2016).
Lima et al., "A New Mouse Model for Marfan Syndrome Presents Phenotypic Variability Associated with the Genetic Background and Overall Levels of Fbnl Expression," PLoS One 5(11):e14136, (2010).
Loeys, "The search for genotype/phenotype correlation in Marfan syndrome: to be or not to be," Eur. Heart J. 37(43):3291-3293, (2016).
Mariko et al., "Fibrillin-1 genetic deficiency leads to pathological aging of arteries in mice," J. Pathol. 224(1):33-44, (2011).
Mizuguchi et al., "Recent progress in genetics of Marfan syndrome and Marfan-associated disorders," J. Hum. Genet., 52:1-12, (2007).
Munoz, et al., "Conventional pluripotency markers are unspecific for bovine embryonic-derived cell-lines," Theriogenology, 69(9): 1159-1164, (2008).
Neptune et al., "Dysregulation of TGF-β activation contributes to pathogenesis in Marfan syndrome," Nature Genetics, 33:407-411, (2003).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Paris, et al., "Equine embryos and embryonic stem cells: defining reliable markers of pluripotency," Theriogenology, 74(4): 516-524, (2010).
Passarge et al., "Marfanoid-progeroid-lipodystrophy syndrome: a newly recognized fibrillinopathy," European Journal of Human Genetics, 24:1244-1247, (2016).
Pereira et al., "Pathogenetic sequence for aneurysm revealed in mice underexpressing fibrillin-1," Proc. Natl. Acad. Sci. U.S.A. 96:3819-3823, (1999).
Pereira et al., "Targetting of the gene encoding fibrilin-1 recapitulates the vascular aspect of Marfan syndrome," Nat. Genet. 17(2):218-222, (1997).
Raghunath et al., "Analyses of truncated fibrillin caused by a 366 bp deletion in the FBN1 gene resulting in Marfan syndrome," Biochem. J. 302:889-896, (1994).
Regalado et al., "Pathogenic FBN1 Variants in Familial Thoracic Aortic Aneurysms and Dissections," Clin. Genet. 89(6):719-723, (2016).
Romere et al., "Asprosin, a Fasting-Induced Glucogenic Protein Hormone," Cell 165(3):566-579, (2016).
Saito et al., "Indication of Skin Fibrosis in Mice Expressing a Mutated Fibrillin-1 Gene," Molecular Medicine, 6(10):825-836, (2000).
Sakai et al., "FBN1: The disease-causing gene for Marfan syndrome and other genetic disorders," Gene, 591:279-291, (2016).
Schrijver et al., "Premature Termination Mutations in FBN1: Distinct Effects on Differential Allelic Expression and on Protein and Clinical Phenotypes," Am. J. Hum. Genet. 71:223-237, (2002).
Siracusa et al., "A Tandem Duplication within the fibrillin 1 Gene Is Associated with the Mouse Tight skin Mutation," Genome Res. 6(4):300-313, (1996).
Stheneur et al., "Prognosis Factors in Probands With an FBN1 Mutation Diagnosed Before the Age of 1 Year," Pediatr. Res. 69(3):265-270, (2011).
Tae et al., "Cardiac remodeling in the mouse model of Marfan syndrome develops into two distinctive phenotypes," Am. J. Physiol. Heart Circ. Physiol., 310:H290-H299, (2016).

(56) References Cited

OTHER PUBLICATIONS

Takenouchi et al., "Severe Congenital Lipodystrophy and a Progeroid Appearance: Mutation in the Penultimate Exon of FBN1 Causing a Recognizable Phenotype," Am. J. Med. Genet. A. 161A(12):3057-3062, (2013).
Tjeldhorn et al., "Qualitative and quantitative analysis of FBN1 mRNA from 16 patients with Marfan Syndrome," BMC Medical Genetics: 16:113, (2015).
Umeyama et al., "Generation of heterozygous fibrillin-1 mutant cloned pigs from genome-edited foetal fibroblasts," Sci. Rep. 6:24413, (2016).
Umeyama et al., "Supplementary Information: Generation of heterozygous fibrillin-1 mutant cloned pigs from genome-edited foetal fibroblasts," Apr. 14, 2016. [Retrieved from the Internet Nov. 8, 2017: <https://www.ncbi.nlm.nih.gov/pmc/articles/PMC4830.
Wakchaure, et al., "Transgenic Animals: A Review on its Various Dimensions and Applications in Animal Biotechnology," International Journal of Emerging Technology and Advanced Engineering, 5(11):210-213, (2015).
Wang et al., "Postmortem diagnosis of Marfan syndrome in a case of sudden death due to aortic rupture: Detection of a novel FBN1 frameshift mutation," ForensicSci. Int. 261:e1-e4, (2016).
Xu et al., "Abnormal fibrillin-1 expression and chronic oxidative stress mediated endothelial mesenchymal transition in a murine model of systemic sclerosis," Am. J. Physiol. Cell. Physiol. 300:C550-C556, (2011).
Yang et al., "Human embryonic stem cells derived from abnormal blastocyst donated by Marfan syndrome patient," Stem Cell Research 15:640-642, (2015).
Zeyer et al., "Engineered mutations in fibrillin-1 leading to Marfan syndrome act at the protein, cellular and organismal levels," Mutation Research, 765:7-18, (2015).
PCT International Search Report and Written Opinion of the International Searching Authority for application PCT/US2017/044409 dated Oct. 13, 2017.
U.S. Appl. No. 15/663,410, Non-Final Office Action dated May 31, 2019.
U.S. Appl. No. 15/663,410, Notice of Allowance and Interview Summary dated Sep. 19, 2019.
U.S. Appl. No. 15/663,410, Requirement for Restriction/Election dated Jan. 2, 2019.
Barthold, "Genetically altered mice: phenotypes, No. phenotypes, and Faux phenotypes," Genetica, 122(1):75-88, (2004).
Birling, et al., "Modeling human disease in rodents by CRISPR/Cas9 genome editing," Mamm. Genome, 28(7-8):291-301, (2017).
Brevini, et al., "Porcine embryonic stem cells: Facts, challenges and hopes," Theriogenology, 68 Suppl. 1:S206-S213, (2007).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," Ilar J., 43(2):100-109, (2002).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Harari, et al., "Bridging the Species Divide: Transgenic Mice Humanized for Type-I Interferon Response," PLoS ONE, 9(1):e84259, (2014).
Houdebine, "Methods to Generate Transgenic Animals," pp. 31-48 in "Genetic Engineering in Livestock: New Applications and Interdisciplinary Perspectives," Ed. Engelhard et al., (2009).
Kawamata, et al., "Generation of genetically modified rats from embryonic stem cells," Proc. Natl. Acad. Sci. U.S.A., 7(32):14223-14228, (2010).
Kumar, et al., "Transgenic Mouse Technology: Principles and Methods," Methods Mol. Biol., 590:335-362, (2009).
Mullins, et al., "Transgenesis in the rat and larger mammals," J. Clin. Invest. 97(7):1557-1560, (1996).
Poueymirou, et al., "F0 generation mice fully derived from gene-targeted embryonic stem cells allowing immediate phenotypic analyses," Nat. Biotechnol., 25(1):91-99, (2007).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321 (5897):1837-1841, (2008).
Sigmund, "Viewpoint: Are Studies in Genetically Altered Mice Out of Control?," Arterioscler. Thromb. Vasc. Biol., 20(6):1425-1429, (2000).
Valenzuela, et al., "High-throughput engineering of the mouse genome coupled with high-resolution expression analysis," Nat. Biotechnol., 21(6):652-659, (2003).
Zhou, et al., "Developing tTA transgenic rats for inducible and reversible gene expression," Int. J. Biol. Sci., 5(2):171-181, (2009).

* cited by examiner

| Fibrillin-1 Alleles | Sequence (Nucleotide Amino Acid) | SEQ ID NO |
|---|---|---|
| Human WT | ... CGG AGA AGC ACA AAC GAA ACT GAT ...<br>... R R / S T N E T D ... | 1<br>2 |
| Human Variant | ... CGG AGA AGC ACA AAC G**A**A AAC TGA<br>... R R / S T N E **N** * | 3<br>4 |
| Mouse WT | ... CGG AGA AGC ACG AAC GAA AC**G** GAT ...<br>... R R / S T N E T D ... | 5<br>6 |
| Engineered Mouse Variant MAID 8501 | ... CGG AGA AGC ACG AAC G**A**A AAC **T**GA<br>... R R / S T N E **N** * | 7<br>8 |

| Fibrillin-1 Alleles | Sequence (Nucleotide Amino Acid) | SEQ ID NO |
|---|---|---|
| Human WT | ...GAGTGT**AA**GATCAATGGCTACCCCAAACGGGGCAGGAAACGGAGAAGCACAAACGAAACT...<br>... E C K I N G Y P K R G R K R R / S T N E T ... | 9<br>10 |
| Human Variant | ...GAGTGT*GATCAATGGCTACCCCAAACGGGGCAGGAAACGGAGAAGCACAAACGAAACTGA*...<br>... E C D Q W L P Q T G Q E T E K H K R N * | 11<br>12 |
| Mouse WT | ...GAGTGT**AA**GATCAA**C**GGCTACCC**A**AAACG**A**GGC**C**GGAAACGGAGAAGCAC**G**AACGAAAC**G**...<br>... E C K I N G Y P K R G / R K R R / S T N E T ... | 13<br>14 |
| Engineered Mouse Variant MAID 8502 | ...GAGTGTGATCAA**T**GGCTACCC**C**AAACG**G**GGC**A**GGAAACGGAGAAGCAC**A**AACGAAAC**T**GA...<br>... E C D Q W L P Q T G Q E T E K H K R N * | 15<br>16 |
| MAID 8520 | PPASSEMDDN SLSPEACYEC KINGYPKAAQ SHLPATRPET EKHERNGCLR HPGRV | 17 |
| Expected MAID 8502 | PPASSEMDDN SLSPEACYEC DQWLPQTGQE TEKHKRN | 18 |

*FIG. 3*

SEQUENCE LISTING

```
<160> NUMBER OF SEQ ID NOS: 47

<210> SEQ ID NO 1
<211> LENGTH: 24
<212> TYPE: DNA
<213> ORGANISM: Homo sapiens

<400> SEQUENCE: 1

cggagaagca caaacgaaac tgat                                              24


<210> SEQ ID NO 2
<211> LENGTH: 8
<212> TYPE: PRT
<213> ORGANISM: Homo sapiens

<400> SEQUENCE: 2

Arg Arg Ser Thr Asn Glu Thr Asp
1               5


<210> SEQ ID NO 3
<211> LENGTH: 24
<212> TYPE: DNA
<213> ORGANISM: Homo sapiens

<400> SEQUENCE: 3

cggagaagca caaacgaaaa ctga                                              24


<210> SEQ ID NO 4
<211> LENGTH: 7
<212> TYPE: PRT
<213> ORGANISM: Homo sapiens

<400> SEQUENCE: 4

Arg Arg Ser Thr Asn Glu Asn
1               5
```

<210> SEQ ID NO 5
<211> LENGTH: 24
<212> TYPE: DNA
<213> ORGANISM: Mus musculus

<400> SEQUENCE: 5
cggagaagca cgaacgaaac ggat 24

<210> SEQ ID NO 6
<211> LENGTH: 8
<212> TYPE: PRT
<213> ORGANISM: Mus musculus

<400> SEQUENCE: 6

Arg Arg Ser Thr Asn Glu Thr Asp
1 5

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
cggagaagca cgaacgaaaa ctga 24

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Arg Arg Ser Thr Asn Glu Asn
1 5

<210> SEQ ID NO 9
<211> LENGTH: 60
<212> TYPE: DNA
<213> ORGANISM: Homo sapiens

<400> SEQUENCE: 9
gagtgtaaga tcaatggcta ccccaaacgg ggcaggaaac ggagaagcac aaacgaaact 60

<210> SEQ ID NO 10
<211> LENGTH: 20
<212> TYPE: PRT
<213> ORGANISM: Homo sapiens

<400> SEQUENCE: 10

Glu Cys Lys Ile Asn Gly Tyr Pro Lys Arg Gly Arg Lys Arg Arg Ser
1 5 10 15

Thr Asn Glu Thr
20

<210> SEQ ID NO 11
<211> LENGTH: 60
<212> TYPE: DNA
<213> ORGANISM: Homo sapiens

<400> SEQUENCE: 11
gagtgtgatc aatggctacc ccaaacgggg caggaaacgg agaagcacaa acgaaactga 60

<210> SEQ ID NO 12
<211> LENGTH: 19
<212> TYPE: PRT
<213> ORGANISM: Homo sapiens

<400> SEQUENCE: 12

Glu Cys Asp Gln Trp Leu Pro Gln Thr Gly Gln Glu Thr Glu Lys His
1 5 10 15

Lys Arg Asn

<210> SEQ ID NO 13
<211> LENGTH: 60
<212> TYPE: DNA
<213> ORGANISM: Mus musculus

<400> SEQUENCE: 13
gagtgtaaga tcaacggcta cccaaaacga ggccggaaac ggagaagcac gaacgaaacg 60

<210> SEQ ID NO 14
<211> LENGTH: 20
<212> TYPE: PRT
<213> ORGANISM: Mus musculus

<400> SEQUENCE: 14

Glu Cys Lys Ile Asn Gly Tyr Pro Lys Arg Gly Arg Lys Arg Arg Ser
1 5 10 15

Thr Asn Glu Thr
20

<210> SEQ ID NO 15
<211> LENGTH: 60
<212> TYPE: DNA
<213> ORGANISM: Artificial Sequence
<220> FEATURE:
<223> OTHER INFORMATION: Synthetic

<400> SEQUENCE: 15
gagtgtgatc aatggctacc ccaaacgggg caggaaacgg agaagcacaa acgaaactga 60

<210> SEQ ID NO 16
<211> LENGTH: 19
<212> TYPE: PRT
<213> ORGANISM: Artificial Sequence
<220> FEATURE:
<223> OTHER INFORMATION: Synthetic

<400> SEQUENCE: 16

Glu Cys Asp Gln Trp Leu Pro Gln Thr Gly Gln Glu Thr Glu Lys His
1 5 10 15

Lys Arg Asn

<210> SEQ ID NO 17
<211> LENGTH: 55
<212> TYPE: PRT
<213> ORGANISM: Artificial Sequence
<220> FEATURE:
<223> OTHER INFORMATION: Synthetic

<400> SEQUENCE: 17

Pro Pro Ala Ser Ser Glu Met Asp Asp Asn Ser Leu Ser Pro Glu Ala
1 5 10 15

-continued

```
Cys Tyr Glu Cys Lys Ile Asn Gly Tyr Pro Lys Ala Ala Gln Ser His
            20                  25                  30

Leu Pro Ala Thr Arg Pro Glu Thr Glu Lys His Glu Arg Asn Gly Cys
        35                  40                  45

Leu Arg His Pro Gly Arg Val
    50                  55


<210> SEQ ID NO 18
<211> LENGTH: 37
<212> TYPE: PRT
<213> ORGANISM: Artificial Sequence
<220> FEATURE:
<223> OTHER INFORMATION: Synthetic

<400> SEQUENCE: 18

Pro Pro Ala Ser Ser Glu Met Asp Asp Asn Ser Leu Ser Pro Glu Ala
1               5                   10                  15

Cys Tyr Glu Cys Asp Gln Trp Leu Pro Gln Thr Gly Gln Glu Thr Glu
            20                  25                  30

Lys His Lys Arg Asn
        35


<210> SEQ ID NO 19
<211> LENGTH: 8616
<212> TYPE: DNA
<213> ORGANISM: Homo sapiens

<400> SEQUENCE: 19

atgcgtcgag ggcgtctgct ggagatcgcc ctgggattta ccgtgctttt agcgtcctac     60

acgagccatg ggcggacgc caatttggag gctgggaacg tgaaggaaac cagagccagt    120

cgggccaaga gaagaggcgg tggaggacac gacgcgctta aaggacccaa tgtctgtgga    180

tcacgttata atgcttactg ttgccctgga tggaaaacct tacctggcgg aaatcagtgt    240

attgtcccca tttgccggca ttcctgtggg gatggatttt gttcgaggcc aaatatgtgc    300

acttgcccat ctggtcagat agctccttcc tgtggctcca gatccataca acactgcaat    360

attcgctgta tgaatggagg tagctgcagt gacgatcact gtctatgcca gaaaggatac    420

atagggactc actgtggaca acctgtttgt gaaagtggct gtctcaatgg aggaaggtgt    480

gtggccccaa atcgatgtgc atgcacttac ggatttactg gaccccagtg tgaaagagat    540

tacaggacag gcccatgttt tactgtgatc agcaaccaga tgtgccaggg acaactcagc    600

gggattgtct gcacaaaaac gctctgctgt gccacagtcg gccgagcctg gggccacccc    660

tgtgagatgt gtcctgccca gcctcacccc tgccgccgtg gcttcattcc aaatatccgc    720

acgggagctt gtcaagatgt ggatgaatgc caggccatcc ccgggctctg tcagggagga    780

aattgcatta atactgttgg gtcttttgag tgcaaatgcc ctgctggaca caaacttaat    840

gaagtgtcac aaaaatgtga agatattgat gaatgcagca ccattcctgg aatctgtgaa    900

gggggtgaat gtacaaacac agtcagcagt tacttttgca aatgtccccc tggtttttac    960

acctctccag atggtaccag atgcatagat gttcgcccag gatactgtta cacagctctg   1020

acaaacgggc gctgctctaa ccagctgcca cagtccataa ccaaaatgca gtgctgctgt   1080

gatgccggcc gatgctggtc tccaggggtc actgtcgccc ctgagatgtg tcccatcaga   1140

gcaaccgagg atttcaacaa gctgtgctct gttcctatgg taattcctgg gagaccagaa   1200

tatcctcccc cacccttgg ccccattcct ccagttctcc ctgttcctcc tggctttcct   1260

cctggacctc aaattccggt ccctcgacca ccagtggaat atctgtatcc atctcgggag   1320
```

-continued

```
ccaccaaggg tgctgccagt aaacgttact gattactgcc agttggtccg ctatctctgt   1380
caaaatggac gctgcattcc aactcctggg agttaccggt gtgagtgcaa caaagggttc   1440
cagctggacc tccgtgggga gtgtattgat gttgatgaat gtgagaaaaa cccctgtgct   1500
ggtggtgagt gtattaacaa ccagggttcg tacacctgtc agtgccgagc tggatatcag   1560
agcacactca cgcggacaga atgccgagac attgatgagt gtttacagaa tggccggatc   1620
tgcaataatg gacgctgcat caacacagat ggcagttttc attgcgtgtg taatgcgggc   1680
tttcatgtta cacgagatgg gaagaactgt gaagatatgg atgaatgcag cataaggaac   1740
atgtgcctta atggaatgtg tatcaatgaa gatggcagtt ttaaatgtat ttgcaaacct   1800
ggattccagc tggcatcaga tggacgttat tgcaaagaca ttaacgagtg tgaaacccct   1860
gggatctgca tgaatgggcg ttgcgtcaac actgatggct cctacagatg tgaatgcttc   1920
cctggactgg ctgtgggtct ggatggccgt gtgtgtgttg acacacacat gcggagcaca   1980
tgctatggtg gatacaagag aggccagtgt atcaaacctt tgtttggtgc tgtcactaaa   2040
tctgaatgct gttgcgccag cactgagtat gcatttgggg aaccttgcca gccgtgtcct   2100
gcacagaatt cagcggaata tcaggcactc tgcagcagtg ggccaggaat gacgtcagca   2160
ggcagtgata taaatgaatg tgcactagat cctgatattt gcccaaatgg aatctgtgaa   2220
aaccttcgtg ggacctataa atgtatatgc aattcaggat atgaagtgga ttcaactggg   2280
aaaaactgcg ttgatattaa tgaatgtgta ctgaacagtc tcctttgtga caatggacaa   2340
tgtagaaata ctcctggaag ttttgtctgt acctgcccca agggatttat ctacaaacct   2400
gatctaaaaa catgtgaaga cattgatgaa tgcgaatcaa gtccttgcat taatggagtc   2460
tgcaagaaca gcccaggctc ttttatttgt gaatgttctt ctgaaagtac tttggatcca   2520
acaaaaacca tctgcataga aaccatcaag ggcacttgct ggcagactgt cattgatggg   2580
cgatgtgaga tcaacatcaa tggagccacc ttaaagtccc agtgctgctc ctccctcggt   2640
gctgcgtggg gaagcccgtg caccctatgc caagttgatc ccatatgtgg taaagggtac   2700
tcaagaatta aaggaacaca atgtgaagat atagatgaat gtgaagtgtt cccaggagtg   2760
tgtaaaaatg gcctgtgtgt taacactagg gggtcattca agtgtcagtg tcccagtgga   2820
atgactttgg atgccacagg aaggatctgt cttgatatcc gcctggaaac ctgcttcctg   2880
aggtacgagg acgaggagtg caccctgcct attgctggcc gccaccgcat ggacgcctgc   2940
tgctgctccg tcggggcagc ctggggtact gaggaatgcg aggagtgtcc catgagaaat   3000
actcctgagt acgaggagct gtgtccgaga ggacccggat ttgccacaaa agaaattaca   3060
aatggaaagc ctttcttcaa agatatcaat gagtgcaaga tgatacccag cctctgcacc   3120
cacggcaagt gcagaaacac cattggcagc tttaagtgca ggtgtgacag cggctttgct   3180
cttgattctg aagaaaggaa ctgcacagac attgacgaat gccgcatatc tcctgacctc   3240
tgtggcagag gccagtgtgt gaacacccct ggggactttg aatgcaagtg tgacgaaggc   3300
tatgaaagtg gattcatgat gatgaagaac tgcatggata ttgatgagtg tcagagagat   3360
cctctcctat gccgaggtgg tgtttgccat aacacagagg gaagttaccg ctgtgaatgc   3420
ccgcctggcc atcagctgtc cccaacatc tccgcgtgta tcgacatcaa tgaatgtgag   3480
ctgagtgcac acctgtgccc caatggccgt tgcgtgaacc tcatagggaa gtatcagtgt   3540
gcctgcaacc ctggctacca ttcaactccc gataggctat tttgtgttga cattgatgaa   3600
tgcagcataa tgaatggtgg ttgtgaaacc ttctgcacaa actctgaagg cagctatgaa   3660
```

-continued

```
tgtagctgtc agccgggatt tgcactaatg cctgaccaga gatcatgcac cgacatcgat   3720
gagtgtgaag ataatcccaa tatctgtgat ggtggtcagt gcacaaatat ccctggagag   3780
tacaggtgct tgtgttatga tggattcatg gcatctgaag acatgaagac ttgtgtagat   3840
gtcaatgagt gtgacctgaa tccaaatatc tgcctaagtg ggacctgtga aaacacgaaa   3900
ggctcattta tctgccactg tgatatgggc tactccggca aaaaaggaaa aactggctgt   3960
acagacatca atgaatgtga aattggagca cacaactgtg gcaaacatgc tgtatgtacc   4020
aatacagcag gaagcttcaa atgtagctgc agtcccgggt ggattggaga tggcattaag   4080
tgcactgatc tggacgaatg ttccaatgga acccatatgt gcagccagca tgcagactgc   4140
aagaatacca tgggatctta ccgctgtctg tgcaaggaag gatacacagg tgatggcttc   4200
acttgtacag accttgatga gtgctctgag aacctgaatc tctgtggcaa tggccagtgc   4260
ctcaatgcac caggaggata ccgctgtgaa tgcgacatgg gcttcgtgcc cagtgctgac   4320
gggaaagcct gtgaagatat tgatgagtgc tcccttccga acatctgtgt ctttggaact   4380
tgccacaacc tccctggcct gttccgctgt gagtgtgaga taggctacga actggacaga   4440
agcggcggga actgcacaga tgtgaatgaa tgcctggatc caaccacgtg catcagtggg   4500
aactgtgtca acactccagg cagctatatc tgtgactgcc cacctgattt tgaactgaac   4560
ccaactcgag ttggctgtgt tgatacccgc tctggaaatt gctatttgga tattcgacct   4620
cgaggagaca atggagatac agcctgcagc aatgaaattg gagttggtgt ttccaaagct   4680
tcctgctgct gttctctggg taaagcctgg ggtactcctt gtgagatgtg tcctgctgtg   4740
aacacatccg agtacaaaat tctttgtcct ggaggggaag gtttccgacc aaatcctatc   4800
accgttatat tggaagatat tgatgagtgc caggagctac cagggctgtg ccaaggagga   4860
aaatgtatca acacctttgg gagtttccag tgccgctgtc caaccggcta ctacctgaat   4920
gaagatacac gagtgtgtga tgatgtgaat gaatgtgaga ctcctggaat ctgtggtcca   4980
gggacatgtt acaacaccgt tggcaactac acctgtatct gtcctccaga ctacatgcaa   5040
gtgaatgggg gaaataattg catggatatg agaagaagtt tgtgctacag aaactactat   5100
gctgacaacc agacctgtga tggagaattg ttattcaaca tgaccaagaa gatgtgctgc   5160
tgttcctaca acattggccg ggcgtggaac aagccctgtg aacagtgtcc catcccaagt   5220
acagatgagt ttgctacact ctgtggaagt caaaggccag gctttgtcat cgacatttat   5280
accggtttac ccgttgatat tgatgagtgc cgggagatcc caggggtctg tgaaaatgga   5340
gtgtgtatca acatggttgg cagcttccga tgtgaatgtc cagtgggatt cttctataat   5400
gacaagttgt tggtttgtga agatattgac gagtgtcaga acggcccagt gtgccagcgc   5460
aacgccgaat gcatcaacac tgcaggcagc taccgctgtg actgtaagcc cggctaccgc   5520
ttcacctcca caggacagtg caatgatcgt aatgaatgtc aagaaatccc caatatatgc   5580
agtcatgggc agtgcattga cacagttgga agcttttatt gcctttgcca cactggtttt   5640
aaaacaaatg atgaccaaac catgtgcttg gacataaatg aatgtgaaag agatgcctgt   5700
gggaatggaa cttgccggaa cacaattggt tccttcaact gccgctgcaa tcatggtttc   5760
atcctttctc acaacaatga ctgtatagat gttgatgaat gtgcaagtgg aaatgggaat   5820
ctttgcagaa atggccaatg cattaataca gtggggtctt tccagtgcca gtgcaatgaa   5880
ggctatgagg tggctccaga tgggaggacc tgtgtggata tcaatgaatg tcttctagaa   5940
cccagaaaat gtgcaccagg tacctgtcaa aacttggatg ggtcctacag atgcatttgc   6000
ccacctggat acagtcttca aaatgagaag tgtgaagata ttgatgagtg tgtcgaagag   6060
```

-continued

```
ccagaaattt gtgccctggg cacatgcagt aacactgaag gcagcttcaa atgtctgtgt   6120
ccagaagggt tttccttgtc ctccagtgga agaaggtgcc aagatttgcg aatgagctac   6180
tgttatgcga agtttgaagg aggaaagtgt tcatcaccca aatccagaaa tcactccaag   6240
caggaatgct gctgtgcctt gaagggagaa ggctggggag acccctgcga gctctgcccc   6300
acggaacctg atgaggcctt ccgccagata tgtccttatg gaagtgggat catcgtggga   6360
cctgatgatt cagcagttga tatggacgaa tgcaaagaac ccgatgtctg taaacatgga   6420
cagtgcatca atacagatgg ttcctatcgc tgcgagtgtc cctttggtta tattctagca   6480
gggaatgaat gtgtagatac tgatgaatgt tctgttggca atccttgtgg aaatggaacc   6540
tgcaagaatg tgattggagg ttttgaatgc acctgcgagg agggatttga gcccggtcca   6600
atgatgacat gtgaagatat aaatgaatgt gcccagaatc ctctgctctg tgccttccga   6660
tgtgtgaaca cttatgggtc atatgaatgc aaatgtcccg tgggatatgt gctcagagaa   6720
gaccgtagga tgtgcaaaga tgaggatgag tgtgaagagg gaaaacatga ctgtactgaa   6780
aaacaaatgg aatgcaagaa cctcattggc acatatatgt gcatctgtgg acccgggtat   6840
cagcggagac ctgatggaga aggctgtgta gatgagaatg aatgtcagac gaagccaggg   6900
atctgtgaga atgggcgctg cctcaacacc cgtgggagct acacctgtga gtgtaatgat   6960
gggtttaccg ccagccccaa ccaggacgag tgccttgaca atcgggaagg gtactgcttc   7020
acagaggtgc tacaaaacat gtgtcagatc ggctccagca acaggaaccc cgtcaccaaa   7080
tcggaatgct gctgtgacgg agggagaggc tggggtcccc actgtgagat ctgccctttc   7140
caggggactg tggctttcaa gaaactctgt ccccatggcc gaggattcat gaccaatgga   7200
gcagatatcg atgaatgcaa ggttattcac gatgtttgcc gaaatgggga atgtgtcaat   7260
gacagaggat catatcattg catttgtaaa actgggtaca ctccagatat aactgggact   7320
tcctgtgtag atctgaacga gtgcaaccag gctcccaaac cctgcaattt tatctgcaaa   7380
aacacagaag ggagttacca gtgttcatgc ccgaaaggct acattctgca agaggatgga   7440
aggagctgca aagatcttga tgagtgtgca accaagcaac acaactgcca gttcctatgt   7500
gttaacacca ttggcggctt cacatgcaaa tgtcctcccg gatttaccca acaccatacg   7560
tcctgcattg ataacaatga atgcacctct gacatcaatc tgtgcgggtc taagggcatt   7620
tgccagaaca ctcctggaag cttcacctgt gaatgccagc ggggattctc acttgatcag   7680
accggctcca gctgtgaaga cgtggacgag tgtgagggta accaccgctg ccagcatggc   7740
tgccagaaca tcattggggg ctacaggtgc agctgccccc agggctacct ccagcactac   7800
cagtggaacc agtgtgttga tgaaaacgaa tgcctcagcg ctcacatctg cggaggagcc   7860
tcctgtcaca acaccctggg gagctacaag tgcatgtgtc ccgccggctt ccagtatgaa   7920
cagttcagtg gaggatgcca agacatcaat gaatgtggct ctgcgcaggc cccctgcagc   7980
tatggctgtt ccaataccga gggcggttac ctgtgtggct gtccacctgg ttacttccgc   8040
ataggccaag ggcactgtgt ttctggaatg ggcatgggcc gaggaaaccc agagccacct   8100
gtcagtggtg aaatggatga caattcactc tccccagagg cttgttacga gtgtaagatc   8160
aatggctacc ccaaacgggg caggaaacgg agaagcacaa acgaaactga tgcctccaat   8220
atcgaggatc agtctgagac agaagccaat gtgagtcttg caagttggga tgttgagaag   8280
acagccatct ttgctttcaa tatttcccac gtcagtaaca aggttcgaat cctagaactc   8340
cttccagctc ttacaactct gacgaatcac aacagatact tgatcgaatc tggaaatgaa   8400
```

gatggcttct ttaaaatcaa ccaaaaggaa gggatcagct acctccactt cacaaagaag 8460
aagccagtgg ctggaaccta ttcattacaa atcagtagta ctccacttta taaaaagaaa 8520
gaacttaacc aactagaaga caaatatgac aaagactacc tcagtggtga actgggtgat 8580
aatctgaaga tgaaaatcca ggttttgctt cattaa 8616

<210> SEQ ID NO 20
<211> LENGTH: 8622
<212> TYPE: DNA
<213> ORGANISM: Mus musculus

<400> SEQUENCE: 20
atgcggcgag gagggctgct ggaggtcgcg ctggcgttcg ccctgctcct cgagtcctac 60
acgagccatg ggcggacgc caatttggag gctgggagcc tgaaggagac cagagccaat 120
cgggccaaga gaagaggcgg cggaggacac gatgcgctga aaggacccaa tgtctgtgga 180
tcacgttata atgcatactg ttgtcctgga tggaaaacct tacctggtgg aaatcagtgt 240
attgttccca tttgccggca ttcctgtggg gatggattct gctcgaggcc aaatatgtgc 300
acttgcccgt ctggtcagat atctccttcc tgtggctcca gatccatcca acactgcagc 360
atccgctgta tgaatggggg cagctgcagc gatgaccact gtctgtgcca gaaagggtac 420
atcggcactc actgtggaca gcctgtctgt gaaagtggct gtctcaacgg agggaggtgt 480
gtggccccaa atcggtgtgc ttgcacgtac ggctttactg gaccccagtg tgaaagagat 540
tacagaacag gcccatgttt tactgtggta agcaaccaga tgtgccaggg acagctcagc 600
gggattgtct gcaccaaaac actttgctgt gccaccgtgg gccgagcctg gggccacccc 660
tgtgagatgt gtcctgccca gcctcacccc tgccgccgcg gcttcattcc caacatccgc 720
actggagctt gtcaagatgt ggatgaatgt caggccatcc cagggatgtg tcaaggagga 780
aattgcatta ataccgttgg atcttttgag tgcaaatgcc ctgctggaca caaatttaat 840
gaagtgtcac aaaaatgtga agatattgac gagtgcagca ccattcctgg agtctgcgat 900
ggcggggaat gtacaaacac tgtcagcagc tacttctgca aatgtccccc tggtttttac 960
acctctcctg atggcaccag atgcgtagat gttcgccctg gttactgcta cacagctctg 1020
gcaaacgggc gctgctctaa ccagctgcca cagtccataa ccaaaatgca gtgctgttgc 1080
gatcttggcc ggtgctggtc tccaggggtt actgttgctc ccgagatgtg tcccatcagg 1140
tcaactgagg atttcaacaa gctgtgctct gtccctctgg taattcccgg gagaccagaa 1200
tatcctcccc cacccattgg cccccttcct ccagttcagc ccgttcctcc tggctatcct 1260
cctgggcctg tgattccagc ccctcggcca ccgccagaat atccatatcc atctccgtct 1320
cgggaaccac caagggtgct gcctttcaac gttactgact actgtcaact ggtccgctat 1380
ctctgtcaaa atgggcgctg cattccaact cccggtagct accgctgcga gtgcaacaag 1440
ggcttccagc tggatatccg tggcgaatgc atcgacgtgg atgagtgtga gaagaaccca 1500
tgcactggtg gcgagtgcat caacaaccag ggctcctaca cctgtcactg cagagctggc 1560
taccagagca cactcaccag aactgagtgc agagacatag atgagtgtct tcagaatggc 1620
cggatctgca acaatggtcg ctgtatcaac acagacggca gcttccactg cgtatgcaat 1680
gcgggctttc atgtcacgcg ggacggaaag aactgtgaag atatggatga gtgcagcatc 1740
cgaaacatgt gcctaaacgg aatgtgtatt aatgaagatg gcagtttcaa gtgtatttgc 1800
aaacctgggt tccaactggc atcagatggc cgctactgca aagatatcaa tgagtgtgag 1860
acacctggga tctgcatgaa cggacgctgt gtgaacacgg atggctccta cagatgcgaa 1920

-continued tgcttccccg gattggctgt gggtctagac ggacgtgtgt gtgttgacac acacatgcgg 1980
agcacatgct atggaggata caggagaggc cagtgcgtga agccgttgtt tggtgctgtt 2040
accaaatcgg aatgctgttg tgccagcact gagtatgcct ttggggaacc ctgccagccg 2100
tgtcctgcac agaattcagc ggaatatcag gcactctgca gcagtggacc gggaatgaca 2160
tcagcaggca ctgatataaa cgaatgtgca ttagatcctg atatttgccc aaatggaatt 2220
tgtgaaaatc tccgtgggac ctacaaatgt atatgcaact cgggatatga agtagacata 2280
actgggaaaa actgtgtcga tattaatgag tgtgtgctga acagtctact ttgtgacaat 2340
ggacaatgtc gaaacacacc tggaagtttt gtctgcacct gccccaaagg atttgtgtac 2400
aaacctgacc taaaaacctg tgaagacatt gatgaatgtg aatcgagtcc ttgcattaat 2460
ggagtctgca agaacagccc tggctccttc atttgtgaat gttctcctga aagtactctg 2520
gacccaacaa aaaccatctg catagaaacc atcaagggca cttgctggca gactgtcatc 2580
gacgggcgct gtgagatcaa catcaacgga gccaccttga agtccgagtg ctgctcctcc 2640
cttggtgctg cgtgggggag cccgtgcacc atctgtcaac ttgatcccat ttgtggtaaa 2700
gggttctcaa gaattaaagg cacgcaatgt gaagatatca atgagtgtga agtgttcccg 2760
ggagtatgca agaacggcct gtgtgtcaac tccaggggtt cattcaagtg cgagtgtccc 2820
aatggaatga ctttggatgc tacaggaaga atctgtcttg acatccgcct ggagacctgc 2880
ttcctcaagt atgacgatga agagtgcacc ttgcccatcg ctggccgcca ccgaatggat 2940
gcctgctgct gctctgttgg ggcagcctgg ggaacggaag agtgtgagga gtgtccattg 3000
agaaacagcc gggagtatga ggaactctgt ccccgaggac ctgggtttgc cacaaaagac 3060
attacaaatg ggaaaccttt cttcaaagat atcaatgagt gcaagatgat acccagcctc 3120
tgtacccacg gcaagtgcag gaacaccatt ggcagcttca agtgtaggtg tgacagtggc 3180
tttgctctgg attctgaaga gaggaactgt acagacattg atgagtgccg catatctcct 3240
gacctctgtg gccgaggcca gtgtgtgaac accccggggg actttgaatg caagtgtgat 3300
gaaggctatg aaagtggctt catgatgatg aagaactgca tggatattga tgaatgtcag 3360
agagatcctc tcctgtgtcg aggaggcatt tgccacaaca cagagggaag ctatcgctgc 3420
gaatgtcctc ctggtcacca attgtcccca aacatctctg catgcattga catcaacgag 3480
tgtgagctga gtgcgaatct ctgtccccat gggcgttgtg tgaacctcat agggaagtac 3540
cagtgtgcct gcaaccctgg ctaccacccc actcatgaca ggctcttctg tgtcgatatt 3600
gatgaatgca gcataatgaa cggtggttgt gagaccttct gcacaaactc tgacgggagc 3660
tatgaatgta gctgtcagcc aggcttcgcg ctaatgccag accagcgatc gtgcacagac 3720
attgatgagt gtgaagacaa ccccaatatc tgtgatggtg gccagtgcac aaacatacct 3780
ggggagtaca ggtgcctgtg ctatgatggg ttcatggcat ctgaagacat gaagacttgt 3840
gtggatgtca atgagtgtga cctgaatcca aacatctgcc ttagtgggac ctgtgaaaat 3900
actaaaggct cgttcatctg ccactgtgat atgggatatt cagggaagaa aggaaaaacg 3960
ggctgtacag atatcaatga atgtgagatc ggagcacaca actgtggcag acatgctgta 4020
tgcacaaata cagccgggag cttcaagtgc agctgcagtc ccggctggat tggagacggc 4080
attaagtgca cagatctgga tgaatgctct aatggaaccc acatgtgcag ccaacacgcg 4140
gactgcaaga acaccatggg gtcatatcgc tgtctctgta aggatggcta tacaggggat 4200
ggcttcacct gtacagacct cgacgagtgc tccgagaacc tgaacctctg tggcaatggc 4260

-continued

```
cagtgcctca acgcccctgg cgggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtggaaactg cacagatgtt aatgagtgtc tggatcccac cacctgcatc   4500
agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag gagaaggttt tcgtccaaat   4800
cccatcaccg ttatattgga agacatcgat gagtgccagg agcttccagg gctgtgccaa   4860
ggggggaagt gcatcaatac ctttggcagc ttccagtgtc gctgtccaac tggttactac   4920
ctgaatgaag acactcgagt gtgtgatgat gtgaacgaat gtgagactcc tggaatctgt   4980
ggtccgggga cctgttacaa caccgttggc aactatacct gcatttgtcc tccagactac   5040
atgcaagtga acggggggaaa taattgcatg gacatgagaa gaagtctatg ctacagaaac   5100
tattacgctg acaaccagac ctgcgatgga gaactcctgt tcaacatgac caagaagatg   5160
tgctgttgct cctacaacat cggcagagcc tggaacaaac cctgtgaaca gtgccccatc   5220
ccaagcacag atgagtttgc taccctctgt gggagccaga ggcccggctt cgtgattgac   5280
atttatacgg gtttacccgt ggatattgat gaatgccggg agatccctgg ggtctgtgaa   5340
aatggagtgt gcatcaacat ggttggcagc ttccggtgtg agtgtcccgt gggattcttc   5400
tataacgaca agttactggt ttgtgaagat atcgacgagt gtcagaatgg ccctgtgtgc   5460
cagcgaaatg cggaatgcat caacactgca ggcagctacc gctgtgactg taagcccggc   5520
taccgcctta cctccacagg tcaatgcaac gatcgaaacg agtgccaaga aatcccgaac   5580
atatgcagtc atggccagtg catcgacacc gtgggaagct tctactgcct ttgtcacact   5640
ggcttcaaaa caaatgtgga tcagaccatg tgcttagaca taaatgagtg tgagagagac   5700
gcctgtggga acgggacttg cagaaacacg attggctcct tcaactgtcg ctgtaaccat   5760
ggcttcatac tgtctcacaa caatgactgc atagatgttg atgagtgtgc aactggaaac   5820
gggaaccttt gcagaaatgg ccagtgtgtc aataccgtgg gctcctttca gtgcaggtgc   5880
aatgaaggct atgaggtggc tccggacggc aggacctgtg tggatatcaa cgagtgtgtt   5940
ctggatcctg ggaaatgtgc acctggaacc tgtcagaacc tggatggctc ctacagatgc   6000
atttgcccgc ctgggtatag tctacagaat gacaagtgtg aagatattga tgagtgtgtt   6060
gaagagccag aaatctgtgc cttggggacc tgcagcaaca ctgagggtag cttcaaatgt   6120
ctgtgtccag aggggttctc cctgtcctcc actggaagaa ggtgccaaga tttgcgaatg   6180
agctactgct atgcgaagtt tgaaggtggg aagtgttcat cacccaaatc cagaaaccat   6240
tccaagcagg agtgctgctg tgctttgaag ggagaaggct ggggagatcc ttgtgagttg   6300
tgccccactg agccagatga ggctttccgc cagatctgcc cctttggaag tgggatcatt   6360
gtgggccctg atgactcagc agttgatatg gacgaatgca aagaacctga tgtctgtaga   6420
catgggcagt gcattaacac agacggctcc tatcgatgcg agtgtccttt tggttatatt   6480
ctggaaggga atgagtgtgt ggataccgat gaatgctctg tgggcaatcc ttgtggaaat   6540
gggacctgca agaatgtgat tggaggtttt gaatgtacct gtgaggaggg gttcgagcct   6600
ggcccaatga tgacttgtga agatataaat gaatgtgccc agaatcctct gctctgcgcc   6660
```

-continued

```
ttccgctgtg taaataccta cgggtcctat gaatgcaaat gccctgttgg atacgttctc   6720
cgagaagaca ggaggatgtg taaagatgag gatgagtgtg cagagggaaa acacgactgt   6780
actgagaagc aaatggagtg taagaacctc attggtacct acatgtgcat ctgcggccct   6840
gggtaccagc gcagacccga tggagagggc tgcatagatg agaatgagtg tcagaccaag   6900
cccgggatct gtgagaatgg gcgttgcctc aacaccctgg gtagctacac ttgtgagtgt   6960
aacgatggct tcacagccag ccccactcag gatgagtgct tggacaaccg ggaagggtac   7020
tgcttttcgg aggtcttgca aaacatgtgc cagattggct caagcaacag gaaccccgtc   7080
accaagtccg agtgctgctg tgatggaggg agaggctggg gaccccactg tgagatctgc   7140
cctttcgagg gcacagtggc ttacaagaag ctctgtcccc acggccgagg attcatgacc   7200
aacggagcag atattgatga gtgcaaggtt attcatgatg tttgccgaaa tggggagtgt   7260
gtcaacgaca gagggtccta tcactgcatc tgtaaaactg gctacactcc ggatataaca   7320
gggaccgcct gtgtagatct gaatgaatgc aaccaggctc ccaaaccctg caattttata   7380
tgcaaaaaca cagaagggag ttaccagtgt tcctgcccga agggctacat tctgcaagag   7440
gatggaagga gctgcaaaga tcttgacgag tgtgcaacca agcagcataa ctgtcagttc   7500
ctgtgtgtta acaccatcgg tggcttcaca tgcaaatgcc ctcctgggtt tacccagcat   7560
cacactgcct gcattgataa caatgagtgc acgtctgata tcaacctgtg tgggtccaag   7620
ggtgtttgcc agaacactcc aggaagcttc acctgtgaat gccaacgggg gttctcactc   7680
gatcagagtg gtgccagctg tgaagatgtg gacgagtgtg agggtaacca ccgctgtcaa   7740
catggctgcc agaacatcat cggaggctat aggtgtagct gcccccaggg ctacctccag   7800
cactaccaat ggaaccagtg tgtagatgaa aacgagtgcc tgagtgcaca tgtctgtgga   7860
ggagcctcct gccacaacac cctggggagt tacaagtgca tgtgtcccac cggcttccag   7920
tacgaacagt tcagtggagg ctgccaagac atcaatgagt gtggctcatc ccaggccccc   7980
tgcagttacg gttgctctaa tactgagggt ggctacctgt gtggctgtcc accaggatac   8040
ttccggatag gccaagggca ttgtgtttct ggaatgggca tgggccgagg cggcccagag   8100
ccacctgcca gcagcgagat ggacgacaac tcactgtccc cagaggcctg ctatgagtgt   8160
aagatcaacg gctacccaaa acgaggccgg aaacggagaa gcacgaacga aacggatgcc   8220
tccgacatcc aggacgggtc tgagatggaa gccaacgtga gcctcgccag ctgggatgtg   8280
gagaagccgg ctagctttgc tttcaatatt tcccatgtca ataacaaggt ccgaatccta   8340
gagctcctgc cggccctcac aactctgatg aaccacaaca gatacttgat tgaatctgga   8400
aatgaagatg gcttctttaa aatcaaccag aaagaagggg tcagctacct ccacttcacg   8460
aagaagaagc cggtggctgg gacctactcc ttacaaatca gcagcacccc actttataaa   8520
aagaaagaac ttaaccagtt agaagacaga tatgacaaag actacctcag tggtgaactg   8580
ggcgataacc tgaagatgaa aattcagatc ttgctgcatt aa                      8622
```

<210> SEQ ID NO 21
<211> LENGTH: 8623
<212> TYPE: DNA
<213> ORGANISM: Artificial Sequence
<220> FEATURE:
<223> OTHER INFORMATION: Synthetic

<400> SEQUENCE: 21

```
atgcggcgag gagggctgct ggaggtcgcg ctggcgttcg ccctgctcct cgagtcctac     60
```

-continued

```
acgagccatg gggcggacgc caatttggag gctgggagcc tgaaggagac cagagccaat    120
cgggccaaga gaagaggcgg cggaggacac gatgcgctga aaggacccaa tgtctgtgga    180
tcacgttata atgcatactg ttgtcctgga tggaaaacct tacctggtgg aaatcagtgt    240
attgttccca tttgccggca ttcctgtggg gatggattct gctcgaggcc aaatatgtgc    300
acttgcccgt ctggtcagat atctccttcc tgtggctcca gatccatcca acactgcagc    360
atccgctgta tgaatggggg cagctgcagc gatgaccact gtctgtgcca gaaagggtac    420
atcggcactc actgtggaca gcctgtctgt gaaagtggct gtctcaacgg agggaggtgt    480
gtggccccaa atcggtgtgc ttgcacgtac ggctttactg gaccccagtg tgaaagagat    540
tacagaacag gcccatgttt tactgtggta agcaaccaga tgtgccaggg acagctcagc    600
gggattgtct gcaccaaaac actttgctgt gccaccgtgg gccgagcctg gggccacccc    660
tgtgagatgt gtcctgccca gcctcacccc tgccgccgcg gcttcattcc caacatccgc    720
actggagctt gtcaagatgt ggatgaatgt caggccatcc cagggatgtg tcaaggagga    780
aattgcatta ataccgttgg atcttttgag tgcaaatgcc ctgctggaca caaatttaat    840
gaagtgtcac aaaaatgtga agatattgac gagtgcagca ccattcctgg agtctgcgat    900
ggcggggaat gtacaaacac tgtcagcagc tacttctgca aatgtccccc tggtttttac    960
acctctcctg atggcaccag atgcgtagat gttcgccctg gttactgcta cacagctctg   1020
gcaaacgggc gctgctctaa ccagctgcca cagtccataa ccaaaatgca gtgctgttgc   1080
gatcttggcc ggtgctggtc tccaggggtt actgttgctc ccgagatgtg tcccatcagg   1140
tcaactgagg atttcaacaa gctgtgctct gtccctctgg taattcccgg gagaccagaa   1200
tatcctcccc cacccattgg cccccttcct ccagttcagc ccgttcctcc tggctatcct   1260
cctgggcctg tgattccagc ccctcggcca ccgccagaat atccatatcc atctccgtct   1320
cgggaaccac caagggtgct gcctttcaac gttactgact actgtcaact ggtccgctat   1380
ctctgtcaaa atgggcgctg cattccaact cccggtagct accgctgcga gtgcaacaag   1440
ggcttccagc tggatatccg tggcgaatgc atcgacgtgg atgagtgtga gaagaaccca   1500
tgcactggtg gcgagtgcat caacaaccag ggctcctaca cctgtcactg cagagctggc   1560
taccagagca cactcaccag aactgagtgc agagacatag atgagtgtct tcagaatggc   1620
cggatctgca acaatggtcg ctgtatcaac acagacggca gcttccactg cgtatgcaat   1680
gcgggctttc atgtcacgcg ggacggaaag aactgtgaag atatggatga gtgcagcatc   1740
cgaaacatgt gcctaaacgg aatgtgtatt aatgaagatg gcagtttcaa gtgtatttgc   1800
aaacctgggt tccaactggc atcagatggc cgctactgca aagatatcaa tgagtgtgag   1860
acacctggga tctgcatgaa cggacgctgt gtgaacacgg atggctccta cagatgcgaa   1920
tgcttccccg gattggctgt gggtctagac ggacgtgtgt gtgttgacac acacatgcgg   1980
agcacatgct atggaggata caggagaggc cagtgcgtga agccgttgtt tggtgctgtt   2040
accaaatcgg aatgctgttg tgccagcact gagtatgcct ttggggaacc ctgccagccg   2100
tgtcctgcac agaattcagc ggaatatcag gcactctgca gcagtggacc gggaatgaca   2160
tcagcaggca ctgatataaa cgaatgtgca ttagatcctg atatttgccc aaatggaatt   2220
tgtgaaaatc tccgtgggac ctacaaatgt atatgcaact cgggatatga agtagacata   2280
actgggaaaa actgtgtcga tattaatgag tgtgtgctga acagtctact ttgtgacaat   2340
ggacaatgtc gaaacacacc tggaagtttt gtctgcacct gccccaaagg atttgtgtac   2400
aaacctgacc taaaaacctg tgaagacatt gatgaatgtg aatcgagtcc ttgcattaat   2460
```

-continued

```
ggagtctgca agaacagccc tggctccttc atttgtgaat gttctcctga aagtactctg   2520
gacccaacaa aaaccatctg catagaaacc atcaagggca cttgctggca gactgtcatc   2580
gacgggcgct gtgagatcaa catcaacgga gccaccttga agtccgagtg ctgctcctcc   2640
cttggtgctg cgtgggggag cccgtgcacc atctgtcaac ttgatcccat ttgtggtaaa   2700
gggttctcaa gaattaaagg cacgcaatgt gaagatatca atgagtgtga agtgttcccg   2760
ggagtatgca agaacggcct gtgtgtcaac tccaggggtt cattcaagtg cgagtgtccc   2820
aatggaatga ctttggatgc tacaggaaga atctgtcttg acatccgcct ggagacctgc   2880
ttcctcaagt atgacgatga agagtgcacc ttgcccatcg ctggccgcca ccgaatggat   2940
gcctgctgct gctctgttgg ggcagcctgg ggaacggaag agtgtgagga gtgtccattg   3000
agaaacagcc gggagtatga ggaactctgt ccccgaggac ctgggtttgc cacaaaagac   3060
attacaaatg ggaaaccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
tgtgagctga gtgcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac ctgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat tggagacggc   4080
attaagtgca cagatctgga tgaatgctct aatggaaccc acatgtgcag ccaacacgcg   4140
gactgcaaga acaccatggg gtcatatcgc tgtctctgta aggatggcta tacaggggat   4200
ggcttcacct gtacagacct cgacgagtgc tccgagaacc tgaacctctg tggcaatggc   4260
cagtgcctca acgcccctgg cgggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtggaaactg cacagatgtt aatgagtgtc tggatcccac cacctgcatc   4500
agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag gagaaggttt tcgtccaaat   4800
```

-continued

```
cccatcaccg ttatattgga agacatcgat gagtgccagg agcttccagg gctgtgccaa   4860
ggggggaagt gcatcaatac ctttggcagc ttccagtgtc gctgtccaac tggttactac   4920
ctgaatgaag acactcgagt gtgtgatgat gtgaacgaat gtgagactcc tggaatctgt   4980
ggtccgggga cctgttacaa caccgttggc aactatacct gcatttgtcc tccagactac   5040
atgcaagtga acgggggaaa taattgcatg gacatgagaa gaagtctatg ctacagaaac   5100
tattacgctg acaaccagac ctgcgatgga gaactcctgt tcaacatgac caagaagatg   5160
tgctgttgct cctacaacat cggcagagcc tggaacaaac cctgtgaaca gtgccccatc   5220
ccaagcacag atgagtttgc taccctctgt gggagccaga ggcccggctt cgtgattgac   5280
atttatacgg gtttacccgt ggatattgat gaatgccggg agatccctgg ggtctgtgaa   5340
aatggagtgt gcatcaacat ggttggcagc ttccggtgtg agtgtcccgt gggattcttc   5400
tataacgaca agttactggt ttgtgaagat atcgacgagt gtcagaatgg ccctgtgtgc   5460
cagcgaaatg cggaatgcat caacactgca ggcagctacc gctgtgactg taagcccggc   5520
taccgcctta cctccacagg tcaatgcaac gatcgaaacg agtgccaaga aatcccgaac   5580
atatgcagtc atggccagtg catcgacacc gtgggaagct tctactgcct ttgtcacact   5640
ggcttcaaaa caaatgtgga tcagaccatg tgcttagaca taaatgagtg tgagagagac   5700
gcctgtggga acgggacttg cagaaacacg attggctcct tcaactgtcg ctgtaaccat   5760
ggcttcatac tgtctcacaa caatgactgc atagatgttg atgagtgtgc aactggaaac   5820
gggaaccttt gcagaaatgg ccagtgtgtc aataccgtgg gctcctttca gtgcaggtgc   5880
aatgaaggct atgaggtggc tccggacggc aggacctgtg tggatatcaa cgagtgtgtt   5940
ctggatcctg ggaaatgtgc acctggaacc tgtcagaacc tggatggctc ctacagatgc   6000
atttgcccgc ctgggtatag tctacagaat gacaagtgtg aagatattga tgagtgtgtt   6060
gaagagccag aaatctgtgc cttggggacc tgcagcaaca ctgagggtag cttcaaatgt   6120
ctgtgtccag aggggttctc cctgtcctcc actggaagaa ggtgccaaga tttgcgaatg   6180
agctactgct atgcgaagtt tgaaggtggg aagtgttcat cacccaaatc cagaaaccat   6240
tccaagcagg agtgctgctg tgctttgaag ggagaaggct ggggagatcc ttgtgagttg   6300
tgccccactg agccagatga ggctttccgc cagatctgcc cctttggaag tgggatcatt   6360
gtgggccctg atgactcagc agttgatatg gacgaatgca aagaacctga tgtctgtaga   6420
catgggcagt gcattaacac agacggctcc tatcgatgcg agtgtccttt tggttatatt   6480
ctggaaggga atgagtgtgt ggataccgat gaatgctctg tgggcaatcc ttgtggaaat   6540
gggacctgca agaatgtgat tggaggtttt gaatgtacct gtgaggaggg gttcgagcct   6600
ggcccaatga tgacttgtga agatataaat gaatgtgccc agaatcctct gctctgcgcc   6660
ttccgctgtg taaataccta cgggtcctat gaatgcaaat gccctgttgg atacgttctc   6720
cgagaagaca ggaggatgtg taaagatgag gatgagtgtg cagagggaaa acacgactgt   6780
actgagaagc aaatggagtg taagaacctc attggtacct acatgtgcat ctgcggccct   6840
gggtaccagc gcagacccga tggagagggc tgcatagatg agaatgagtg tcagaccaag   6900
cccgggatct gtgagaatgg gcgttgcctc aacaccctgg gtagctacac ttgtgagtgt   6960
aacgatggct tcacagccag ccccactcag gatgagtgct tggacaaccg ggaagggtac   7020
tgcttttcgg aggtcttgca aaacatgtgc cagattggct caagcaacag gaaccccgtc   7080
accaagtccg agtgctgctg tgatggaggg agaggctggg gaccccactg tgagatctgc   7140
cctttcgagg gcacagtggc ttacaagaag ctctgtcccc acggccgagg attcatgacc   7200
```

-continued

```
aacggagcag atattgatga gtgcaaggtt attcatgatg tttgccgaaa tggggagtgt   7260
gtcaacgaca gagggtccta tcactgcatc tgtaaaactg gctacactcc ggatataaca   7320
gggaccgcct gtgtagatct gaatgaatgc aaccaggctc ccaaaccctg caattttata   7380
tgcaaaaaca cagaagggag ttaccagtgt tcctgcccga agggctacat tctgcaagag   7440
gatggaagga gctgcaaaga tcttgacgag tgtgcaacca agcagcataa ctgtcagttc   7500
ctgtgtgtta acaccatcgg tggcttcaca tgcaaatgcc ctcctgggtt tacccagcat   7560
cacactgcct gcattgataa caatgagtgc acgtctgata tcaacctgtg tgggtccaag   7620
ggtgtttgcc agaacactcc aggaagcttc acctgtgaat gccaacgggg gttctcactc   7680
gatcagagtg gtgccagctg tgaagatgtg gacgagtgtg agggtaacca ccgctgtcaa   7740
catggctgcc agaacatcat cggaggctat aggtgtagct gcccccaggg ctacctccag   7800
cactaccaat ggaaccagtg tgtagatgaa aacgagtgcc tgagtgcaca tgtctgtgga   7860
ggagcctcct gccacaacac cctggggagt tacaagtgca tgtgtcccac cggcttccag   7920
tacgaacagt tcagtggagg ctgccaagac atcaatgagt gtggctcatc ccaggccccc   7980
tgcagttacg gttgctctaa tactgagggt ggctacctgt gtggctgtcc accaggatac   8040
ttccggatag gccaagggca ttgtgtttct ggaatgggca tgggccgagg cggcccagag   8100
ccacctgcca gcagcgagat ggacgacaac tcactgtccc cagaggcctg ctatgagtgt   8160
aagatcaacg gctacccaaa acgaggccgg aaacggagaa gcacgaacga aaactgatgc   8220
ctccgacatc caggacgggt ctgagatgga agccaacgtg agcctcgcca gctgggatgt   8280
ggagaagccg gctagctttg ctttcaatat ttcccatgtc aataacaagg tccgaatcct   8340
agagctcctg ccggccctca caactctgat gaaccacaac agatacttga ttgaatctgg   8400
aaatgaagat ggcttcttta aaatcaacca gaaagaaggg gtcagctacc tccacttcac   8460
gaagaagaag ccggtggctg ggacctactc cttacaaatc agcagcaccc cactttataa   8520
aaagaaagaa cttaaccagt tagaagacag atatgacaaa gactacctca gtggtgaact   8580
gggcgataac ctgaagatga aaattcagat cttgctgcat taa                     8623
```

<210> SEQ ID NO 22
<211> LENGTH: 8647
<212> TYPE: DNA
<213> ORGANISM: Artificial Sequence
<220> FEATURE:
<223> OTHER INFORMATION: Synthetic

<400> SEQUENCE: 22

```
atgcggcgag gagggctgct ggaggtcgcg ctggcgttcg ccctgctcct cgagtcctac     60
acgagccatg ggcggacgc caatttggag gctgggagcc tgaaggagac cagagccaat    120
cgggccaaga gaagaggcgg cggaggacac gatgcgctga aaggacccaa tgtctgtgga    180
tcacgttata atgcatactg ttgtcctgga tggaaaacct tacctggtgg aaatcagtgt    240
attgttccca tttgccggca ttcctgtggg gatggattct gctcgaggcc aaatatgtgc    300
acttgcccgt ctggtcagat atctccttcc tgtggctcca gatccatcca acactgcagc    360
atccgctgta tgaatggggg cagctgcagc gatgaccact gtctgtgcca gaaagggtac    420
atcggcactc actgtggaca gcctgtctgt gaaagtggct gtctcaacgg agggaggtgt    480
gtggccccaa atcggtgtgc ttgcacgtac ggctttactg gaccccagtg tgaaagagat    540
tacagaacag gcccatgttt tactgtggta agcaaccaga tgtgccaggg acagctcagc    600
```

-continued

```
gggattgtct gcaccaaaac actttgctgt gccaccgtgg gccgagcctg gggccacccc    660
tgtgagatgt gtcctgccca gcctcacccc tgccgccgcg gcttcattcc caacatccgc    720
actggagctt gtcaagatgt ggatgaatgt caggccatcc cagggatgtg tcaaggagga    780
aattgcatta ataccgttgg atcttttgag tgcaaatgcc ctgctggaca caaatttaat    840
gaagtgtcac aaaaatgtga agatattgac gagtgcagca ccattcctgg agtctgcgat    900
ggcggggaat gtacaaacac tgtcagcagc tacttctgca aatgtccccc tggtttttac    960
acctctcctg atggcaccag atgcgtagat gttcgccctg gttactgcta cacagctctg   1020
gcaaacgggc gctgctctaa ccagctgcca cagtccataa ccaaaatgca gtgctgttgc   1080
gatcttggcc ggtgctggtc tccaggggtt actgttgctc ccgagatgtg tcccatcagg   1140
tcaactgagg atttcaacaa gctgtgctct gtccctctgg taattcccgg gagaccagaa   1200
tatcctcccc cacccattgg ccccccttcct ccagttcagc ccgttcctcc tggctatcct   1260
cctgggcctg tgattccagc ccctcggcca ccgccagaat atccatatcc atctccgtct   1320
cgggaaccac caagggtgct gcctttcaac gttactgact actgtcaact ggtccgctat   1380
ctctgtcaaa atgggcgctg cattccaact cccggtagct accgctgcga gtgcaacaag   1440
ggcttccagc tggatatccg tggcgaatgc atcgacgtgg atgagtgtga gaagaaccca   1500
tgcactggtg gcgagtgcat caacaaccag ggctcctaca cctgtcactg cagagctggc   1560
taccagagca cactcaccag aactgagtgc agagacatag atgagtgtct tcagaatggc   1620
cggatctgca acaatggtcg ctgtatcaac acagacggca gcttccactg cgtatgcaat   1680
gcgggctttc atgtcacgcg ggacggaaag aactgtgaag atatggatga gtgcagcatc   1740
cgaaacatgt gcctaaacgg aatgtgtatt aatgaagatg gcagtttcaa gtgtatttgc   1800
aaacctgggt tccaactggc atcagatggc cgctactgca aagatatcaa tgagtgtgag   1860
acacctggga tctgcatgaa cggacgctgt gtgaacacgg atggctccta cagatgcgaa   1920
tgcttccccg gattggctgt gggtctagac ggacgtgtgt gtgttgacac acacatgcgg   1980
agcacatgct atggaggata caggagaggc cagtgcgtga agccgttgtt tggtgctgtt   2040
accaaatcgg aatgctgttg tgccagcact gagtatgcct ttggggaacc ctgccagccg   2100
tgtcctgcac agaattcagc ggaatatcag gcactctgca gcagtggacc gggaatgaca   2160
tcagcaggca ctgatataaa cgaatgtgca ttagatcctg atatttgccc aaatggaatt   2220
tgtgaaaatc tccgtgggac ctacaaatgt atatgcaact cgggatatga agtagacata   2280
actgggaaaa actgtgtcga tattaatgag tgtgtgctga acagtctact ttgtgacaat   2340
ggacaatgtc gaaacacacc tggaagtttt gtctgcacct gccccaaagg atttgtgtac   2400
aaacctgacc taaaaacctg tgaagacatt gatgaatgtg aatcgagtcc ttgcattaat   2460
ggagtctgca agaacagccc tggctccttc atttgtgaat gttctcctga aagtactctg   2520
gacccaacaa aaaccatctg catagaaacc atcaagggca cttgctggca gactgtcatc   2580
gacgggcgct gtgagatcaa catcaacgga gccaccttga agtccgagtg ctgctcctcc   2640
cttggtgctg cgtgggggag cccgtgcacc atctgtcaac ttgatcccat ttgtggtaaa   2700
gggttctcaa gaattaaagg cacgcaatgt gaagatatca atgagtgtga agtgttcccg   2760
ggagtatgca agaacggcct gtgtgtcaac tccaggggtt cattcaagtg cgagtgtccc   2820
aatggaatga ctttggatgc tacaggaaga atctgtcttg acatccgcct ggagacctgc   2880
ttcctcaagt atgacgatga agagtgcacc ttgcccatcg ctggccgcca ccgaatggat   2940
gcctgctgct gctctgttgg ggcagcctgg ggaacggaag agtgtgagga gtgtccattg   3000
```

-continued

```
agaaacagcc gggagtatga ggaactctgt ccccgaggac ctgggtttgc cacaaaagac   3060
attacaaatg ggaaaccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
tgtgagctga gtgcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac ctgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat tggagacggc   4080
attaagtgca cagatctgga tgaatgctct aatggaaccc acatgtgcag ccaacacgcg   4140
gactgcaaga acaccatggg gtcatatcgc tgtctctgta aggatggcta tacaggggat   4200
ggcttcacct gtacagacct cgacgagtgc tccgagaacc tgaacctctg tggcaatggc   4260
cagtgcctca acgcccctgg cgggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtggaaactg cacagatgtt aatgagtgtc tggatcccac cacctgcatc   4500
agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag gagaaggttt tcgtccaaat   4800
cccatcaccg ttatattgga agacatcgat gagtgccagg agcttccagg gctgtgccaa   4860
ggggggaagt gcatcaatac ctttggcagc ttccagtgtc gctgtccaac tggttactac   4920
ctgaatgaag acactcgagt gtgtgatgat gtgaacgaat gtgagactcc tggaatctgt   4980
ggtccgggga cctgttacaa caccgttggc aactatacct gcatttgtcc tccagactac   5040
atgcaagtga acgggggaaa taattgcatg gacatgagaa gaagtctatg ctacagaaac   5100
tattacgctg acaaccagac ctgcgatgga gaactcctgt tcaacatgac caagaagatg   5160
tgctgttgct cctacaacat cggcagagcc tggaacaaac cctgtgaaca gtgccccatc   5220
ccaagcacag atgagtttgc taccctctgt gggagccaga ggcccggctt cgtgattgac   5280
atttatacgg gtttacccgt ggatattgat gaatgccggg agatccctgg ggtctgtgaa   5340
```

-continued aatggagtgt gcatcaacat ggttggcagc ttccggtgtg agtgtcccgt gggattcttc 5400
tataacgaca agttactggt ttgtgaagat atcgacgagt gtcagaatgg ccctgtgtgc 5460
cagcgaaatg cggaatgcat caacactgca ggcagctacc gctgtgactg taagcccggc 5520
taccgcctta cctccacagg tcaatgcaac gatcgaaacg agtgccaaga aatcccgaac 5580
atatgcagtc atggccagtg catcgacacc gtgggaagct tctactgcct ttgtcacact 5640
ggcttcaaaa caaatgtgga tcagaccatg tgcttagaca taaatgagtg tgagagagac 5700
gcctgtggga acgggacttg cagaaacacg attggctcct tcaactgtcg ctgtaaccat 5760
ggcttcatac tgtctcacaa caatgactgc atagatgttg atgagtgtgc aactggaaac 5820
gggaaccttt gcagaaatgg ccagtgtgtc aataccgtgg gctcctttca gtgcaggtgc 5880
aatgaaggct atgaggtggc tccggacggc aggacctgtg tggatatcaa cgagtgtgtt 5940
ctggatcctg ggaaatgtgc acctggaacc tgtcagaacc tggatggctc ctacagatgc 6000
atttgcccgc ctgggtatag tctacagaat gacaagtgtg aagatattga tgagtgtgtt 6060
gaagagccag aaatctgtgc cttggggacc tgcagcaaca ctgagggtag cttcaaatgt 6120
ctgtgtccag aggggttctc cctgtcctcc actggaagaa ggtgccaaga tttgcgaatg 6180
agctactgct atgcgaagtt tgaaggtggg aagtgttcat cacccaaatc cagaaaccat 6240
tccaagcagg agtgctgctg tgctttgaag ggagaaggct ggggagatcc ttgtgagttg 6300
tgccccactg agccagatga ggctttccgc cagatctgcc cctttggaag tgggatcatt 6360
gtgggccctg atgactcagc agttgatatg gacgaatgca aagaacctga tgtctgtaga 6420
catgggcagt gcattaacac agacggctcc tatcgatgcg agtgtccttt tggttatatt 6480
ctggaaggga atgagtgtgt ggataccgat gaatgctctg tgggcaatcc ttgtggaaat 6540
gggacctgca agaatgtgat tggaggtttt gaatgtacct gtgaggaggg gttcgagcct 6600
ggcccaatga tgacttgtga agatataaat gaatgtgccc agaatcctct gctctgcgcc 6660
ttccgctgtg taaataccta cgggtcctat gaatgcaaat gccctgttgg atacgttctc 6720
cgagaagaca ggaggatgtg taaagatgag gatgagtgtg cagagggaaa acacgactgt 6780
actgagaagc aaatggagtg taagaacctc attggtacct acatgtgcat ctgcggccct 6840
gggtaccagc gcagacccga tggagagggc tgcatagatg agaatgagtg tcagaccaag 6900
cccgggatct gtgagaatgg gcgttgcctc aacaccctgg gtagctacac ttgtgagtgt 6960
aacgatggct tcacagccag ccccactcag gatgagtgct tggacaaccg ggaagggtac 7020
tgcttttcgg aggtcttgca aaacatgtgc cagattggct caagcaacag gaaccccgtc 7080
accaagtccg agtgctgctg tgatggaggg agaggctggg gaccccactg tgagatctgc 7140
cctttcgagg gcacagtggc ttacaagaag ctctgtcccc acggccgagg attcatgacc 7200
aacggagcag atattgatga gtgcaaggtt attcatgatg tttgccgaaa tggggagtgt 7260
gtcaacgaca gagggtccta tcactgcatc tgtaaaactg gctacactcc ggatataaca 7320
gggaccgcct gtgtagatct gaatgaatgc aaccaggctc ccaaaccctg caattttata 7380
tgcaaaaaca cagaagggag ttaccagtgt tcctgcccga agggctacat tctgcaagag 7440
gatggaagga gctgcaaaga tcttgacgag tgtgcaacca agcagcataa ctgtcagttc 7500
ctgtgtgtta acaccatcgg tggcttcaca tgcaaatgcc ctcctgggtt tacccagcat 7560
cacactgcct gcattgataa caatgagtgc acgtctgata tcaacctgtg tgggtccaag 7620
ggtgtttgcc agaacactcc aggaagcttc acctgtgaat gccaacgggg gttctcactc 7680
gatcagagtg gtgccagctg tgaagatgtg gacgagtgtg agggtaacca ccgctgtcaa 7740
catggctgcc agaacatcat cggaggctat aggtgtagct gcccccaggg ctacctccag 7800
cactaccaat ggaaccagtg tgtagatgaa aacgagtgcc tgagtgcaca tgtctgtgga 7860
ggagcctcct gccacaacac cctggggagt tacaagtgca tgtgtcccac cggcttccag 7920
tacgaacagt tcagtggagg ctgccaagac atcaatgagt gtggctcatc ccaggccccc 7980
tgcagttacg gttgctctaa tactgagggt ggctacctgt gtggctgtcc accaggatac 8040
ttccggatag gccaagggca ttgtgtttct ggaatgggca tgggccgagg cggcccagag 8100
ccacctgcca gcagcgagat ggacgacaac tcactgtccc cagaggcctg ctatgagtgt 8160
aagatcaacg gctacccaaa ggcggcccag agccacctgc cagcaacgag gccggaaacg 8220
gagaagcacg aacgaaacgg atgcctccga catccaggac gggtctgaga tggaagccaa 8280
cgtgagcctc gccagctggg atgtggagaa gccggctagc tttgctttca atatttccca 8340
tgtcaataac aaggtccgaa tcctagagct cctgccggcc ctcacaactc tgatgaacca 8400
caacagatac ttgattgaat ctggaaatga agatggcttc tttaaaatca accagaaaga 8460
aggggtcagc tacctccact tcacgaagaa gaagccggtg gctgggacct actccttaca 8520
aatcagcagc accccacttt ataaaaagaa agaacttaac cagttagaag acagatatga 8580
caaagactac ctcagtggtg aactgggcga taacctgaag atgaaaattc agatcttgct 8640
gcattaa 8647

<210> SEQ ID NO 23
<211> LENGTH: 8620
<212> TYPE: DNA
<213> ORGANISM: Artificial Sequence
<220> FEATURE:
<223> OTHER INFORMATION: Synthetic

<400> SEQUENCE: 23
atgcggcgag gagggctgct ggaggtcgcg ctggcgttcg ccctgctcct cgagtcctac 60
acgagccatg ggcggacgc caatttggag gctgggagcc tgaaggagac cagagccaat 120
cgggccaaga gaagaggcgg cggaggacac gatgcgctga aaggacccaa tgtctgtgga 180
tcacgttata atgcatactg ttgtcctgga tggaaaacct tacctggtgg aaatcagtgt 240
attgttccca tttgccggca ttcctgtggg gatggattct gctcgaggcc aaatatgtgc 300
acttgcccgt ctggtcagat atctccttcc tgtggctcca gatccatcca acactgcagc 360
atccgctgta tgaatggggg cagctgcagc gatgaccact gtctgtgcca gaaagggtac 420
atcggcactc actgtggaca gcctgtctgt gaaagtggct gtctcaacgg agggaggtgt 480
gtggccccaa atcggtgtgc ttgcacgtac ggctttactg gaccccagtg tgaaagagat 540
tacagaacag gcccatgttt tactgtggta agcaaccaga tgtgccaggg acagctcagc 600
gggattgtct gcaccaaaac actttgctgt gccaccgtgg gccgagcctg gggccacccc 660
tgtgagatgt gtcctgccca gcctcacccc tgccgccgcg gcttcattcc caacatccgc 720
actggagctt gtcaagatgt ggatgaatgt caggccatcc cagggatgtg tcaaggagga 780
aattgcatta ataccgttgg atcttttgag tgcaaatgcc ctgctggaca caaatttaat 840
gaagtgtcac aaaaatgtga agatattgac gagtgcagca ccattcctgg agtctgcgat 900
ggcggggaat gtacaaacac tgtcagcagc tacttctgca aatgtccccc tggtttttac 960
acctctcctg atggcaccag atgcgtagat gttcgccctg gttactgcta cacagctctg 1020
gcaaacgggc gctgctctaa ccagctgcca cagtccataa ccaaaatgca gtgctgttgc 1080

-continued

```
gatcttggcc ggtgctggtc tccaggggtt actgttgctc ccgagatgtg tcccatcagg   1140
tcaactgagg atttcaacaa gctgtgctct gtccctctgg taattcccgg gagaccagaa   1200
tatcctcccc cacccattgg cccccttcct ccagttcagc ccgttcctcc tggctatcct   1260
cctgggcctg tgattccagc ccctcggcca ccgccagaat atccatatcc atctccgtct   1320
cgggaaccac caagggtgct gcctttcaac gttactgact actgtcaact ggtccgctat   1380
ctctgtcaaa atgggcgctg cattccaact cccggtagct accgctgcga gtgcaacaag   1440
ggcttccagc tggatatccg tggcgaatgc atcgacgtgg atgagtgtga gaagaaccca   1500
tgcactggtg gcgagtgcat caacaaccag ggctcctaca cctgtcactg cagagctggc   1560
taccagagca cactcaccag aactgagtgc agagacatag atgagtgtct tcagaatggc   1620
cggatctgca acaatggtcg ctgtatcaac acagacggca gcttccactg cgtatgcaat   1680
gcgggctttc atgtcacgcg ggacggaaag aactgtgaag atatggatga gtgcagcatc   1740
cgaaacatgt gcctaaacgg aatgtgtatt aatgaagatg gcagtttcaa gtgtatttgc   1800
aaacctgggt tccaactggc atcagatggc cgctactgca aagatatcaa tgagtgtgag   1860
acacctggga tctgcatgaa cggacgctgt gtgaacacgg atggctccta cagatgcgaa   1920
tgcttccccg gattggctgt gggtctagac ggacgtgtgt gtgttgacac acacatgcgg   1980
agcacatgct atggaggata caggagaggc cagtgcgtga agccgttgtt tggtgctgtt   2040
accaaatcgg aatgctgttg tgccagcact gagtatgcct ttggggaacc ctgccagccg   2100
tgtcctgcac agaattcagc ggaatatcag gcactctgca gcagtggacc gggaatgaca   2160
tcagcaggca ctgatataaa cgaatgtgca ttagatcctg atatttgccc aaatggaatt   2220
tgtgaaaatc tccgtgggac ctacaaatgt atatgcaact cgggatatga agtagacata   2280
actgggaaaa actgtgtcga tattaatgag tgtgtgctga acagtctact ttgtgacaat   2340
ggacaatgtc gaaacacacc tggaagtttt gtctgcacct gccccaaagg atttgtgtac   2400
aaacctgacc taaaaacctg tgaagacatt gatgaatgtg aatcgagtcc ttgcattaat   2460
ggagtctgca agaacagccc tggctccttc atttgtgaat gttctcctga aagtactctg   2520
gacccaacaa aaaccatctg catagaaacc atcaagggca cttgctggca gactgtcatc   2580
gacgggcgct gtgagatcaa catcaacgga gccaccttga agtccgagtg ctgctcctcc   2640
cttggtgctg cgtgggggag cccgtgcacc atctgtcaac ttgatcccat ttgtggtaaa   2700
gggttctcaa gaattaaagg cacgcaatgt gaagatatca atgagtgtga agtgttcccg   2760
ggagtatgca agaacggcct gtgtgtcaac tccaggggtt cattcaagtg cgagtgtccc   2820
aatggaatga ctttggatgc tacaggaaga atctgtcttg acatccgcct ggagacctgc   2880
ttcctcaagt atgacgatga agagtgcacc ttgcccatcg ctggccgcca ccgaatggat   2940
gcctgctgct gctctgttgg ggcagcctgg ggaacggaag agtgtgagga gtgtccattg   3000
agaaacagcc gggagtatga ggaactctgt ccccgaggac ctgggtttgc cacaaaagac   3060
attacaaatg ggaaaccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
```

```
tgtgagctga gtgcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac ctgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat tggagacggc   4080
attaagtgca cagatctgga tgaatgctct aatggaaccc acatgtgcag ccaacacgcg   4140
gactgcaaga acaccatggg gtcatatcgc tgtctctgta aggatggcta tacaggggat   4200
ggcttcacct gtacagacct cgacgagtgc tccgagaacc tgaacctctg tggcaatggc   4260
cagtgcctca acgcccctgg cgggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtggaaactg cacagatgtt aatgagtgtc tggatcccac cacctgcatc   4500
agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag gagaaggttt tcgtccaaat   4800
cccatcaccg ttatattgga agacatcgat gagtgccagg agcttccagg gctgtgccaa   4860
ggggggaagt gcatcaatac ctttggcagc ttccagtgtc gctgtccaac tggttactac   4920
ctgaatgaag acactcgagt gtgtgatgat gtgaacgaat gtgagactcc tggaatctgt   4980
ggtccgggga cctgttacaa caccgttggc aactatacct gcatttgtcc tccagactac   5040
atgcaagtga acgggggaaa taattgcatg gacatgagaa gaagtctatg ctacagaaac   5100
tattacgctg acaaccagac ctgcgatgga gaactcctgt tcaacatgac caagaagatg   5160
tgctgttgct cctacaacat cggcagagcc tggaacaaac cctgtgaaca gtgccccatc   5220
ccaagcacag atgagtttgc taccctctgt gggagccaga ggcccggctt cgtgattgac   5280
atttatacgg gtttacccgt ggatattgat gaatgccggg agatccctgg ggtctgtgaa   5340
aatggagtgt gcatcaacat ggttggcagc ttccggtgtg agtgtcccgt gggattcttc   5400
tataacgaca agttactggt ttgtgaagat atcgacgagt gtcagaatgg ccctgtgtgc   5460
cagcgaaatg cggaatgcat caacactgca ggcagctacc gctgtgactg taagcccggc   5520
taccgcctta cctccacagg tcaatgcaac gatcgaaacg agtgccaaga aatcccgaac   5580
atatgcagtc atggccagtg catcgacacc gtgggaagct tctactgcct ttgtcacact   5640
ggcttcaaaa caaatgtgga tcagaccatg tgcttagaca taaatgagtg tgagagagac   5700
gcctgtggga acgggacttg cagaaacacg attggctcct tcaactgtcg ctgtaaccat   5760
ggcttcatac tgtctcacaa caatgactgc atagatgttg atgagtgtgc aactggaaac   5820
```

-continued gggaaccttt gcagaaatgg ccagtgtgtc aataccgtgg gctcctttca gtgcaggtgc 5880
aatgaaggct atgaggtggc tccggacggc aggacctgtg tggatatcaa cgagtgtgtt 5940
ctggatcctg ggaaatgtgc acctggaacc tgtcagaacc tggatggctc ctacagatgc 6000
atttgcccgc ctgggtatag tctacagaat gacaagtgtg aagatattga tgagtgtgtt 6060
gaagagccag aaatctgtgc cttggggacc tgcagcaaca ctgagggtag cttcaaatgt 6120
ctgtgtccag aggggttctc cctgtcctcc actggaagaa ggtgccaaga tttgcgaatg 6180
agctactgct atgcgaagtt tgaaggtggg aagtgttcat cacccaaatc cagaaaccat 6240
tccaagcagg agtgctgctg tgctttgaag ggagaaggct ggggagatcc ttgtgagttg 6300
tgccccactg agccagatga ggctttccgc cagatctgcc cctttggaag tgggatcatt 6360
gtgggccctg atgactcagc agttgatatg gacgaatgca aagaacctga tgtctgtaga 6420
catgggcagt gcattaacac agacggctcc tatcgatgcg agtgtccttt tggttatatt 6480
ctggaaggga atgagtgtgt ggataccgat gaatgctctg tgggcaatcc ttgtggaaat 6540
gggacctgca agaatgtgat tggaggtttt gaatgtacct gtgaggaggg gttcgagcct 6600
ggcccaatga tgacttgtga agatataaat gaatgtgccc agaatcctct gctctgcgcc 6660
ttccgctgtg taaataccta cgggtcctat gaatgcaaat gccctgttgg atacgttctc 6720
cgagaagaca ggaggatgtg taaagatgag gatgagtgtg cagagggaaa acacgactgt 6780
actgagaagc aaatggagtg taagaacctc attggtacct acatgtgcat ctgcggccct 6840
gggtaccagc gcagacccga tggagagggc tgcatagatg agaatgagtg tcagaccaag 6900
cccgggatct gtgagaatgg gcgttgcctc aacaccctgg gtagctacac ttgtgagtgt 6960
aacgatggct tcacagccag ccccactcag gatgagtgct tggacaaccg ggaagggtac 7020
tgcttttcgg aggtcttgca aaacatgtgc cagattggct caagcaacag gaaccccgtc 7080
accaagtccg agtgctgctg tgatggaggg agaggctggg gaccccactg tgagatctgc 7140
cctttcgagg gcacagtggc ttacaagaag ctctgtcccc acggccgagg attcatgacc 7200
aacggagcag atattgatga gtgcaaggtt attcatgatg tttgccgaaa tggggagtgt 7260
gtcaacgaca gagggtccta tcactgcatc tgtaaaactg gctacactcc ggatataaca 7320
gggaccgcct gtgtagatct gaatgaatgc aaccaggctc ccaaaccctg caattttata 7380
tgcaaaaaca cagaagggag ttaccagtgt tcctgcccga agggctacat tctgcaagag 7440
gatggaagga gctgcaaaga tcttgacgag tgtgcaacca agcagcataa ctgtcagttc 7500
ctgtgtgtta acaccatcgg tggcttcaca tgcaaatgcc ctcctgggtt tacccagcat 7560
cacactgcct gcattgataa caatgagtgc acgtctgata tcaacctgtg tgggtccaag 7620
ggtgtttgcc agaacactcc aggaagcttc acctgtgaat gccaacgggg gttctcactc 7680
gatcagagtg gtgccagctg tgaagatgtg gacgagtgtg agggtaacca ccgctgtcaa 7740
catggctgcc agaacatcat cggaggctat aggtgtagct gcccccaggg ctacctccag 7800
cactaccaat ggaaccagtg tgtagatgaa aacgagtgcc tgagtgcaca tgtctgtgga 7860
ggagcctcct gccacaacac cctggggagt tacaagtgca tgtgtcccac cggcttccag 7920
tacgaacagt tcagtggagg ctgccaagac atcaatgagt gtggctcatc ccaggccccc 7980
tgcagttacg gttgctctaa tactgagggt ggctacctgt gtggctgtcc accaggatac 8040
ttccggatag gccaagggca ttgtgtttct ggaatgggca tgggccgagg cggcccagag 8100
ccacctgcca gcagcgagat ggacgacaac tcactgtccc cagaggcctg ctatgagtgt 8160
gatcaatggc taccccaaac ggggcaggaa acggagaagc acaaacgaaa ctgatgcctc 8220

```
cgacatccag gacgggtctg agatggaagc caacgtgagc ctcgccagct gggatgtgga   8280

gaagccggct agctttgctt tcaatatttc ccatgtcaat aacaaggtcc gaatcctaga   8340

gctcctgccg gccctcacaa ctctgatgaa ccacaacaga tacttgattg aatctggaaa   8400

tgaagatggc ttctttaaaa tcaaccagaa agaaggggtc agctacctcc acttcacgaa   8460

gaagaagccg gtggctggga cctactcctt acaaatcagc agcaccccac tttataaaaa   8520

gaaagaactt aaccagttag aagacagata tgacaaagac tacctcagtg gtgaactggg   8580

cgataacctg aagatgaaaa ttcagatctt gctgcattaa                         8620
```

<210> SEQ ID NO 24
<211> LENGTH: 175
<212> TYPE: DNA
<213> ORGANISM: Homo sapiens

<400> SEQUENCE: 24

```
gcactgtgtt tctggaatgg gcatgggccg aggaaaccca gagccacctg tcagtggtga     60

aatggatgac aattcactct ccccagaggc ttgttacgag tgtaagatca atggctaccc    120

caaacggggc aggaaacgga gaagcacaaa cgaaactgat gcctccaata tcgag         175
```

<210> SEQ ID NO 25
<211> LENGTH: 175
<212> TYPE: DNA
<213> ORGANISM: Mus musculus

<400> SEQUENCE: 25

```
gcattgtgtt tctggaatgg gcatgggccg aggcggccca gagccacctg ccagcagcga     60

gatggacgac aactcactgt ccccagaggc ctgctatgag tgtaagatca acggctaccc    120

aaaacgaggc cggaaacgga gaagcacgaa cgaaacggat gcctccgaca tccag         175
```

<210> SEQ ID NO 26
<211> LENGTH: 176
<212> TYPE: DNA
<213> ORGANISM: Artificial Sequence
<220> FEATURE:
<223> OTHER INFORMATION: Synthetic

<400> SEQUENCE: 26

```
gcattgtgtt tctggaatgg gcatgggccg aggcggccca gagccacctg ccagcagcga     60

gatggacgac aactcactgt ccccagaggc ctgctatgag tgtaagatca acggctaccc    120

aaaacgaggc cggaaacgga gaagcacgaa cgaaaactga tgcctccgac atccag        176
```

<210> SEQ ID NO 27
<211> LENGTH: 200
<212> TYPE: DNA
<213> ORGANISM: Artificial Sequence
<220> FEATURE:
<223> OTHER INFORMATION: Synthetic

<400> SEQUENCE: 27

```
gcattgtgtt tctggaatgg gcatgggccg aggcggccca gagccacctg ccagcagcga     60

gatggacgac aactcactgt ccccagaggc ctgctatgag tgtaagatca acggctaccc    120

aaaggcggcc cagagccacc tgccagcaac gaggccggaa acggagaagc acgaacgaaa    180

cggatgcctc cgacatccag                                                200
```

<210> SEQ ID NO 28

<211> LENGTH: 173
<212> TYPE: DNA
<213> ORGANISM: Artificial Sequence
<220> FEATURE:
<223> OTHER INFORMATION: Synthetic

<400> SEQUENCE: 28
gcattgtgtt tctggaatgg gcatgggccg aggcggccca gagccacctg ccagcagcga 60
gatggacgac aactcactgt ccccagaggc ctgctatgag tgtgatcaat ggctacccca 120
aacggggcag gaaacggaga agcacaaacg aaactgatgc ctccgacatc cag 173

<210> SEQ ID NO 29
<211> LENGTH: 2871
<212> TYPE: PRT
<213> ORGANISM: Homo sapiens

<400> SEQUENCE: 29

Met Arg Arg Gly Arg Leu Leu Glu Ile Ala Leu Gly Phe Thr Val Leu
1 5 10 15

Leu Ala Ser Tyr Thr Ser His Gly Ala Asp Ala Asn Leu Glu Ala Gly
20 25 30

Asn Val Lys Glu Thr Arg Ala Ser Arg Ala Lys Arg Arg Gly Gly Gly
35 40 45

Gly His Asp Ala Leu Lys Gly Pro Asn Val Cys Gly Ser Arg Tyr Asn
50 55 60

Ala Tyr Cys Cys Pro Gly Trp Lys Thr Leu Pro Gly Gly Asn Gln Cys
65 70 75 80

Ile Val Pro Ile Cys Arg His Ser Cys Gly Asp Gly Phe Cys Ser Arg
85 90 95

Pro Asn Met Cys Thr Cys Pro Ser Gly Gln Ile Ala Pro Ser Cys Gly
100 105 110

Ser Arg Ser Ile Gln His Cys Asn Ile Arg Cys Met Asn Gly Gly Ser
115 120 125

Cys Ser Asp Asp His Cys Leu Cys Gln Lys Gly Tyr Ile Gly Thr His
130 135 140

Cys Gly Gln Pro Val Cys Glu Ser Gly Cys Leu Asn Gly Gly Arg Cys
145 150 155 160

Val Ala Pro Asn Arg Cys Ala Cys Thr Tyr Gly Phe Thr Gly Pro Gln
165 170 175

Cys Glu Arg Asp Tyr Arg Thr Gly Pro Cys Phe Thr Val Ile Ser Asn
180 185 190

Gln Met Cys Gln Gly Gln Leu Ser Gly Ile Val Cys Thr Lys Thr Leu
195 200 205

Cys Cys Ala Thr Val Gly Arg Ala Trp Gly His Pro Cys Glu Met Cys
210 215 220

Pro Ala Gln Pro His Pro Cys Arg Arg Gly Phe Ile Pro Asn Ile Arg
225 230 235 240

Thr Gly Ala Cys Gln Asp Val Asp Glu Cys Gln Ala Ile Pro Gly Leu
245 250 255

Cys Gln Gly Gly Asn Cys Ile Asn Thr Val Gly Ser Phe Glu Cys Lys
260 265 270

Cys Pro Ala Gly His Lys Leu Asn Glu Val Ser Gln Lys Cys Glu Asp
275 280 285

Ile Asp Glu Cys Ser Thr Ile Pro Gly Ile Cys Glu Gly Gly Glu Cys
290 295 300

-continued

```
Thr Asn Thr Val Ser Ser Tyr Phe Cys Lys Cys Pro Pro Gly Phe Tyr
305                 310                 315                 320

Thr Ser Pro Asp Gly Thr Arg Cys Ile Asp Val Arg Pro Gly Tyr Cys
                325                 330                 335

Tyr Thr Ala Leu Thr Asn Gly Arg Cys Ser Asn Gln Leu Pro Gln Ser
            340                 345                 350

Ile Thr Lys Met Gln Cys Cys Cys Asp Ala Gly Arg Cys Trp Ser Pro
        355                 360                 365

Gly Val Thr Val Ala Pro Glu Met Cys Pro Ile Arg Ala Thr Glu Asp
    370                 375                 380

Phe Asn Lys Leu Cys Ser Val Pro Met Val Ile Pro Gly Arg Pro Glu
385                 390                 395                 400

Tyr Pro Pro Pro Pro Leu Gly Pro Ile Pro Pro Val Leu Pro Val Pro
                405                 410                 415

Pro Gly Phe Pro Pro Gly Pro Gln Ile Pro Val Pro Arg Pro Pro Val
            420                 425                 430

Glu Tyr Leu Tyr Pro Ser Arg Glu Pro Pro Arg Val Leu Pro Val Asn
        435                 440                 445

Val Thr Asp Tyr Cys Gln Leu Val Arg Tyr Leu Cys Gln Asn Gly Arg
    450                 455                 460

Cys Ile Pro Thr Pro Gly Ser Tyr Arg Cys Glu Cys Asn Lys Gly Phe
465                 470                 475                 480

Gln Leu Asp Leu Arg Gly Glu Cys Ile Asp Val Asp Glu Cys Glu Lys
                485                 490                 495

Asn Pro Cys Ala Gly Gly Glu Cys Ile Asn Asn Gln Gly Ser Tyr Thr
            500                 505                 510

Cys Gln Cys Arg Ala Gly Tyr Gln Ser Thr Leu Thr Arg Thr Glu Cys
        515                 520                 525

Arg Asp Ile Asp Glu Cys Leu Gln Asn Gly Arg Ile Cys Asn Asn Gly
    530                 535                 540

Arg Cys Ile Asn Thr Asp Gly Ser Phe His Cys Val Cys Asn Ala Gly
545                 550                 555                 560

Phe His Val Thr Arg Asp Gly Lys Asn Cys Glu Asp Met Asp Glu Cys
                565                 570                 575

Ser Ile Arg Asn Met Cys Leu Asn Gly Met Cys Ile Asn Glu Asp Gly
            580                 585                 590

Ser Phe Lys Cys Ile Cys Lys Pro Gly Phe Gln Leu Ala Ser Asp Gly
        595                 600                 605

Arg Tyr Cys Lys Asp Ile Asn Glu Cys Glu Thr Pro Gly Ile Cys Met
    610                 615                 620

Asn Gly Arg Cys Val Asn Thr Asp Gly Ser Tyr Arg Cys Glu Cys Phe
625                 630                 635                 640

Pro Gly Leu Ala Val Gly Leu Asp Gly Arg Val Cys Val Asp Thr His
                645                 650                 655

Met Arg Ser Thr Cys Tyr Gly Gly Tyr Lys Arg Gly Gln Cys Ile Lys
            660                 665                 670

Pro Leu Phe Gly Ala Val Thr Lys Ser Glu Cys Cys Cys Ala Ser Thr
        675                 680                 685

Glu Tyr Ala Phe Gly Glu Pro Cys Gln Pro Cys Pro Ala Gln Asn Ser
    690                 695                 700

Ala Glu Tyr Gln Ala Leu Cys Ser Ser Gly Pro Gly Met Thr Ser Ala
705                 710                 715                 720

Gly Ser Asp Ile Asn Glu Cys Ala Leu Asp Pro Asp Ile Cys Pro Asn
```

-continued 725 730 735

Gly Ile Cys Glu Asn Leu Arg Gly Thr Tyr Lys Cys Ile Cys Asn Ser
740 745 750

Gly Tyr Glu Val Asp Ser Thr Gly Lys Asn Cys Val Asp Ile Asn Glu
755 760 765

Cys Val Leu Asn Ser Leu Leu Cys Asp Asn Gly Gln Cys Arg Asn Thr
770 775 780

Pro Gly Ser Phe Val Cys Thr Cys Pro Lys Gly Phe Ile Tyr Lys Pro
785 790 795 800

Asp Leu Lys Thr Cys Glu Asp Ile Asp Glu Cys Glu Ser Ser Pro Cys
805 810 815

Ile Asn Gly Val Cys Lys Asn Ser Pro Gly Ser Phe Ile Cys Glu Cys
820 825 830

Ser Ser Glu Ser Thr Leu Asp Pro Thr Lys Thr Ile Cys Ile Glu Thr
835 840 845

Ile Lys Gly Thr Cys Trp Gln Thr Val Ile Asp Gly Arg Cys Glu Ile
850 855 860

Asn Ile Asn Gly Ala Thr Leu Lys Ser Gln Cys Cys Ser Ser Leu Gly
865 870 875 880

Ala Ala Trp Gly Ser Pro Cys Thr Leu Cys Gln Val Asp Pro Ile Cys
885 890 895

Gly Lys Gly Tyr Ser Arg Ile Lys Gly Thr Gln Cys Glu Asp Ile Asp
900 905 910

Glu Cys Glu Val Phe Pro Gly Val Cys Lys Asn Gly Leu Cys Val Asn
915 920 925

Thr Arg Gly Ser Phe Lys Cys Gln Cys Pro Ser Gly Met Thr Leu Asp
930 935 940

Ala Thr Gly Arg Ile Cys Leu Asp Ile Arg Leu Glu Thr Cys Phe Leu
945 950 955 960

Arg Tyr Glu Asp Glu Glu Cys Thr Leu Pro Ile Ala Gly Arg His Arg
965 970 975

Met Asp Ala Cys Cys Cys Ser Val Gly Ala Ala Trp Gly Thr Glu Glu
980 985 990

Cys Glu Glu Cys Pro Met Arg Asn Thr Pro Glu Tyr Glu Glu Leu Cys
995 1000 1005

Pro Arg Gly Pro Gly Phe Ala Thr Lys Glu Ile Thr Asn Gly Lys
1010 1015 1020

Pro Phe Phe Lys Asp Ile Asn Glu Cys Lys Met Ile Pro Ser Leu
1025 1030 1035

Cys Thr His Gly Lys Cys Arg Asn Thr Ile Gly Ser Phe Lys Cys
1040 1045 1050

Arg Cys Asp Ser Gly Phe Ala Leu Asp Ser Glu Glu Arg Asn Cys
1055 1060 1065

Thr Asp Ile Asp Glu Cys Arg Ile Ser Pro Asp Leu Cys Gly Arg
1070 1075 1080

Gly Gln Cys Val Asn Thr Pro Gly Asp Phe Glu Cys Lys Cys Asp
1085 1090 1095

Glu Gly Tyr Glu Ser Gly Phe Met Met Met Lys Asn Cys Met Asp
1100 1105 1110

Ile Asp Glu Cys Gln Arg Asp Pro Leu Leu Cys Arg Gly Gly Val
1115 1120 1125

Cys His Asn Thr Glu Gly Ser Tyr Arg Cys Glu Cys Pro Pro Gly
1130 1135 1140

-continued

```
His Gln Leu Ser Pro Asn Ile Ser Ala Cys Ile Asp Ile Asn Glu
    1145                1150                1155

Cys Glu Leu Ser Ala His Leu Cys Pro Asn Gly Arg Cys Val Asn
    1160                1165                1170

Leu Ile Gly Lys Tyr Gln Cys Ala Cys Asn Pro Gly Tyr His Ser
    1175                1180                1185

Thr Pro Asp Arg Leu Phe Cys Val Asp Ile Asp Glu Cys Ser Ile
    1190                1195                1200

Met Asn Gly Gly Cys Glu Thr Phe Cys Thr Asn Ser Glu Gly Ser
    1205                1210                1215

Tyr Glu Cys Ser Cys Gln Pro Gly Phe Ala Leu Met Pro Asp Gln
    1220                1225                1230

Arg Ser Cys Thr Asp Ile Asp Glu Cys Glu Asp Asn Pro Asn Ile
    1235                1240                1245

Cys Asp Gly Gly Gln Cys Thr Asn Ile Pro Gly Glu Tyr Arg Cys
    1250                1255                1260

Leu Cys Tyr Asp Gly Phe Met Ala Ser Glu Asp Met Lys Thr Cys
    1265                1270                1275

Val Asp Val Asn Glu Cys Asp Leu Asn Pro Asn Ile Cys Leu Ser
    1280                1285                1290

Gly Thr Cys Glu Asn Thr Lys Gly Ser Phe Ile Cys His Cys Asp
    1295                1300                1305

Met Gly Tyr Ser Gly Lys Lys Gly Lys Thr Gly Cys Thr Asp Ile
    1310                1315                1320

Asn Glu Cys Glu Ile Gly Ala His Asn Cys Gly Lys His Ala Val
    1325                1330                1335

Cys Thr Asn Thr Ala Gly Ser Phe Lys Cys Ser Cys Ser Pro Gly
    1340                1345                1350

Trp Ile Gly Asp Gly Ile Lys Cys Thr Asp Leu Asp Glu Cys Ser
    1355                1360                1365

Asn Gly Thr His Met Cys Ser Gln His Ala Asp Cys Lys Asn Thr
    1370                1375                1380

Met Gly Ser Tyr Arg Cys Leu Cys Lys Glu Gly Tyr Thr Gly Asp
    1385                1390                1395

Gly Phe Thr Cys Thr Asp Leu Asp Glu Cys Ser Glu Asn Leu Asn
    1400                1405                1410

Leu Cys Gly Asn Gly Gln Cys Leu Asn Ala Pro Gly Gly Tyr Arg
    1415                1420                1425

Cys Glu Cys Asp Met Gly Phe Val Pro Ser Ala Asp Gly Lys Ala
    1430                1435                1440

Cys Glu Asp Ile Asp Glu Cys Ser Leu Pro Asn Ile Cys Val Phe
    1445                1450                1455

Gly Thr Cys His Asn Leu Pro Gly Leu Phe Arg Cys Glu Cys Glu
    1460                1465                1470

Ile Gly Tyr Glu Leu Asp Arg Ser Gly Gly Asn Cys Thr Asp Val
    1475                1480                1485

Asn Glu Cys Leu Asp Pro Thr Thr Cys Ile Ser Gly Asn Cys Val
    1490                1495                1500

Asn Thr Pro Gly Ser Tyr Ile Cys Asp Cys Pro Pro Asp Phe Glu
    1505                1510                1515

Leu Asn Pro Thr Arg Val Gly Cys Val Asp Thr Arg Ser Gly Asn
    1520                1525                1530
```

```
Cys Tyr  Leu Asp Ile Arg Pro  Arg Gly Asp Asn Gly  Asp Thr Ala
    1535                 1540                 1545

Cys Ser  Asn Glu Ile Gly Val  Gly Val Ser Lys Ala  Ser Cys Cys
    1550                 1555                 1560

Cys Ser  Leu Gly Lys Ala Trp  Gly Thr Pro Cys Glu  Met Cys Pro
    1565                 1570                 1575

Ala Val  Asn Thr Ser Glu Tyr  Lys Ile Leu Cys Pro  Gly Gly Glu
    1580                 1585                 1590

Gly Phe  Arg Pro Asn Pro Ile  Thr Val Ile Leu Glu  Asp Ile Asp
    1595                 1600                 1605

Glu Cys  Gln Glu Leu Pro Gly  Leu Cys Gln Gly Gly  Lys Cys Ile
    1610                 1615                 1620

Asn Thr  Phe Gly Ser Phe Gln  Cys Arg Cys Pro Thr  Gly Tyr Tyr
    1625                 1630                 1635

Leu Asn  Glu Asp Thr Arg Val  Cys Asp Asp Val Asn  Glu Cys Glu
    1640                 1645                 1650

Thr Pro  Gly Ile Cys Gly Pro  Gly Thr Cys Tyr Asn  Thr Val Gly
    1655                 1660                 1665

Asn Tyr  Thr Cys Ile Cys Pro  Pro Asp Tyr Met Gln  Val Asn Gly
    1670                 1675                 1680

Gly Asn  Asn Cys Met Asp Met  Arg Arg Ser Leu Cys  Tyr Arg Asn
    1685                 1690                 1695

Tyr Tyr  Ala Asp Asn Gln Thr  Cys Asp Gly Glu Leu  Leu Phe Asn
    1700                 1705                 1710

Met Thr  Lys Lys Met Cys Cys  Cys Ser Tyr Asn Ile  Gly Arg Ala
    1715                 1720                 1725

Trp Asn  Lys Pro Cys Glu Gln  Cys Pro Ile Pro Ser  Thr Asp Glu
    1730                 1735                 1740

Phe Ala  Thr Leu Cys Gly Ser  Gln Arg Pro Gly Phe  Val Ile Asp
    1745                 1750                 1755

Ile Tyr  Thr Gly Leu Pro Val  Asp Ile Asp Glu Cys  Arg Glu Ile
    1760                 1765                 1770

Pro Gly  Val Cys Glu Asn Gly  Val Cys Ile Asn Met  Val Gly Ser
    1775                 1780                 1785

Phe Arg  Cys Glu Cys Pro Val  Gly Phe Phe Tyr Asn  Asp Lys Leu
    1790                 1795                 1800

Leu Val  Cys Glu Asp Ile Asp  Glu Cys Gln Asn Gly  Pro Val Cys
    1805                 1810                 1815

Gln Arg  Asn Ala Glu Cys Ile  Asn Thr Ala Gly Ser  Tyr Arg Cys
    1820                 1825                 1830

Asp Cys  Lys Pro Gly Tyr Arg  Phe Thr Ser Thr Gly  Gln Cys Asn
    1835                 1840                 1845

Asp Arg  Asn Glu Cys Gln Glu  Ile Pro Asn Ile Cys  Ser His Gly
    1850                 1855                 1860

Gln Cys  Ile Asp Thr Val Gly  Ser Phe Tyr Cys Leu  Cys His Thr
    1865                 1870                 1875

Gly Phe  Lys Thr Asn Asp Asp  Gln Thr Met Cys Leu  Asp Ile Asn
    1880                 1885                 1890

Glu Cys  Glu Arg Asp Ala Cys  Gly Asn Gly Thr Cys  Arg Asn Thr
    1895                 1900                 1905

Ile Gly  Ser Phe Asn Cys Arg  Cys Asn His Gly Phe  Ile Leu Ser
    1910                 1915                 1920

His Asn  Asn Asp Cys Ile Asp  Val Asp Glu Cys Ala  Ser Gly Asn
```

-continued

```
    1925                1930                1935

Gly Asn  Leu Cys Arg Asn Gly  Gln Cys Ile Asn Thr  Val Gly Ser
    1940                1945                1950

Phe Gln  Cys Gln Cys Asn Glu  Gly Tyr Glu Val Ala  Pro Asp Gly
    1955                1960                1965

Arg Thr  Cys Val Asp Ile Asn  Glu Cys Leu Leu Glu  Pro Arg Lys
    1970                1975                1980

Cys Ala  Pro Gly Thr Cys Gln  Asn Leu Asp Gly Ser  Tyr Arg Cys
    1985                1990                1995

Ile Cys  Pro Pro Gly Tyr Ser  Leu Gln Asn Glu Lys  Cys Glu Asp
    2000                2005                2010

Ile Asp  Glu Cys Val Glu Glu  Pro Glu Ile Cys Ala  Leu Gly Thr
    2015                2020                2025

Cys Ser  Asn Thr Glu Gly Ser  Phe Lys Cys Leu Cys  Pro Glu Gly
    2030                2035                2040

Phe Ser  Leu Ser Ser Ser Gly  Arg Arg Cys Gln Asp  Leu Arg Met
    2045                2050                2055

Ser Tyr  Cys Tyr Ala Lys Phe  Glu Gly Gly Lys Cys  Ser Ser Pro
    2060                2065                2070

Lys Ser  Arg Asn His Ser Lys  Gln Glu Cys Cys Cys  Ala Leu Lys
    2075                2080                2085

Gly Glu  Gly Trp Gly Asp Pro  Cys Glu Leu Cys Pro  Thr Glu Pro
    2090                2095                2100

Asp Glu  Ala Phe Arg Gln Ile  Cys Pro Tyr Gly Ser  Gly Ile Ile
    2105                2110                2115

Val Gly  Pro Asp Asp Ser Ala  Val Asp Met Asp Glu  Cys Lys Glu
    2120                2125                2130

Pro Asp  Val Cys Lys His Gly  Gln Cys Ile Asn Thr  Asp Gly Ser
    2135                2140                2145

Tyr Arg  Cys Glu Cys Pro Phe  Gly Tyr Ile Leu Ala  Gly Asn Glu
    2150                2155                2160

Cys Val  Asp Thr Asp Glu Cys  Ser Val Gly Asn Pro  Cys Gly Asn
    2165                2170                2175

Gly Thr  Cys Lys Asn Val Ile  Gly Gly Phe Glu Cys  Thr Cys Glu
    2180                2185                2190

Glu Gly  Phe Glu Pro Gly Pro  Met Met Thr Cys Glu  Asp Ile Asn
    2195                2200                2205

Glu Cys  Ala Gln Asn Pro Leu  Leu Cys Ala Phe Arg  Cys Val Asn
    2210                2215                2220

Thr Tyr  Gly Ser Tyr Glu Cys  Lys Cys Pro Val Gly  Tyr Val Leu
    2225                2230                2235

Arg Glu  Asp Arg Arg Met Cys  Lys Asp Glu Asp Glu  Cys Glu Glu
    2240                2245                2250

Gly Lys  His Asp Cys Thr Glu  Lys Gln Met Glu Cys  Lys Asn Leu
    2255                2260                2265

Ile Gly  Thr Tyr Met Cys Ile  Cys Gly Pro Gly Tyr  Gln Arg Arg
    2270                2275                2280

Pro Asp  Gly Glu Gly Cys Val  Asp Glu Asn Glu Cys  Gln Thr Lys
    2285                2290                2295

Pro Gly  Ile Cys Glu Asn Gly  Arg Cys Leu Asn Thr  Arg Gly Ser
    2300                2305                2310

Tyr Thr  Cys Glu Cys Asn Asp  Gly Phe Thr Ala Ser  Pro Asn Gln
    2315                2320                2325
```

```
Asp Glu Cys Leu Asp Asn Arg Glu Gly Tyr Cys Phe Thr Glu Val
    2330                2335                2340

Leu Gln Asn Met Cys Gln Ile Gly Ser Ser Asn Arg Asn Pro Val
    2345                2350                2355

Thr Lys Ser Glu Cys Cys Cys Asp Gly Gly Arg Gly Trp Gly Pro
    2360                2365                2370

His Cys Glu Ile Cys Pro Phe Gln Gly Thr Val Ala Phe Lys Lys
    2375                2380                2385

Leu Cys Pro His Gly Arg Gly Phe Met Thr Asn Gly Ala Asp Ile
    2390                2395                2400

Asp Glu Cys Lys Val Ile His Asp Val Cys Arg Asn Gly Glu Cys
    2405                2410                2415

Val Asn Asp Arg Gly Ser Tyr His Cys Ile Cys Lys Thr Gly Tyr
    2420                2425                2430

Thr Pro Asp Ile Thr Gly Thr Ser Cys Val Asp Leu Asn Glu Cys
    2435                2440                2445

Asn Gln Ala Pro Lys Pro Cys Asn Phe Ile Cys Lys Asn Thr Glu
    2450                2455                2460

Gly Ser Tyr Gln Cys Ser Cys Pro Lys Gly Tyr Ile Leu Gln Glu
    2465                2470                2475

Asp Gly Arg Ser Cys Lys Asp Leu Asp Glu Cys Ala Thr Lys Gln
    2480                2485                2490

His Asn Cys Gln Phe Leu Cys Val Asn Thr Ile Gly Gly Phe Thr
    2495                2500                2505

Cys Lys Cys Pro Pro Gly Phe Thr Gln His His Thr Ser Cys Ile
    2510                2515                2520

Asp Asn Asn Glu Cys Thr Ser Asp Ile Asn Leu Cys Gly Ser Lys
    2525                2530                2535

Gly Ile Cys Gln Asn Thr Pro Gly Ser Phe Thr Cys Glu Cys Gln
    2540                2545                2550

Arg Gly Phe Ser Leu Asp Gln Thr Gly Ser Ser Cys Glu Asp Val
    2555                2560                2565

Asp Glu Cys Glu Gly Asn His Arg Cys Gln His Gly Cys Gln Asn
    2570                2575                2580

Ile Ile Gly Gly Tyr Arg Cys Ser Cys Pro Gln Gly Tyr Leu Gln
    2585                2590                2595

His Tyr Gln Trp Asn Gln Cys Val Asp Glu Asn Glu Cys Leu Ser
    2600                2605                2610

Ala His Ile Cys Gly Gly Ala Ser Cys His Asn Thr Leu Gly Ser
    2615                2620                2625

Tyr Lys Cys Met Cys Pro Ala Gly Phe Gln Tyr Glu Gln Phe Ser
    2630                2635                2640

Gly Gly Cys Gln Asp Ile Asn Glu Cys Gly Ser Ala Gln Ala Pro
    2645                2650                2655

Cys Ser Tyr Gly Cys Ser Asn Thr Glu Gly Gly Tyr Leu Cys Gly
    2660                2665                2670

Cys Pro Pro Gly Tyr Phe Arg Ile Gly Gln Gly His Cys Val Ser
    2675                2680                2685

Gly Met Gly Met Gly Arg Gly Asn Pro Glu Pro Pro Val Ser Gly
    2690                2695                2700

Glu Met Asp Asp Asn Ser Leu Ser Pro Glu Ala Cys Tyr Glu Cys
    2705                2710                2715
```

```
Lys Ile  Asn Gly Tyr Pro Lys  Arg Gly Arg Lys Arg  Arg Ser Thr
    2720                 2725                 2730

Asn Glu  Thr Asp Ala Ser Asn  Ile Glu Asp Gln Ser  Glu Thr Glu
    2735                 2740                 2745

Ala Asn  Val Ser Leu Ala Ser  Trp Asp Val Glu Lys  Thr Ala Ile
    2750                 2755                 2760

Phe Ala  Phe Asn Ile Ser His  Val Ser Asn Lys Val  Arg Ile Leu
    2765                 2770                 2775

Glu Leu  Leu Pro Ala Leu Thr  Thr Leu Thr Asn His  Asn Arg Tyr
    2780                 2785                 2790

Leu Ile  Glu Ser Gly Asn Glu  Asp Gly Phe Phe Lys  Ile Asn Gln
    2795                 2800                 2805

Lys Glu  Gly Ile Ser Tyr Leu  His Phe Thr Lys Lys  Lys Pro Val
    2810                 2815                 2820

Ala Gly  Thr Tyr Ser Leu Gln  Ile Ser Ser Thr Pro  Leu Tyr Lys
    2825                 2830                 2835

Lys Lys  Glu Leu Asn Gln Leu  Glu Asp Lys Tyr Asp  Lys Asp Tyr
    2840                 2845                 2850

Leu Ser  Gly Glu Leu Gly Asp  Asn Leu Lys Met Lys  Ile Gln Val
    2855                 2860                 2865

Leu Leu  His
    2870


<210> SEQ ID NO 30
<211> LENGTH: 2873
<212> TYPE: PRT
<213> ORGANISM: Mus musculus

<400> SEQUENCE: 30

Met Arg Arg Gly Gly Leu Leu Glu Val Ala Leu Ala Phe Ala Leu Leu
1               5                   10                  15

Leu Glu Ser Tyr Thr Ser His Gly Ala Asp Ala Asn Leu Glu Ala Gly
            20                  25                  30

Ser Leu Lys Glu Thr Arg Ala Asn Arg Ala Lys Arg Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
        115                 120                 125

Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
        195                 200                 205
```

```
Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
        275                 280                 285

Ile Asp Glu Cys Ser Thr Ile Pro Gly Val Cys Asp Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
        355                 360                 365

Gly Val Thr Val Ala Pro Glu Met Cys Pro Ile Arg Ser Thr Glu Asp
    370                 375                 380

Phe Asn Lys Leu Cys Ser Val Pro Leu Val Ile Pro Gly Arg Pro Glu
385                 390                 395                 400

Tyr Pro Pro Pro Pro Ile Gly Pro Leu Pro Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
        435                 440                 445

Phe Asn Val Thr Asp Tyr Cys Gln Leu Val Arg Tyr Leu Cys Gln Asn
    450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
            500                 505                 510

Tyr Thr Cys His Cys Arg Ala Gly Tyr Gln Ser Thr Leu Thr Arg Thr
        515                 520                 525

Glu Cys Arg Asp Ile Asp Glu Cys Leu Gln Asn Gly Arg Ile Cys Asn
    530                 535                 540

Asn Gly Arg Cys Ile Asn Thr Asp Gly Ser Phe His Cys Val Cys Asn
545                 550                 555                 560

Ala Gly Phe His Val Thr Arg Asp Gly Lys Asn Cys Glu Asp Met Asp
                565                 570                 575

Glu Cys Ser Ile Arg Asn Met Cys Leu Asn Gly Met Cys Ile Asn Glu
            580                 585                 590

Asp Gly Ser Phe Lys Cys Ile Cys Lys Pro Gly Phe Gln Leu Ala Ser
        595                 600                 605

Asp Gly Arg Tyr Cys Lys Asp Ile Asn Glu Cys Glu Thr Pro Gly Ile
    610                 615                 620
```

-continued

```
Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
                645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
        675                 680                 685

Ser Thr Glu Tyr Ala Phe Gly Glu Pro Cys Gln Pro Cys Pro Ala Gln
    690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
                725                 730                 735

Pro Asn Gly Ile Cys Glu Asn Leu Arg Gly Thr Tyr Lys Cys Ile Cys
            740                 745                 750

Asn Ser Gly Tyr Glu Val Asp Ile Thr Gly Lys Asn Cys Val Asp Ile
        755                 760                 765

Asn Glu Cys Val Leu Asn Ser Leu Leu Cys Asp Asn Gly Gln Cys Arg
    770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
                805                 810                 815

Pro Cys Ile Asn Gly Val Cys Lys Asn Ser Pro Gly Ser Phe Ile Cys
            820                 825                 830

Glu Cys Ser Pro Glu Ser Thr Leu Asp Pro Thr Lys Thr Ile Cys Ile
        835                 840                 845

Glu Thr Ile Lys Gly Thr Cys Trp Gln Thr Val Ile Asp Gly Arg Cys
    850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
                885                 890                 895

Ile Cys Gly Lys Gly Phe Ser Arg Ile Lys Gly Thr Gln Cys Glu Asp
            900                 905                 910

Ile Asn Glu Cys Glu Val Phe Pro Gly Val Cys Lys Asn Gly Leu Cys
        915                 920                 925

Val Asn Ser Arg Gly Ser Phe Lys Cys Glu Cys Pro Asn Gly Met Thr
    930                 935                 940

Leu Asp Ala Thr Gly Arg Ile Cys Leu Asp Ile Arg Leu Glu Thr Cys
945                 950                 955                 960

Phe Leu Lys Tyr Asp Asp Glu Glu Cys Thr Leu Pro Ile Ala Gly Arg
                965                 970                 975

His Arg Met Asp Ala Cys Cys Cys Ser Val Gly Ala Ala Trp Gly Thr
            980                 985                 990

Glu Glu Cys Glu Glu Cys Pro Leu  Arg Asn Ser Arg Glu  Tyr Glu Glu
        995                 1000                 1005

Leu Cys  Pro Arg Gly Pro Gly  Phe Ala Thr Lys Asp  Ile Thr Asn
    1010                 1015                 1020

Gly Lys  Pro Phe Phe Lys Asp  Ile Asn Glu Cys Lys  Met Ile Pro
    1025                 1030                 1035

Ser Leu  Cys Thr His Gly Lys  Cys Arg Asn Thr Ile  Gly Ser Phe
```

```
    1040                1045                1050

Lys Cys  Arg Cys Asp Ser Gly  Phe Ala Leu Asp Ser  Glu Glu Arg
    1055                1060                1065

Asn Cys  Thr Asp Ile Asp Glu  Cys Arg Ile Ser Pro  Asp Leu Cys
    1070                1075                1080

Gly Arg  Gly Gln Cys Val Asn  Thr Pro Gly Asp Phe  Glu Cys Lys
    1085                1090                1095

Cys Asp  Glu Gly Tyr Glu Ser  Gly Phe Met Met Met  Lys Asn Cys
    1100                1105                1110

Met Asp  Ile Asp Glu Cys Gln  Arg Asp Pro Leu Leu  Cys Arg Gly
    1115                1120                1125

Gly Ile  Cys His Asn Thr Glu  Gly Ser Tyr Arg Cys  Glu Cys Pro
    1130                1135                1140

Pro Gly  His Gln Leu Ser Pro  Asn Ile Ser Ala Cys  Ile Asp Ile
    1145                1150                1155

Asn Glu  Cys Glu Leu Ser Ala  Asn Leu Cys Pro His  Gly Arg Cys
    1160                1165                1170

Val Asn  Leu Ile Gly Lys Tyr  Gln Cys Ala Cys Asn  Pro Gly Tyr
    1175                1180                1185

His Pro  Thr His Asp Arg Leu  Phe Cys Val Asp Ile  Asp Glu Cys
    1190                1195                1200

Ser Ile  Met Asn Gly Gly Cys  Glu Thr Phe Cys Thr  Asn Ser Asp
    1205                1210                1215

Gly Ser  Tyr Glu Cys Ser Cys  Gln Pro Gly Phe Ala  Leu Met Pro
    1220                1225                1230

Asp Gln  Arg Ser Cys Thr Asp  Ile Asp Glu Cys Glu  Asp Asn Pro
    1235                1240                1245

Asn Ile  Cys Asp Gly Gly Gln  Cys Thr Asn Ile Pro  Gly Glu Tyr
    1250                1255                1260

Arg Cys  Leu Cys Tyr Asp Gly  Phe Met Ala Ser Glu  Asp Met Lys
    1265                1270                1275

Thr Cys  Val Asp Val Asn Glu  Cys Asp Leu Asn Pro  Asn Ile Cys
    1280                1285                1290

Leu Ser  Gly Thr Cys Glu Asn  Thr Lys Gly Ser Phe  Ile Cys His
    1295                1300                1305

Cys Asp  Met Gly Tyr Ser Gly  Lys Lys Gly Lys Thr  Gly Cys Thr
    1310                1315                1320

Asp Ile  Asn Glu Cys Glu Ile  Gly Ala His Asn Cys  Gly Arg His
    1325                1330                1335

Ala Val  Cys Thr Asn Thr Ala  Gly Ser Phe Lys Cys  Ser Cys Ser
    1340                1345                1350

Pro Gly  Trp Ile Gly Asp Gly  Ile Lys Cys Thr Asp  Leu Asp Glu
    1355                1360                1365

Cys Ser  Asn Gly Thr His Met  Cys Ser Gln His Ala  Asp Cys Lys
    1370                1375                1380

Asn Thr  Met Gly Ser Tyr Arg  Cys Leu Cys Lys Asp  Gly Tyr Thr
    1385                1390                1395

Gly Asp  Gly Phe Thr Cys Thr  Asp Leu Asp Glu Cys  Ser Glu Asn
    1400                1405                1410

Leu Asn  Leu Cys Gly Asn Gly  Gln Cys Leu Asn Ala  Pro Gly Gly
    1415                1420                1425

Tyr Arg  Cys Glu Cys Asp Met  Gly Phe Val Pro Ser  Ala Asp Gly
    1430                1435                1440
```

-continued

Lys Ala Cys Glu Asp Ile Asp Glu Cys Ser Leu Pro Asn Ile Cys
1445 1450 1455

Val Phe Gly Thr Cys His Asn Leu Pro Gly Leu Phe Arg Cys Glu
1460 1465 1470

Cys Glu Ile Gly Tyr Glu Leu Asp Arg Ser Gly Gly Asn Cys Thr
1475 1480 1485

Asp Val Asn Glu Cys Leu Asp Pro Thr Thr Cys Ile Ser Gly Asn
1490 1495 1500

Cys Val Asn Thr Pro Gly Ser Tyr Thr Cys Asp Cys Pro Pro Asp
1505 1510 1515

Phe Glu Leu Asn Pro Thr Arg Val Gly Cys Val Asp Thr Arg Ser
1520 1525 1530

Gly Asn Cys Tyr Leu Asp Ile Arg Pro Arg Gly Asp Asn Gly Asp
1535 1540 1545

Thr Ala Cys Ser Asn Glu Ile Gly Val Gly Val Ser Lys Ala Ser
1550 1555 1560

Cys Cys Cys Ser Leu Gly Lys Ala Trp Gly Thr Pro Cys Glu Leu
1565 1570 1575

Cys Pro Ser Val Asn Thr Ser Glu Tyr Lys Ile Leu Cys Pro Gly
1580 1585 1590

Gly Glu Gly Phe Arg Pro Asn Pro Ile Thr Val Ile Leu Glu Asp
1595 1600 1605

Ile Asp Glu Cys Gln Glu Leu Pro Gly Leu Cys Gln Gly Gly Lys
1610 1615 1620

Cys Ile Asn Thr Phe Gly Ser Phe Gln Cys Arg Cys Pro Thr Gly
1625 1630 1635

Tyr Tyr Leu Asn Glu Asp Thr Arg Val Cys Asp Asp Val Asn Glu
1640 1645 1650

Cys Glu Thr Pro Gly Ile Cys Gly Pro Gly Thr Cys Tyr Asn Thr
1655 1660 1665

Val Gly Asn Tyr Thr Cys Ile Cys Pro Pro Asp Tyr Met Gln Val
1670 1675 1680

Asn Gly Gly Asn Asn Cys Met Asp Met Arg Arg Ser Leu Cys Tyr
1685 1690 1695

Arg Asn Tyr Tyr Ala Asp Asn Gln Thr Cys Asp Gly Glu Leu Leu
1700 1705 1710

Phe Asn Met Thr Lys Lys Met Cys Cys Cys Ser Tyr Asn Ile Gly
1715 1720 1725

Arg Ala Trp Asn Lys Pro Cys Glu Gln Cys Pro Ile Pro Ser Thr
1730 1735 1740

Asp Glu Phe Ala Thr Leu Cys Gly Ser Gln Arg Pro Gly Phe Val
1745 1750 1755

Ile Asp Ile Tyr Thr Gly Leu Pro Val Asp Ile Asp Glu Cys Arg
1760 1765 1770

Glu Ile Pro Gly Val Cys Glu Asn Gly Val Cys Ile Asn Met Val
1775 1780 1785

Gly Ser Phe Arg Cys Glu Cys Pro Val Gly Phe Phe Tyr Asn Asp
1790 1795 1800

Lys Leu Leu Val Cys Glu Asp Ile Asp Glu Cys Gln Asn Gly Pro
1805 1810 1815

Val Cys Gln Arg Asn Ala Glu Cys Ile Asn Thr Ala Gly Ser Tyr
1820 1825 1830

-continued

```
Arg Cys  Asp Cys Lys Pro Gly  Tyr Arg Leu Thr Ser  Thr Gly Gln
    1835                 1840                 1845

Cys Asn  Asp Arg Asn Glu Cys  Gln Glu Ile Pro Asn  Ile Cys Ser
    1850                 1855                 1860

His Gly  Gln Cys Ile Asp Thr  Val Gly Ser Phe Tyr  Cys Leu Cys
    1865                 1870                 1875

His Thr  Gly Phe Lys Thr Asn  Val Asp Gln Thr Met  Cys Leu Asp
    1880                 1885                 1890

Ile Asn  Glu Cys Glu Arg Asp  Ala Cys Gly Asn Gly  Thr Cys Arg
    1895                 1900                 1905

Asn Thr  Ile Gly Ser Phe Asn  Cys Arg Cys Asn His  Gly Phe Ile
    1910                 1915                 1920

Leu Ser  His Asn Asn Asp Cys  Ile Asp Val Asp Glu  Cys Ala Thr
    1925                 1930                 1935

Gly Asn  Gly Asn Leu Cys Arg  Asn Gly Gln Cys Val  Asn Thr Val
    1940                 1945                 1950

Gly Ser  Phe Gln Cys Arg Cys  Asn Glu Gly Tyr Glu  Val Ala Pro
    1955                 1960                 1965

Asp Gly  Arg Thr Cys Val Asp  Ile Asn Glu Cys Val  Leu Asp Pro
    1970                 1975                 1980

Gly Lys  Cys Ala Pro Gly Thr  Cys Gln Asn Leu Asp  Gly Ser Tyr
    1985                 1990                 1995

Arg Cys  Ile Cys Pro Pro Gly  Tyr Ser Leu Gln Asn  Asp Lys Cys
    2000                 2005                 2010

Glu Asp  Ile Asp Glu Cys Val  Glu Glu Pro Glu Ile  Cys Ala Leu
    2015                 2020                 2025

Gly Thr  Cys Ser Asn Thr Glu  Gly Ser Phe Lys Cys  Leu Cys Pro
    2030                 2035                 2040

Glu Gly  Phe Ser Leu Ser Ser  Thr Gly Arg Arg Cys  Gln Asp Leu
    2045                 2050                 2055

Arg Met  Ser Tyr Cys Tyr Ala  Lys Phe Glu Gly Gly  Lys Cys Ser
    2060                 2065                 2070

Ser Pro  Lys Ser Arg Asn His  Ser Lys Gln Glu Cys  Cys Cys Ala
    2075                 2080                 2085

Leu Lys  Gly Glu Gly Trp Gly  Asp Pro Cys Glu Leu  Cys Pro Thr
    2090                 2095                 2100

Glu Pro  Asp Glu Ala Phe Arg  Gln Ile Cys Pro Phe  Gly Ser Gly
    2105                 2110                 2115

Ile Ile  Val Gly Pro Asp Asp  Ser Ala Val Asp Met  Asp Glu Cys
    2120                 2125                 2130

Lys Glu  Pro Asp Val Cys Arg  His Gly Gln Cys Ile  Asn Thr Asp
    2135                 2140                 2145

Gly Ser  Tyr Arg Cys Glu Cys  Pro Phe Gly Tyr Ile  Leu Glu Gly
    2150                 2155                 2160

Asn Glu  Cys Val Asp Thr Asp  Glu Cys Ser Val Gly  Asn Pro Cys
    2165                 2170                 2175

Gly Asn  Gly Thr Cys Lys Asn  Val Ile Gly Gly Phe  Glu Cys Thr
    2180                 2185                 2190

Cys Glu  Glu Gly Phe Glu Pro  Gly Pro Met Met Thr  Cys Glu Asp
    2195                 2200                 2205

Ile Asn  Glu Cys Ala Gln Asn  Pro Leu Leu Cys Ala  Phe Arg Cys
    2210                 2215                 2220

Val Asn  Thr Tyr Gly Ser Tyr  Glu Cys Lys Cys Pro  Val Gly Tyr
```

```
    2225                2230                2235

Val Leu  Arg Glu Asp Arg Arg  Met Cys Lys Asp Glu  Asp Glu Cys
    2240                2245                2250

Ala Glu  Gly Lys His Asp Cys  Thr Glu Lys Gln Met  Glu Cys Lys
    2255                2260                2265

Asn Leu  Ile Gly Thr Tyr Met  Cys Ile Cys Gly Pro  Gly Tyr Gln
    2270                2275                2280

Arg Arg  Pro Asp Gly Glu Gly  Cys Ile Asp Glu Asn  Glu Cys Gln
    2285                2290                2295

Thr Lys  Pro Gly Ile Cys Glu  Asn Gly Arg Cys Leu  Asn Thr Leu
    2300                2305                2310

Gly Ser  Tyr Thr Cys Glu Cys  Asn Asp Gly Phe Thr  Ala Ser Pro
    2315                2320                2325

Thr Gln  Asp Glu Cys Leu Asp  Asn Arg Glu Gly Tyr  Cys Phe Ser
    2330                2335                2340

Glu Val  Leu Gln Asn Met Cys  Gln Ile Gly Ser Ser  Asn Arg Asn
    2345                2350                2355

Pro Val  Thr Lys Ser Glu Cys  Cys Cys Asp Gly Gly  Arg Gly Trp
    2360                2365                2370

Gly Pro  His Cys Glu Ile Cys  Pro Phe Glu Gly Thr  Val Ala Tyr
    2375                2380                2385

Lys Lys  Leu Cys Pro His Gly  Arg Gly Phe Met Thr  Asn Gly Ala
    2390                2395                2400

Asp Ile  Asp Glu Cys Lys Val  Ile His Asp Val Cys  Arg Asn Gly
    2405                2410                2415

Glu Cys  Val Asn Asp Arg Gly  Ser Tyr His Cys Ile  Cys Lys Thr
    2420                2425                2430

Gly Tyr  Thr Pro Asp Ile Thr  Gly Thr Ala Cys Val  Asp Leu Asn
    2435                2440                2445

Glu Cys  Asn Gln Ala Pro Lys  Pro Cys Asn Phe Ile  Cys Lys Asn
    2450                2455                2460

Thr Glu  Gly Ser Tyr Gln Cys  Ser Cys Pro Lys Gly  Tyr Ile Leu
    2465                2470                2475

Gln Glu  Asp Gly Arg Ser Cys  Lys Asp Leu Asp Glu  Cys Ala Thr
    2480                2485                2490

Lys Gln  His Asn Cys Gln Phe  Leu Cys Val Asn Thr  Ile Gly Gly
    2495                2500                2505

Phe Thr  Cys Lys Cys Pro Pro  Gly Phe Thr Gln His  His Thr Ala
    2510                2515                2520

Cys Ile  Asp Asn Asn Glu Cys  Thr Ser Asp Ile Asn  Leu Cys Gly
    2525                2530                2535

Ser Lys  Gly Val Cys Gln Asn  Thr Pro Gly Ser Phe  Thr Cys Glu
    2540                2545                2550

Cys Gln  Arg Gly Phe Ser Leu  Asp Gln Ser Gly Ala  Ser Cys Glu
    2555                2560                2565

Asp Val  Asp Glu Cys Glu Gly  Asn His Arg Cys Gln  His Gly Cys
    2570                2575                2580

Gln Asn  Ile Ile Gly Gly Tyr  Arg Cys Ser Cys Pro  Gln Gly Tyr
    2585                2590                2595

Leu Gln  His Tyr Gln Trp Asn  Gln Cys Val Asp Glu  Asn Glu Cys
    2600                2605                2610

Leu Ser  Ala His Val Cys Gly  Gly Ala Ser Cys His  Asn Thr Leu
    2615                2620                2625
```

-continued

Gly Ser Tyr Lys Cys Met Cys Pro Thr Gly Phe Gln Tyr Glu Gln
2630 2635 2640

Phe Ser Gly Gly Cys Gln Asp Ile Asn Glu Cys Gly Ser Ser Gln
2645 2650 2655

Ala Pro Cys Ser Tyr Gly Cys Ser Asn Thr Glu Gly Gly Tyr Leu
2660 2665 2670

Cys Gly Cys Pro Pro Gly Tyr Phe Arg Ile Gly Gln Gly His Cys
2675 2680 2685

Val Ser Gly Met Gly Met Gly Arg Gly Gly Pro Glu Pro Pro Ala
2690 2695 2700

Ser Ser Glu Met Asp Asp Asn Ser Leu Ser Pro Glu Ala Cys Tyr
2705 2710 2715

Glu Cys Lys Ile Asn Gly Tyr Pro Lys Arg Gly Arg Lys Arg Arg
2720 2725 2730

Ser Thr Asn Glu Thr Asp Ala Ser Asp Ile Gln Asp Gly Ser Glu
2735 2740 2745

Met Glu Ala Asn Val Ser Leu Ala Ser Trp Asp Val Glu Lys Pro
2750 2755 2760

Ala Ser Phe Ala Phe Asn Ile Ser His Val Asn Asn Lys Val Arg
2765 2770 2775

Ile Leu Glu Leu Leu Pro Ala Leu Thr Thr Leu Met Asn His Asn
2780 2785 2790

Arg Tyr Leu Ile Glu Ser Gly Asn Glu Asp Gly Phe Phe Lys Ile
2795 2800 2805

Asn Gln Lys Glu Gly Val Ser Tyr Leu His Phe Thr Lys Lys Lys
2810 2815 2820

Pro Val Ala Gly Thr Tyr Ser Leu Gln Ile Ser Ser Thr Pro Leu
2825 2830 2835

Tyr Lys Lys Lys Glu Leu Asn Gln Leu Glu Asp Arg Tyr Asp Lys
2840 2845 2850

Asp Tyr Leu Ser Gly Glu Leu Gly Asp Asn Leu Lys Met Lys Ile
2855 2860 2865

Gln Ile Leu Leu His
2870

<210> SEQ ID NO 31
<211> LENGTH: 2738
<212> TYPE: PRT
<213> ORGANISM: Artificial Sequence
<220> FEATURE:
<223> OTHER INFORMATION: Synthetic

<400> SEQUENCE: 31

Met Arg Arg Gly Gly Leu Leu Glu Val Ala Leu Ala Phe Ala Leu Leu
1 5 10 15

Leu Glu Ser Tyr Thr Ser His Gly Ala Asp Ala Asn Leu Glu Ala Gly
20 25 30

Ser Leu Lys Glu Thr Arg Ala Asn Arg Ala Lys Arg Arg Gly Gly Gly
35 40 45

Gly His Asp Ala Leu Lys Gly Pro Asn Val Cys Gly Ser Arg Tyr Asn
50 55 60

Ala Tyr Cys Cys Pro Gly Trp Lys Thr Leu Pro Gly Gly Asn Gln Cys
65 70 75 80

Ile Val Pro Ile Cys Arg His Ser Cys Gly Asp Gly Phe Cys Ser Arg
85 90 95

-continued

```
Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
        115                 120                 125

Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
        275                 280                 285

Ile Asp Glu Cys Ser Thr Ile Pro Gly Val Cys Asp Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
        355                 360                 365

Gly Val Thr Val Ala Pro Glu Met Cys Pro Ile Arg Ser Thr Glu Asp
    370                 375                 380

Phe Asn Lys Leu Cys Ser Val Pro Leu Val Ile Pro Gly Arg Pro Glu
385                 390                 395                 400

Tyr Pro Pro Pro Pro Ile Gly Pro Leu Pro Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
        435                 440                 445

Phe Asn Val Thr Asp Tyr Cys Gln Leu Val Arg Tyr Leu Cys Gln Asn
    450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
            500                 505                 510
```

-continued

```
Tyr Thr Cys His Cys Arg Ala Gly Tyr Gln Ser Thr Leu Thr Arg Thr
        515                 520                 525

Glu Cys Arg Asp Ile Asp Glu Cys Leu Gln Asn Gly Arg Ile Cys Asn
    530                 535                 540

Asn Gly Arg Cys Ile Asn Thr Asp Gly Ser Phe His Cys Val Cys Asn
545                 550                 555                 560

Ala Gly Phe His Val Thr Arg Asp Gly Lys Asn Cys Glu Asp Met Asp
                565                 570                 575

Glu Cys Ser Ile Arg Asn Met Cys Leu Asn Gly Met Cys Ile Asn Glu
            580                 585                 590

Asp Gly Ser Phe Lys Cys Ile Cys Lys Pro Gly Phe Gln Leu Ala Ser
        595                 600                 605

Asp Gly Arg Tyr Cys Lys Asp Ile Asn Glu Cys Glu Thr Pro Gly Ile
    610                 615                 620

Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
                645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
        675                 680                 685

Ser Thr Glu Tyr Ala Phe Gly Glu Pro Cys Gln Pro Cys Pro Ala Gln
    690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
                725                 730                 735

Pro Asn Gly Ile Cys Glu Asn Leu Arg Gly Thr Tyr Lys Cys Ile Cys
            740                 745                 750

Asn Ser Gly Tyr Glu Val Asp Ile Thr Gly Lys Asn Cys Val Asp Ile
        755                 760                 765

Asn Glu Cys Val Leu Asn Ser Leu Leu Cys Asp Asn Gly Gln Cys Arg
    770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
                805                 810                 815

Pro Cys Ile Asn Gly Val Cys Lys Asn Ser Pro Gly Ser Phe Ile Cys
            820                 825                 830

Glu Cys Ser Pro Glu Ser Thr Leu Asp Pro Thr Lys Thr Ile Cys Ile
        835                 840                 845

Glu Thr Ile Lys Gly Thr Cys Trp Gln Thr Val Ile Asp Gly Arg Cys
    850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
                885                 890                 895

Ile Cys Gly Lys Gly Phe Ser Arg Ile Lys Gly Thr Gln Cys Glu Asp
            900                 905                 910

Ile Asn Glu Cys Glu Val Phe Pro Gly Val Cys Lys Asn Gly Leu Cys
        915                 920                 925

Val Asn Ser Arg Gly Ser Phe Lys Cys Glu Cys Pro Asn Gly Met Thr
```

-continued

```
    930                 935                 940

Leu Asp Ala Thr Gly Arg Ile Cys Leu Asp Ile Arg Leu Glu Thr Cys
945                 950                 955                 960

Phe Leu Lys Tyr Asp Asp Glu Glu Cys Thr Leu Pro Ile Ala Gly Arg
                965                 970                 975

His Arg Met Asp Ala Cys Cys Cys Ser Val Gly Ala Ala Trp Gly Thr
            980                 985                 990

Glu Glu Cys Glu Glu Cys Pro Leu  Arg Asn Ser Arg Glu  Tyr Glu Glu
        995                 1000                1005

Leu Cys  Pro Arg Gly Pro Gly  Phe Ala Thr Lys Asp  Ile Thr Asn
    1010                 1015                 1020

Gly Lys  Pro Phe Phe Lys Asp  Ile Asn Glu Cys Lys  Met Ile Pro
    1025                 1030                 1035

Ser Leu  Cys Thr His Gly Lys  Cys Arg Asn Thr Ile  Gly Ser Phe
    1040                 1045                 1050

Lys Cys  Arg Cys Asp Ser Gly  Phe Ala Leu Asp Ser  Glu Glu Arg
    1055                 1060                 1065

Asn Cys  Thr Asp Ile Asp Glu  Cys Arg Ile Ser Pro  Asp Leu Cys
    1070                 1075                 1080

Gly Arg  Gly Gln Cys Val Asn  Thr Pro Gly Asp Phe  Glu Cys Lys
    1085                 1090                 1095

Cys Asp  Glu Gly Tyr Glu Ser  Gly Phe Met Met Met  Lys Asn Cys
    1100                 1105                 1110

Met Asp  Ile Asp Glu Cys Gln  Arg Asp Pro Leu Leu  Cys Arg Gly
    1115                 1120                 1125

Gly Ile  Cys His Asn Thr Glu  Gly Ser Tyr Arg Cys  Glu Cys Pro
    1130                 1135                 1140

Pro Gly  His Gln Leu Ser Pro  Asn Ile Ser Ala Cys  Ile Asp Ile
    1145                 1150                 1155

Asn Glu  Cys Glu Leu Ser Ala  Asn Leu Cys Pro His  Gly Arg Cys
    1160                 1165                 1170

Val Asn  Leu Ile Gly Lys Tyr  Gln Cys Ala Cys Asn  Pro Gly Tyr
    1175                 1180                 1185

His Pro  Thr His Asp Arg Leu  Phe Cys Val Asp Ile  Asp Glu Cys
    1190                 1195                 1200

Ser Ile  Met Asn Gly Gly Cys  Glu Thr Phe Cys Thr  Asn Ser Asp
    1205                 1210                 1215

Gly Ser  Tyr Glu Cys Ser Cys  Gln Pro Gly Phe Ala  Leu Met Pro
    1220                 1225                 1230

Asp Gln  Arg Ser Cys Thr Asp  Ile Asp Glu Cys Glu  Asp Asn Pro
    1235                 1240                 1245

Asn Ile  Cys Asp Gly Gly Gln  Cys Thr Asn Ile Pro  Gly Glu Tyr
    1250                 1255                 1260

Arg Cys  Leu Cys Tyr Asp Gly  Phe Met Ala Ser Glu  Asp Met Lys
    1265                 1270                 1275

Thr Cys  Val Asp Val Asn Glu  Cys Asp Leu Asn Pro  Asn Ile Cys
    1280                 1285                 1290

Leu Ser  Gly Thr Cys Glu Asn  Thr Lys Gly Ser Phe  Ile Cys His
    1295                 1300                 1305

Cys Asp  Met Gly Tyr Ser Gly  Lys Lys Gly Lys Thr  Gly Cys Thr
    1310                 1315                 1320

Asp Ile  Asn Glu Cys Glu Ile  Gly Ala His Asn Cys  Gly Arg His
    1325                 1330                 1335
```

```
Ala Val Cys Thr Asn Thr Ala Gly Ser Phe Lys Cys Ser Cys Ser
    1340                1345                1350

Pro Gly Trp Ile Gly Asp Gly Ile Lys Cys Thr Asp Leu Asp Glu
    1355                1360                1365

Cys Ser Asn Gly Thr His Met Cys Ser Gln His Ala Asp Cys Lys
    1370                1375                1380

Asn Thr Met Gly Ser Tyr Arg Cys Leu Cys Lys Asp Gly Tyr Thr
    1385                1390                1395

Gly Asp Gly Phe Thr Cys Thr Asp Leu Asp Glu Cys Ser Glu Asn
    1400                1405                1410

Leu Asn Leu Cys Gly Asn Gly Gln Cys Leu Asn Ala Pro Gly Gly
    1415                1420                1425

Tyr Arg Cys Glu Cys Asp Met Gly Phe Val Pro Ser Ala Asp Gly
    1430                1435                1440

Lys Ala Cys Glu Asp Ile Asp Glu Cys Ser Leu Pro Asn Ile Cys
    1445                1450                1455

Val Phe Gly Thr Cys His Asn Leu Pro Gly Leu Phe Arg Cys Glu
    1460                1465                1470

Cys Glu Ile Gly Tyr Glu Leu Asp Arg Ser Gly Gly Asn Cys Thr
    1475                1480                1485

Asp Val Asn Glu Cys Leu Asp Pro Thr Thr Cys Ile Ser Gly Asn
    1490                1495                1500

Cys Val Asn Thr Pro Gly Ser Tyr Thr Cys Asp Cys Pro Pro Asp
    1505                1510                1515

Phe Glu Leu Asn Pro Thr Arg Val Gly Cys Val Asp Thr Arg Ser
    1520                1525                1530

Gly Asn Cys Tyr Leu Asp Ile Arg Pro Arg Gly Asp Asn Gly Asp
    1535                1540                1545

Thr Ala Cys Ser Asn Glu Ile Gly Val Gly Val Ser Lys Ala Ser
    1550                1555                1560

Cys Cys Cys Ser Leu Gly Lys Ala Trp Gly Thr Pro Cys Glu Leu
    1565                1570                1575

Cys Pro Ser Val Asn Thr Ser Glu Tyr Lys Ile Leu Cys Pro Gly
    1580                1585                1590

Gly Glu Gly Phe Arg Pro Asn Pro Ile Thr Val Ile Leu Glu Asp
    1595                1600                1605

Ile Asp Glu Cys Gln Glu Leu Pro Gly Leu Cys Gln Gly Gly Lys
    1610                1615                1620

Cys Ile Asn Thr Phe Gly Ser Phe Gln Cys Arg Cys Pro Thr Gly
    1625                1630                1635

Tyr Tyr Leu Asn Glu Asp Thr Arg Val Cys Asp Asp Val Asn Glu
    1640                1645                1650

Cys Glu Thr Pro Gly Ile Cys Gly Pro Gly Thr Cys Tyr Asn Thr
    1655                1660                1665

Val Gly Asn Tyr Thr Cys Ile Cys Pro Pro Asp Tyr Met Gln Val
    1670                1675                1680

Asn Gly Gly Asn Asn Cys Met Asp Met Arg Arg Ser Leu Cys Tyr
    1685                1690                1695

Arg Asn Tyr Tyr Ala Asp Asn Gln Thr Cys Asp Gly Glu Leu Leu
    1700                1705                1710

Phe Asn Met Thr Lys Lys Met Cys Cys Cys Ser Tyr Asn Ile Gly
    1715                1720                1725
```

Arg Ala Trp Asn Lys Pro Cys Glu Gln Cys Pro Ile Pro Ser Thr
1730 1735 1740

Asp Glu Phe Ala Thr Leu Cys Gly Ser Gln Arg Pro Gly Phe Val
1745 1750 1755

Ile Asp Ile Tyr Thr Gly Leu Pro Val Asp Ile Asp Glu Cys Arg
1760 1765 1770

Glu Ile Pro Gly Val Cys Glu Asn Gly Val Cys Ile Asn Met Val
1775 1780 1785

Gly Ser Phe Arg Cys Glu Cys Pro Val Gly Phe Phe Tyr Asn Asp
1790 1795 1800

Lys Leu Leu Val Cys Glu Asp Ile Asp Glu Cys Gln Asn Gly Pro
1805 1810 1815

Val Cys Gln Arg Asn Ala Glu Cys Ile Asn Thr Ala Gly Ser Tyr
1820 1825 1830

Arg Cys Asp Cys Lys Pro Gly Tyr Arg Leu Thr Ser Thr Gly Gln
1835 1840 1845

Cys Asn Asp Arg Asn Glu Cys Gln Glu Ile Pro Asn Ile Cys Ser
1850 1855 1860

His Gly Gln Cys Ile Asp Thr Val Gly Ser Phe Tyr Cys Leu Cys
1865 1870 1875

His Thr Gly Phe Lys Thr Asn Val Asp Gln Thr Met Cys Leu Asp
1880 1885 1890

Ile Asn Glu Cys Glu Arg Asp Ala Cys Gly Asn Gly Thr Cys Arg
1895 1900 1905

Asn Thr Ile Gly Ser Phe Asn Cys Arg Cys Asn His Gly Phe Ile
1910 1915 1920

Leu Ser His Asn Asn Asp Cys Ile Asp Val Asp Glu Cys Ala Thr
1925 1930 1935

Gly Asn Gly Asn Leu Cys Arg Asn Gly Gln Cys Val Asn Thr Val
1940 1945 1950

Gly Ser Phe Gln Cys Arg Cys Asn Glu Gly Tyr Glu Val Ala Pro
1955 1960 1965

Asp Gly Arg Thr Cys Val Asp Ile Asn Glu Cys Val Leu Asp Pro
1970 1975 1980

Gly Lys Cys Ala Pro Gly Thr Cys Gln Asn Leu Asp Gly Ser Tyr
1985 1990 1995

Arg Cys Ile Cys Pro Pro Gly Tyr Ser Leu Gln Asn Asp Lys Cys
2000 2005 2010

Glu Asp Ile Asp Glu Cys Val Glu Glu Pro Glu Ile Cys Ala Leu
2015 2020 2025

Gly Thr Cys Ser Asn Thr Glu Gly Ser Phe Lys Cys Leu Cys Pro
2030 2035 2040

Glu Gly Phe Ser Leu Ser Ser Thr Gly Arg Arg Cys Gln Asp Leu
2045 2050 2055

Arg Met Ser Tyr Cys Tyr Ala Lys Phe Glu Gly Gly Lys Cys Ser
2060 2065 2070

Ser Pro Lys Ser Arg Asn His Ser Lys Gln Glu Cys Cys Cys Ala
2075 2080 2085

Leu Lys Gly Glu Gly Trp Gly Asp Pro Cys Glu Leu Cys Pro Thr
2090 2095 2100

Glu Pro Asp Glu Ala Phe Arg Gln Ile Cys Pro Phe Gly Ser Gly
2105 2110 2115

Ile Ile Val Gly Pro Asp Asp Ser Ala Val Asp Met Asp Glu Cys

```
    2120                2125                2130

Lys Glu  Pro Asp Val Cys Arg  His Gly Gln Cys Ile  Asn Thr Asp
    2135                2140                2145

Gly Ser  Tyr Arg Cys Glu Cys  Pro Phe Gly Tyr Ile  Leu Glu Gly
    2150                2155                2160

Asn Glu  Cys Val Asp Thr Asp  Glu Cys Ser Val Gly  Asn Pro Cys
    2165                2170                2175

Gly Asn  Gly Thr Cys Lys Asn  Val Ile Gly Gly Phe  Glu Cys Thr
    2180                2185                2190

Cys Glu  Glu Gly Phe Glu Pro  Gly Pro Met Met Thr  Cys Glu Asp
    2195                2200                2205

Ile Asn  Glu Cys Ala Gln Asn  Pro Leu Leu Cys Ala  Phe Arg Cys
    2210                2215                2220

Val Asn  Thr Tyr Gly Ser Tyr  Glu Cys Lys Cys Pro  Val Gly Tyr
    2225                2230                2235

Val Leu  Arg Glu Asp Arg Arg  Met Cys Lys Asp Glu  Asp Glu Cys
    2240                2245                2250

Ala Glu  Gly Lys His Asp Cys  Thr Glu Lys Gln Met  Glu Cys Lys
    2255                2260                2265

Asn Leu  Ile Gly Thr Tyr Met  Cys Ile Cys Gly Pro  Gly Tyr Gln
    2270                2275                2280

Arg Arg  Pro Asp Gly Glu Gly  Cys Ile Asp Glu Asn  Glu Cys Gln
    2285                2290                2295

Thr Lys  Pro Gly Ile Cys Glu  Asn Gly Arg Cys Leu  Asn Thr Leu
    2300                2305                2310

Gly Ser  Tyr Thr Cys Glu Cys  Asn Asp Gly Phe Thr  Ala Ser Pro
    2315                2320                2325

Thr Gln  Asp Glu Cys Leu Asp  Asn Arg Glu Gly Tyr  Cys Phe Ser
    2330                2335                2340

Glu Val  Leu Gln Asn Met Cys  Gln Ile Gly Ser Ser  Asn Arg Asn
    2345                2350                2355

Pro Val  Thr Lys Ser Glu Cys  Cys Cys Asp Gly Gly  Arg Gly Trp
    2360                2365                2370

Gly Pro  His Cys Glu Ile Cys  Pro Phe Glu Gly Thr  Val Ala Tyr
    2375                2380                2385

Lys Lys  Leu Cys Pro His Gly  Arg Gly Phe Met Thr  Asn Gly Ala
    2390                2395                2400

Asp Ile  Asp Glu Cys Lys Val  Ile His Asp Val Cys  Arg Asn Gly
    2405                2410                2415

Glu Cys  Val Asn Asp Arg Gly  Ser Tyr His Cys Ile  Cys Lys Thr
    2420                2425                2430

Gly Tyr  Thr Pro Asp Ile Thr  Gly Thr Ala Cys Val  Asp Leu Asn
    2435                2440                2445

Glu Cys  Asn Gln Ala Pro Lys  Pro Cys Asn Phe Ile  Cys Lys Asn
    2450                2455                2460

Thr Glu  Gly Ser Tyr Gln Cys  Ser Cys Pro Lys Gly  Tyr Ile Leu
    2465                2470                2475

Gln Glu  Asp Gly Arg Ser Cys  Lys Asp Leu Asp Glu  Cys Ala Thr
    2480                2485                2490

Lys Gln  His Asn Cys Gln Phe  Leu Cys Val Asn Thr  Ile Gly Gly
    2495                2500                2505

Phe Thr  Cys Lys Cys Pro Pro  Gly Phe Thr Gln His  His Thr Ala
    2510                2515                2520
```

Cys Ile Asp Asn Asn Glu Cys Thr Ser Asp Ile Asn Leu Cys Gly
2525 2530 2535

Ser Lys Gly Val Cys Gln Asn Thr Pro Gly Ser Phe Thr Cys Glu
2540 2545 2550

Cys Gln Arg Gly Phe Ser Leu Asp Gln Ser Gly Ala Ser Cys Glu
2555 2560 2565

Asp Val Asp Glu Cys Glu Gly Asn His Arg Cys Gln His Gly Cys
2570 2575 2580

Gln Asn Ile Ile Gly Gly Tyr Arg Cys Ser Cys Pro Gln Gly Tyr
2585 2590 2595

Leu Gln His Tyr Gln Trp Asn Gln Cys Val Asp Glu Asn Glu Cys
2600 2605 2610

Leu Ser Ala His Val Cys Gly Gly Ala Ser Cys His Asn Thr Leu
2615 2620 2625

Gly Ser Tyr Lys Cys Met Cys Pro Thr Gly Phe Gln Tyr Glu Gln
2630 2635 2640

Phe Ser Gly Gly Cys Gln Asp Ile Asn Glu Cys Gly Ser Ser Gln
2645 2650 2655

Ala Pro Cys Ser Tyr Gly Cys Ser Asn Thr Glu Gly Gly Tyr Leu
2660 2665 2670

Cys Gly Cys Pro Pro Gly Tyr Phe Arg Ile Gly Gln Gly His Cys
2675 2680 2685

Val Ser Gly Met Gly Met Gly Arg Gly Gly Pro Glu Pro Pro Ala
2690 2695 2700

Ser Ser Glu Met Asp Asp Asn Ser Leu Ser Pro Glu Ala Cys Tyr
2705 2710 2715

Glu Cys Lys Ile Asn Gly Tyr Pro Lys Arg Gly Arg Lys Arg Arg
2720 2725 2730

Ser Thr Asn Glu Asn
2735

<210> SEQ ID NO 32
<211> LENGTH: 2755
<212> TYPE: PRT
<213> ORGANISM: Artificial Sequence
<220> FEATURE:
<223> OTHER INFORMATION: Synthetic

<400> SEQUENCE: 32

Met Arg Arg Gly Gly Leu Leu Glu Val Ala Leu Ala Phe Ala Leu Leu
1 5 10 15

Leu Glu Ser Tyr Thr Ser His Gly Ala Asp Ala Asn Leu Glu Ala Gly
20 25 30

Ser Leu Lys Glu Thr Arg Ala Asn Arg Ala Lys Arg Arg Gly Gly Gly
35 40 45

Gly His Asp Ala Leu Lys Gly Pro Asn Val Cys Gly Ser Arg Tyr Asn
50 55 60

Ala Tyr Cys Cys Pro Gly Trp Lys Thr Leu Pro Gly Gly Asn Gln Cys
65 70 75 80

Ile Val Pro Ile Cys Arg His Ser Cys Gly Asp Gly Phe Cys Ser Arg
85 90 95

Pro Asn Met Cys Thr Cys Pro Ser Gly Gln Ile Ser Pro Ser Cys Gly
100 105 110

Ser Arg Ser Ile Gln His Cys Ser Ile Arg Cys Met Asn Gly Gly Ser
115 120 125

```
Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
        275                 280                 285

Ile Asp Glu Cys Ser Thr Ile Pro Gly Val Cys Asp Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
        355                 360                 365

Gly Val Thr Val Ala Pro Glu Met Cys Pro Ile Arg Ser Thr Glu Asp
    370                 375                 380

Phe Asn Lys Leu Cys Ser Val Pro Leu Val Ile Pro Gly Arg Pro Glu
385                 390                 395                 400

Tyr Pro Pro Pro Pro Ile Gly Pro Leu Pro Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
        435                 440                 445

Phe Asn Val Thr Asp Tyr Cys Gln Leu Val Arg Tyr Leu Cys Gln Asn
    450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
            500                 505                 510

Tyr Thr Cys His Cys Arg Ala Gly Tyr Gln Ser Thr Leu Thr Arg Thr
        515                 520                 525

Glu Cys Arg Asp Ile Asp Glu Cys Leu Gln Asn Gly Arg Ile Cys Asn
    530                 535                 540
```

-continued

```
Asn Gly Arg Cys Ile Asn Thr Asp Gly Ser Phe His Cys Val Cys Asn
545                 550                 555                 560

Ala Gly Phe His Val Thr Arg Asp Gly Lys Asn Cys Glu Asp Met Asp
                565                 570                 575

Glu Cys Ser Ile Arg Asn Met Cys Leu Asn Gly Met Cys Ile Asn Glu
            580                 585                 590

Asp Gly Ser Phe Lys Cys Ile Cys Lys Pro Gly Phe Gln Leu Ala Ser
        595                 600                 605

Asp Gly Arg Tyr Cys Lys Asp Ile Asn Glu Cys Glu Thr Pro Gly Ile
    610                 615                 620

Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
                645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
        675                 680                 685

Ser Thr Glu Tyr Ala Phe Gly Glu Pro Cys Gln Pro Cys Pro Ala Gln
    690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
                725                 730                 735

Pro Asn Gly Ile Cys Glu Asn Leu Arg Gly Thr Tyr Lys Cys Ile Cys
            740                 745                 750

Asn Ser Gly Tyr Glu Val Asp Ile Thr Gly Lys Asn Cys Val Asp Ile
        755                 760                 765

Asn Glu Cys Val Leu Asn Ser Leu Leu Cys Asp Asn Gly Gln Cys Arg
    770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
                805                 810                 815

Pro Cys Ile Asn Gly Val Cys Lys Asn Ser Pro Gly Ser Phe Ile Cys
            820                 825                 830

Glu Cys Ser Pro Glu Ser Thr Leu Asp Pro Thr Lys Thr Ile Cys Ile
        835                 840                 845

Glu Thr Ile Lys Gly Thr Cys Trp Gln Thr Val Ile Asp Gly Arg Cys
    850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
                885                 890                 895

Ile Cys Gly Lys Gly Phe Ser Arg Ile Lys Gly Thr Gln Cys Glu Asp
            900                 905                 910

Ile Asn Glu Cys Glu Val Phe Pro Gly Val Cys Lys Asn Gly Leu Cys
        915                 920                 925

Val Asn Ser Arg Gly Ser Phe Lys Cys Glu Cys Pro Asn Gly Met Thr
    930                 935                 940

Leu Asp Ala Thr Gly Arg Ile Cys Leu Asp Ile Arg Leu Glu Thr Cys
945                 950                 955                 960

Phe Leu Lys Tyr Asp Asp Glu Glu Cys Thr Leu Pro Ile Ala Gly Arg
```

```
                965                 970                 975

His Arg Met Asp Ala Cys Cys Cys Ser Val Gly Ala Ala Trp Gly Thr
            980                 985                 990

Glu Glu Cys Glu Glu Cys Pro Leu  Arg Asn Ser Arg Glu  Tyr Glu Glu
        995                 1000                1005

Leu Cys  Pro Arg Gly Pro Gly  Phe Ala Thr Lys Asp  Ile Thr Asn
    1010                 1015                 1020

Gly Lys  Pro Phe Phe Lys Asp  Ile Asn Glu Cys Lys  Met Ile Pro
    1025                 1030                 1035

Ser Leu  Cys Thr His Gly Lys  Cys Arg Asn Thr Ile  Gly Ser Phe
    1040                 1045                 1050

Lys Cys  Arg Cys Asp Ser Gly  Phe Ala Leu Asp Ser  Glu Glu Arg
    1055                 1060                 1065

Asn Cys  Thr Asp Ile Asp Glu  Cys Arg Ile Ser Pro  Asp Leu Cys
    1070                 1075                 1080

Gly Arg  Gly Gln Cys Val Asn  Thr Pro Gly Asp Phe  Glu Cys Lys
    1085                 1090                 1095

Cys Asp  Glu Gly Tyr Glu Ser  Gly Phe Met Met Met  Lys Asn Cys
    1100                 1105                 1110

Met Asp  Ile Asp Glu Cys Gln  Arg Asp Pro Leu Leu  Cys Arg Gly
    1115                 1120                 1125

Gly Ile  Cys His Asn Thr Glu  Gly Ser Tyr Arg Cys  Glu Cys Pro
    1130                 1135                 1140

Pro Gly  His Gln Leu Ser Pro  Asn Ile Ser Ala Cys  Ile Asp Ile
    1145                 1150                 1155

Asn Glu  Cys Glu Leu Ser Ala  Asn Leu Cys Pro His  Gly Arg Cys
    1160                 1165                 1170

Val Asn  Leu Ile Gly Lys Tyr  Gln Cys Ala Cys Asn  Pro Gly Tyr
    1175                 1180                 1185

His Pro  Thr His Asp Arg Leu  Phe Cys Val Asp Ile  Asp Glu Cys
    1190                 1195                 1200

Ser Ile  Met Asn Gly Gly Cys  Glu Thr Phe Cys Thr  Asn Ser Asp
    1205                 1210                 1215

Gly Ser  Tyr Glu Cys Ser Cys  Gln Pro Gly Phe Ala  Leu Met Pro
    1220                 1225                 1230

Asp Gln  Arg Ser Cys Thr Asp  Ile Asp Glu Cys Glu  Asp Asn Pro
    1235                 1240                 1245

Asn Ile  Cys Asp Gly Gly Gln  Cys Thr Asn Ile Pro  Gly Glu Tyr
    1250                 1255                 1260

Arg Cys  Leu Cys Tyr Asp Gly  Phe Met Ala Ser Glu  Asp Met Lys
    1265                 1270                 1275

Thr Cys  Val Asp Val Asn Glu  Cys Asp Leu Asn Pro  Asn Ile Cys
    1280                 1285                 1290

Leu Ser  Gly Thr Cys Glu Asn  Thr Lys Gly Ser Phe  Ile Cys His
    1295                 1300                 1305

Cys Asp  Met Gly Tyr Ser Gly  Lys Lys Gly Lys Thr  Gly Cys Thr
    1310                 1315                 1320

Asp Ile  Asn Glu Cys Glu Ile  Gly Ala His Asn Cys  Gly Arg His
    1325                 1330                 1335

Ala Val  Cys Thr Asn Thr Ala  Gly Ser Phe Lys Cys  Ser Cys Ser
    1340                 1345                 1350

Pro Gly  Trp Ile Gly Asp Gly  Ile Lys Cys Thr Asp  Leu Asp Glu
    1355                 1360                 1365
```

-continued

```
Cys Ser  Asn Gly Thr His Met  Cys Ser Gln His Ala  Asp Cys Lys
    1370                 1375                 1380

Asn Thr  Met Gly Ser Tyr Arg  Cys Leu Cys Lys Asp  Gly Tyr Thr
    1385                 1390                 1395

Gly Asp  Gly Phe Thr Cys Thr  Asp Leu Asp Glu Cys  Ser Glu Asn
    1400                 1405                 1410

Leu Asn  Leu Cys Gly Asn Gly  Gln Cys Leu Asn Ala  Pro Gly Gly
    1415                 1420                 1425

Tyr Arg  Cys Glu Cys Asp Met  Gly Phe Val Pro Ser  Ala Asp Gly
    1430                 1435                 1440

Lys Ala  Cys Glu Asp Ile Asp  Glu Cys Ser Leu Pro  Asn Ile Cys
    1445                 1450                 1455

Val Phe  Gly Thr Cys His Asn  Leu Pro Gly Leu Phe  Arg Cys Glu
    1460                 1465                 1470

Cys Glu  Ile Gly Tyr Glu Leu  Asp Arg Ser Gly Gly  Asn Cys Thr
    1475                 1480                 1485

Asp Val  Asn Glu Cys Leu Asp  Pro Thr Thr Cys Ile  Ser Gly Asn
    1490                 1495                 1500

Cys Val  Asn Thr Pro Gly Ser  Tyr Thr Cys Asp Cys  Pro Pro Asp
    1505                 1510                 1515

Phe Glu  Leu Asn Pro Thr Arg  Val Gly Cys Val Asp  Thr Arg Ser
    1520                 1525                 1530

Gly Asn  Cys Tyr Leu Asp Ile  Arg Pro Arg Gly Asp  Asn Gly Asp
    1535                 1540                 1545

Thr Ala  Cys Ser Asn Glu Ile  Gly Val Gly Val Ser  Lys Ala Ser
    1550                 1555                 1560

Cys Cys  Cys Ser Leu Gly Lys  Ala Trp Gly Thr Pro  Cys Glu Leu
    1565                 1570                 1575

Cys Pro  Ser Val Asn Thr Ser  Glu Tyr Lys Ile Leu  Cys Pro Gly
    1580                 1585                 1590

Gly Glu  Gly Phe Arg Pro Asn  Pro Ile Thr Val Ile  Leu Glu Asp
    1595                 1600                 1605

Ile Asp  Glu Cys Gln Glu Leu  Pro Gly Leu Cys Gln  Gly Gly Lys
    1610                 1615                 1620

Cys Ile  Asn Thr Phe Gly Ser  Phe Gln Cys Arg Cys  Pro Thr Gly
    1625                 1630                 1635

Tyr Tyr  Leu Asn Glu Asp Thr  Arg Val Cys Asp Asp  Val Asn Glu
    1640                 1645                 1650

Cys Glu  Thr Pro Gly Ile Cys  Gly Pro Gly Thr Cys  Tyr Asn Thr
    1655                 1660                 1665

Val Gly  Asn Tyr Thr Cys Ile  Cys Pro Pro Asp Tyr  Met Gln Val
    1670                 1675                 1680

Asn Gly  Gly Asn Asn Cys Met  Asp Met Arg Arg Ser  Leu Cys Tyr
    1685                 1690                 1695

Arg Asn  Tyr Tyr Ala Asp Asn  Gln Thr Cys Asp Gly  Glu Leu Leu
    1700                 1705                 1710

Phe Asn  Met Thr Lys Lys Met  Cys Cys Cys Ser Tyr  Asn Ile Gly
    1715                 1720                 1725

Arg Ala  Trp Asn Lys Pro Cys  Glu Gln Cys Pro Ile  Pro Ser Thr
    1730                 1735                 1740

Asp Glu  Phe Ala Thr Leu Cys  Gly Ser Gln Arg Pro  Gly Phe Val
    1745                 1750                 1755
```

```
Ile Asp Ile Tyr Thr Gly Leu Pro Val Asp Ile Asp Glu Cys Arg
    1760                1765                1770

Glu Ile Pro Gly Val Cys Glu Asn Gly Val Cys Ile Asn Met Val
    1775                1780                1785

Gly Ser Phe Arg Cys Glu Cys Pro Val Gly Phe Phe Tyr Asn Asp
    1790                1795                1800

Lys Leu Leu Val Cys Glu Asp Ile Asp Glu Cys Gln Asn Gly Pro
    1805                1810                1815

Val Cys Gln Arg Asn Ala Glu Cys Ile Asn Thr Ala Gly Ser Tyr
    1820                1825                1830

Arg Cys Asp Cys Lys Pro Gly Tyr Arg Leu Thr Ser Thr Gly Gln
    1835                1840                1845

Cys Asn Asp Arg Asn Glu Cys Gln Glu Ile Pro Asn Ile Cys Ser
    1850                1855                1860

His Gly Gln Cys Ile Asp Thr Val Gly Ser Phe Tyr Cys Leu Cys
    1865                1870                1875

His Thr Gly Phe Lys Thr Asn Val Asp Gln Thr Met Cys Leu Asp
    1880                1885                1890

Ile Asn Glu Cys Glu Arg Asp Ala Cys Gly Asn Gly Thr Cys Arg
    1895                1900                1905

Asn Thr Ile Gly Ser Phe Asn Cys Arg Cys Asn His Gly Phe Ile
    1910                1915                1920

Leu Ser His Asn Asn Asp Cys Ile Asp Val Asp Glu Cys Ala Thr
    1925                1930                1935

Gly Asn Gly Asn Leu Cys Arg Asn Gly Gln Cys Val Asn Thr Val
    1940                1945                1950

Gly Ser Phe Gln Cys Arg Cys Asn Glu Gly Tyr Glu Val Ala Pro
    1955                1960                1965

Asp Gly Arg Thr Cys Val Asp Ile Asn Glu Cys Val Leu Asp Pro
    1970                1975                1980

Gly Lys Cys Ala Pro Gly Thr Cys Gln Asn Leu Asp Gly Ser Tyr
    1985                1990                1995

Arg Cys Ile Cys Pro Pro Gly Tyr Ser Leu Gln Asn Asp Lys Cys
    2000                2005                2010

Glu Asp Ile Asp Glu Cys Val Glu Glu Pro Glu Ile Cys Ala Leu
    2015                2020                2025

Gly Thr Cys Ser Asn Thr Glu Gly Ser Phe Lys Cys Leu Cys Pro
    2030                2035                2040

Glu Gly Phe Ser Leu Ser Ser Thr Gly Arg Arg Cys Gln Asp Leu
    2045                2050                2055

Arg Met Ser Tyr Cys Tyr Ala Lys Phe Glu Gly Gly Lys Cys Ser
    2060                2065                2070

Ser Pro Lys Ser Arg Asn His Ser Lys Gln Glu Cys Cys Cys Ala
    2075                2080                2085

Leu Lys Gly Glu Gly Trp Gly Asp Pro Cys Glu Leu Cys Pro Thr
    2090                2095                2100

Glu Pro Asp Glu Ala Phe Arg Gln Ile Cys Pro Phe Gly Ser Gly
    2105                2110                2115

Ile Ile Val Gly Pro Asp Asp Ser Ala Val Asp Met Asp Glu Cys
    2120                2125                2130

Lys Glu Pro Asp Val Cys Arg His Gly Gln Cys Ile Asn Thr Asp
    2135                2140                2145

Gly Ser Tyr Arg Cys Glu Cys Pro Phe Gly Tyr Ile Leu Glu Gly
```

```
    2150                2155                2160

Asn Glu  Cys Val Asp Thr Asp  Glu Cys Ser Val Gly  Asn Pro Cys
    2165                2170                2175

Gly Asn  Gly Thr Cys Lys Asn  Val Ile Gly Gly Phe  Glu Cys Thr
    2180                2185                2190

Cys Glu  Glu Gly Phe Glu Pro  Gly Pro Met Met Thr  Cys Glu Asp
    2195                2200                2205

Ile Asn  Glu Cys Ala Gln Asn  Pro Leu Leu Cys Ala  Phe Arg Cys
    2210                2215                2220

Val Asn  Thr Tyr Gly Ser Tyr  Glu Cys Lys Cys Pro  Val Gly Tyr
    2225                2230                2235

Val Leu  Arg Glu Asp Arg Arg  Met Cys Lys Asp Glu  Asp Glu Cys
    2240                2245                2250

Ala Glu  Gly Lys His Asp Cys  Thr Glu Lys Gln Met  Glu Cys Lys
    2255                2260                2265

Asn Leu  Ile Gly Thr Tyr Met  Cys Ile Cys Gly Pro  Gly Tyr Gln
    2270                2275                2280

Arg Arg  Pro Asp Gly Glu Gly  Cys Ile Asp Glu Asn  Glu Cys Gln
    2285                2290                2295

Thr Lys  Pro Gly Ile Cys Glu  Asn Gly Arg Cys Leu  Asn Thr Leu
    2300                2305                2310

Gly Ser  Tyr Thr Cys Glu Cys  Asn Asp Gly Phe Thr  Ala Ser Pro
    2315                2320                2325

Thr Gln  Asp Glu Cys Leu Asp  Asn Arg Glu Gly Tyr  Cys Phe Ser
    2330                2335                2340

Glu Val  Leu Gln Asn Met Cys  Gln Ile Gly Ser Ser  Asn Arg Asn
    2345                2350                2355

Pro Val  Thr Lys Ser Glu Cys  Cys Cys Asp Gly Gly  Arg Gly Trp
    2360                2365                2370

Gly Pro  His Cys Glu Ile Cys  Pro Phe Glu Gly Thr  Val Ala Tyr
    2375                2380                2385

Lys Lys  Leu Cys Pro His Gly  Arg Gly Phe Met Thr  Asn Gly Ala
    2390                2395                2400

Asp Ile  Asp Glu Cys Lys Val  Ile His Asp Val Cys  Arg Asn Gly
    2405                2410                2415

Glu Cys  Val Asn Asp Arg Gly  Ser Tyr His Cys Ile  Cys Lys Thr
    2420                2425                2430

Gly Tyr  Thr Pro Asp Ile Thr  Gly Thr Ala Cys Val  Asp Leu Asn
    2435                2440                2445

Glu Cys  Asn Gln Ala Pro Lys  Pro Cys Asn Phe Ile  Cys Lys Asn
    2450                2455                2460

Thr Glu  Gly Ser Tyr Gln Cys  Ser Cys Pro Lys Gly  Tyr Ile Leu
    2465                2470                2475

Gln Glu  Asp Gly Arg Ser Cys  Lys Asp Leu Asp Glu  Cys Ala Thr
    2480                2485                2490

Lys Gln  His Asn Cys Gln Phe  Leu Cys Val Asn Thr  Ile Gly Gly
    2495                2500                2505

Phe Thr  Cys Lys Cys Pro Pro  Gly Phe Thr Gln His  His Thr Ala
    2510                2515                2520

Cys Ile  Asp Asn Asn Glu Cys  Thr Ser Asp Ile Asn  Leu Cys Gly
    2525                2530                2535

Ser Lys  Gly Val Cys Gln Asn  Thr Pro Gly Ser Phe  Thr Cys Glu
    2540                2545                2550
```

Cys Gln Arg Gly Phe Ser Leu Asp Gln Ser Gly Ala Ser Cys Glu
2555 2560 2565

Asp Val Asp Glu Cys Glu Gly Asn His Arg Cys Gln His Gly Cys
2570 2575 2580

Gln Asn Ile Ile Gly Gly Tyr Arg Cys Ser Cys Pro Gln Gly Tyr
2585 2590 2595

Leu Gln His Tyr Gln Trp Asn Gln Cys Val Asp Glu Asn Glu Cys
2600 2605 2610

Leu Ser Ala His Val Cys Gly Gly Ala Ser Cys His Asn Thr Leu
2615 2620 2625

Gly Ser Tyr Lys Cys Met Cys Pro Thr Gly Phe Gln Tyr Glu Gln
2630 2635 2640

Phe Ser Gly Gly Cys Gln Asp Ile Asn Glu Cys Gly Ser Ser Gln
2645 2650 2655

Ala Pro Cys Ser Tyr Gly Cys Ser Asn Thr Glu Gly Gly Tyr Leu
2660 2665 2670

Cys Gly Cys Pro Pro Gly Tyr Phe Arg Ile Gly Gln Gly His Cys
2675 2680 2685

Val Ser Gly Met Gly Met Gly Arg Gly Gly Pro Glu Pro Pro Ala
2690 2695 2700

Ser Ser Glu Met Asp Asp Asn Ser Leu Ser Pro Glu Ala Cys Tyr
2705 2710 2715

Glu Cys Lys Ile Asn Gly Tyr Pro Lys Ala Ala Gln Ser His Leu
2720 2725 2730

Pro Ala Thr Arg Pro Glu Thr Glu Lys His Glu Arg Asn Gly Cys
2735 2740 2745

Leu Arg His Pro Gly Arg Val
2750 2755

<210> SEQ ID NO 33
<211> LENGTH: 2737
<212> TYPE: PRT
<213> ORGANISM: Artificial Sequence
<220> FEATURE:
<223> OTHER INFORMATION: Synthetic

<400> SEQUENCE: 33

Met Arg Arg Gly Gly Leu Leu Glu Val Ala Leu Ala Phe Ala Leu Leu
1 5 10 15

Leu Glu Ser Tyr Thr Ser His Gly Ala Asp Ala Asn Leu Glu Ala Gly
20 25 30

Ser Leu Lys Glu Thr Arg Ala Asn Arg Ala Lys Arg Arg Gly Gly Gly
35 40 45

Gly His Asp Ala Leu Lys Gly Pro Asn Val Cys Gly Ser Arg Tyr Asn
50 55 60

Ala Tyr Cys Cys Pro Gly Trp Lys Thr Leu Pro Gly Gly Asn Gln Cys
65 70 75 80

Ile Val Pro Ile Cys Arg His Ser Cys Gly Asp Gly Phe Cys Ser Arg
85 90 95

Pro Asn Met Cys Thr Cys Pro Ser Gly Gln Ile Ser Pro Ser Cys Gly
100 105 110

Ser Arg Ser Ile Gln His Cys Ser Ile Arg Cys Met Asn Gly Gly Ser
115 120 125

Cys Ser Asp Asp His Cys Leu Cys Gln Lys Gly Tyr Ile Gly Thr His
130 135 140

-continued

```
Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
        275                 280                 285

Ile Asp Glu Cys Ser Thr Ile Pro Gly Val Cys Asp Gly Gly Glu Cys
    290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
        355                 360                 365

Gly Val Thr Val Ala Pro Glu Met Cys Pro Ile Arg Ser Thr Glu Asp
    370                 375                 380

Phe Asn Lys Leu Cys Ser Val Pro Leu Val Ile Pro Gly Arg Pro Glu
385                 390                 395                 400

Tyr Pro Pro Pro Pro Ile Gly Pro Leu Pro Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
        435                 440                 445

Phe Asn Val Thr Asp Tyr Cys Gln Leu Val Arg Tyr Leu Cys Gln Asn
    450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
            500                 505                 510

Tyr Thr Cys His Cys Arg Ala Gly Tyr Gln Ser Thr Leu Thr Arg Thr
        515                 520                 525

Glu Cys Arg Asp Ile Asp Glu Cys Leu Gln Asn Gly Arg Ile Cys Asn
    530                 535                 540

Asn Gly Arg Cys Ile Asn Thr Asp Gly Ser Phe His Cys Val Cys Asn
545                 550                 555                 560
```

-continued

```
Ala Gly Phe His Val Thr Arg Asp Gly Lys Asn Cys Glu Asp Met Asp
                565                 570                 575

Glu Cys Ser Ile Arg Asn Met Cys Leu Asn Gly Met Cys Ile Asn Glu
            580                 585                 590

Asp Gly Ser Phe Lys Cys Ile Cys Lys Pro Gly Phe Gln Leu Ala Ser
        595                 600                 605

Asp Gly Arg Tyr Cys Lys Asp Ile Asn Glu Cys Glu Thr Pro Gly Ile
    610                 615                 620

Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
                645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
        675                 680                 685

Ser Thr Glu Tyr Ala Phe Gly Glu Pro Cys Gln Pro Cys Pro Ala Gln
    690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
                725                 730                 735

Pro Asn Gly Ile Cys Glu Asn Leu Arg Gly Thr Tyr Lys Cys Ile Cys
            740                 745                 750

Asn Ser Gly Tyr Glu Val Asp Ile Thr Gly Lys Asn Cys Val Asp Ile
        755                 760                 765

Asn Glu Cys Val Leu Asn Ser Leu Leu Cys Asp Asn Gly Gln Cys Arg
    770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
                805                 810                 815

Pro Cys Ile Asn Gly Val Cys Lys Asn Ser Pro Gly Ser Phe Ile Cys
            820                 825                 830

Glu Cys Ser Pro Glu Ser Thr Leu Asp Pro Thr Lys Thr Ile Cys Ile
        835                 840                 845

Glu Thr Ile Lys Gly Thr Cys Trp Gln Thr Val Ile Asp Gly Arg Cys
    850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
                885                 890                 895

Ile Cys Gly Lys Gly Phe Ser Arg Ile Lys Gly Thr Gln Cys Glu Asp
            900                 905                 910

Ile Asn Glu Cys Glu Val Phe Pro Gly Val Cys Lys Asn Gly Leu Cys
        915                 920                 925

Val Asn Ser Arg Gly Ser Phe Lys Cys Glu Cys Pro Asn Gly Met Thr
    930                 935                 940

Leu Asp Ala Thr Gly Arg Ile Cys Leu Asp Ile Arg Leu Glu Thr Cys
945                 950                 955                 960

Phe Leu Lys Tyr Asp Asp Glu Glu Cys Thr Leu Pro Ile Ala Gly Arg
                965                 970                 975

His Arg Met Asp Ala Cys Cys Cys Ser Val Gly Ala Ala Trp Gly Thr
```

-continued

```
            980                 985                 990

Glu Glu Cys Glu Glu Cys Pro Leu  Arg Asn Ser Arg Glu  Tyr Glu Glu
        995                 1000                1005

Leu Cys  Pro Arg Gly Pro Gly  Phe Ala Thr Lys Asp  Ile Thr Asn
    1010                 1015                 1020

Gly Lys  Pro Phe Phe Lys Asp  Ile Asn Glu Cys Lys  Met Ile Pro
    1025                 1030                 1035

Ser Leu  Cys Thr His Gly Lys  Cys Arg Asn Thr Ile  Gly Ser Phe
    1040                 1045                 1050

Lys Cys  Arg Cys Asp Ser Gly  Phe Ala Leu Asp Ser  Glu Glu Arg
    1055                 1060                 1065

Asn Cys  Thr Asp Ile Asp Glu  Cys Arg Ile Ser Pro  Asp Leu Cys
    1070                 1075                 1080

Gly Arg  Gly Gln Cys Val Asn  Thr Pro Gly Asp Phe  Glu Cys Lys
    1085                 1090                 1095

Cys Asp  Glu Gly Tyr Glu Ser  Gly Phe Met Met Met  Lys Asn Cys
    1100                 1105                 1110

Met Asp  Ile Asp Glu Cys Gln  Arg Asp Pro Leu Leu  Cys Arg Gly
    1115                 1120                 1125

Gly Ile  Cys His Asn Thr Glu  Gly Ser Tyr Arg Cys  Glu Cys Pro
    1130                 1135                 1140

Pro Gly  His Gln Leu Ser Pro  Asn Ile Ser Ala Cys  Ile Asp Ile
    1145                 1150                 1155

Asn Glu  Cys Glu Leu Ser Ala  Asn Leu Cys Pro His  Gly Arg Cys
    1160                 1165                 1170

Val Asn  Leu Ile Gly Lys Tyr  Gln Cys Ala Cys Asn  Pro Gly Tyr
    1175                 1180                 1185

His Pro  Thr His Asp Arg Leu  Phe Cys Val Asp Ile  Asp Glu Cys
    1190                 1195                 1200

Ser Ile  Met Asn Gly Gly Cys  Glu Thr Phe Cys Thr  Asn Ser Asp
    1205                 1210                 1215

Gly Ser  Tyr Glu Cys Ser Cys  Gln Pro Gly Phe Ala  Leu Met Pro
    1220                 1225                 1230

Asp Gln  Arg Ser Cys Thr Asp  Ile Asp Glu Cys Glu  Asp Asn Pro
    1235                 1240                 1245

Asn Ile  Cys Asp Gly Gly Gln  Cys Thr Asn Ile Pro  Gly Glu Tyr
    1250                 1255                 1260

Arg Cys  Leu Cys Tyr Asp Gly  Phe Met Ala Ser Glu  Asp Met Lys
    1265                 1270                 1275

Thr Cys  Val Asp Val Asn Glu  Cys Asp Leu Asn Pro  Asn Ile Cys
    1280                 1285                 1290

Leu Ser  Gly Thr Cys Glu Asn  Thr Lys Gly Ser Phe  Ile Cys His
    1295                 1300                 1305

Cys Asp  Met Gly Tyr Ser Gly  Lys Lys Gly Lys Thr  Gly Cys Thr
    1310                 1315                 1320

Asp Ile  Asn Glu Cys Glu Ile  Gly Ala His Asn Cys  Gly Arg His
    1325                 1330                 1335

Ala Val  Cys Thr Asn Thr Ala  Gly Ser Phe Lys Cys  Ser Cys Ser
    1340                 1345                 1350

Pro Gly  Trp Ile Gly Asp Gly  Ile Lys Cys Thr Asp  Leu Asp Glu
    1355                 1360                 1365

Cys Ser  Asn Gly Thr His Met  Cys Ser Gln His Ala  Asp Cys Lys
    1370                 1375                 1380
```

-continued

```
Asn Thr Met Gly Ser Tyr Arg Cys Leu Cys Lys Asp Gly Tyr Thr
    1385                1390                1395

Gly Asp Gly Phe Thr Cys Thr Asp Leu Asp Glu Cys Ser Glu Asn
    1400                1405                1410

Leu Asn Leu Cys Gly Asn Gly Gln Cys Leu Asn Ala Pro Gly Gly
    1415                1420                1425

Tyr Arg Cys Glu Cys Asp Met Gly Phe Val Pro Ser Ala Asp Gly
    1430                1435                1440

Lys Ala Cys Glu Asp Ile Asp Glu Cys Ser Leu Pro Asn Ile Cys
    1445                1450                1455

Val Phe Gly Thr Cys His Asn Leu Pro Gly Leu Phe Arg Cys Glu
    1460                1465                1470

Cys Glu Ile Gly Tyr Glu Leu Asp Arg Ser Gly Gly Asn Cys Thr
    1475                1480                1485

Asp Val Asn Glu Cys Leu Asp Pro Thr Thr Cys Ile Ser Gly Asn
    1490                1495                1500

Cys Val Asn Thr Pro Gly Ser Tyr Thr Cys Asp Cys Pro Pro Asp
    1505                1510                1515

Phe Glu Leu Asn Pro Thr Arg Val Gly Cys Val Asp Thr Arg Ser
    1520                1525                1530

Gly Asn Cys Tyr Leu Asp Ile Arg Pro Arg Gly Asp Asn Gly Asp
    1535                1540                1545

Thr Ala Cys Ser Asn Glu Ile Gly Val Gly Val Ser Lys Ala Ser
    1550                1555                1560

Cys Cys Cys Ser Leu Gly Lys Ala Trp Gly Thr Pro Cys Glu Leu
    1565                1570                1575

Cys Pro Ser Val Asn Thr Ser Glu Tyr Lys Ile Leu Cys Pro Gly
    1580                1585                1590

Gly Glu Gly Phe Arg Pro Asn Pro Ile Thr Val Ile Leu Glu Asp
    1595                1600                1605

Ile Asp Glu Cys Gln Glu Leu Pro Gly Leu Cys Gln Gly Gly Lys
    1610                1615                1620

Cys Ile Asn Thr Phe Gly Ser Phe Gln Cys Arg Cys Pro Thr Gly
    1625                1630                1635

Tyr Tyr Leu Asn Glu Asp Thr Arg Val Cys Asp Asp Val Asn Glu
    1640                1645                1650

Cys Glu Thr Pro Gly Ile Cys Gly Pro Gly Thr Cys Tyr Asn Thr
    1655                1660                1665

Val Gly Asn Tyr Thr Cys Ile Cys Pro Pro Asp Tyr Met Gln Val
    1670                1675                1680

Asn Gly Gly Asn Asn Cys Met Asp Met Arg Arg Ser Leu Cys Tyr
    1685                1690                1695

Arg Asn Tyr Tyr Ala Asp Asn Gln Thr Cys Asp Gly Glu Leu Leu
    1700                1705                1710

Phe Asn Met Thr Lys Lys Met Cys Cys Cys Ser Tyr Asn Ile Gly
    1715                1720                1725

Arg Ala Trp Asn Lys Pro Cys Glu Gln Cys Pro Ile Pro Ser Thr
    1730                1735                1740

Asp Glu Phe Ala Thr Leu Cys Gly Ser Gln Arg Pro Gly Phe Val
    1745                1750                1755

Ile Asp Ile Tyr Thr Gly Leu Pro Val Asp Ile Asp Glu Cys Arg
    1760                1765                1770
```

-continued

```
Glu Ile  Pro Gly Val Cys Glu  Asn Gly Val Cys Ile  Asn Met Val
    1775                 1780                 1785

Gly Ser  Phe Arg Cys Glu Cys  Pro Val Gly Phe Phe  Tyr Asn Asp
    1790                 1795                 1800

Lys Leu  Leu Val Cys Glu Asp  Ile Asp Glu Cys Gln  Asn Gly Pro
    1805                 1810                 1815

Val Cys  Gln Arg Asn Ala Glu  Cys Ile Asn Thr Ala  Gly Ser Tyr
    1820                 1825                 1830

Arg Cys  Asp Cys Lys Pro Gly  Tyr Arg Leu Thr Ser  Thr Gly Gln
    1835                 1840                 1845

Cys Asn  Asp Arg Asn Glu Cys  Gln Glu Ile Pro Asn  Ile Cys Ser
    1850                 1855                 1860

His Gly  Gln Cys Ile Asp Thr  Val Gly Ser Phe Tyr  Cys Leu Cys
    1865                 1870                 1875

His Thr  Gly Phe Lys Thr Asn  Val Asp Gln Thr Met  Cys Leu Asp
    1880                 1885                 1890

Ile Asn  Glu Cys Glu Arg Asp  Ala Cys Gly Asn Gly  Thr Cys Arg
    1895                 1900                 1905

Asn Thr  Ile Gly Ser Phe Asn  Cys Arg Cys Asn His  Gly Phe Ile
    1910                 1915                 1920

Leu Ser  His Asn Asn Asp Cys  Ile Asp Val Asp Glu  Cys Ala Thr
    1925                 1930                 1935

Gly Asn  Gly Asn Leu Cys Arg  Asn Gly Gln Cys Val  Asn Thr Val
    1940                 1945                 1950

Gly Ser  Phe Gln Cys Arg Cys  Asn Glu Gly Tyr Glu  Val Ala Pro
    1955                 1960                 1965

Asp Gly  Arg Thr Cys Val Asp  Ile Asn Glu Cys Val  Leu Asp Pro
    1970                 1975                 1980

Gly Lys  Cys Ala Pro Gly Thr  Cys Gln Asn Leu Asp  Gly Ser Tyr
    1985                 1990                 1995

Arg Cys  Ile Cys Pro Pro Gly  Tyr Ser Leu Gln Asn  Asp Lys Cys
    2000                 2005                 2010

Glu Asp  Ile Asp Glu Cys Val  Glu Glu Pro Glu Ile  Cys Ala Leu
    2015                 2020                 2025

Gly Thr  Cys Ser Asn Thr Glu  Gly Ser Phe Lys Cys  Leu Cys Pro
    2030                 2035                 2040

Glu Gly  Phe Ser Leu Ser Ser  Thr Gly Arg Arg Cys  Gln Asp Leu
    2045                 2050                 2055

Arg Met  Ser Tyr Cys Tyr Ala  Lys Phe Glu Gly Gly  Lys Cys Ser
    2060                 2065                 2070

Ser Pro  Lys Ser Arg Asn His  Ser Lys Gln Glu Cys  Cys Cys Ala
    2075                 2080                 2085

Leu Lys  Gly Glu Gly Trp Gly  Asp Pro Cys Glu Leu  Cys Pro Thr
    2090                 2095                 2100

Glu Pro  Asp Glu Ala Phe Arg  Gln Ile Cys Pro Phe  Gly Ser Gly
    2105                 2110                 2115

Ile Ile  Val Gly Pro Asp Asp  Ser Ala Val Asp Met  Asp Glu Cys
    2120                 2125                 2130

Lys Glu  Pro Asp Val Cys Arg  His Gly Gln Cys Ile  Asn Thr Asp
    2135                 2140                 2145

Gly Ser  Tyr Arg Cys Glu Cys  Pro Phe Gly Tyr Ile  Leu Glu Gly
    2150                 2155                 2160

Asn Glu  Cys Val Asp Thr Asp  Glu Cys Ser Val Gly  Asn Pro Cys
```

-continued

```
    2165                2170                2175

Gly Asn  Gly Thr Cys Lys Asn  Val Ile Gly Gly Phe  Glu Cys Thr
    2180                2185                2190

Cys Glu  Glu Gly Phe Glu Pro  Gly Pro Met Met Thr  Cys Glu Asp
    2195                2200                2205

Ile Asn  Glu Cys Ala Gln Asn  Pro Leu Leu Cys Ala  Phe Arg Cys
    2210                2215                2220

Val Asn  Thr Tyr Gly Ser Tyr  Glu Cys Lys Cys Pro  Val Gly Tyr
    2225                2230                2235

Val Leu  Arg Glu Asp Arg Arg  Met Cys Lys Asp Glu  Asp Glu Cys
    2240                2245                2250

Ala Glu  Gly Lys His Asp Cys  Thr Glu Lys Gln Met  Glu Cys Lys
    2255                2260                2265

Asn Leu  Ile Gly Thr Tyr Met  Cys Ile Cys Gly Pro  Gly Tyr Gln
    2270                2275                2280

Arg Arg  Pro Asp Gly Glu Gly  Cys Ile Asp Glu Asn  Glu Cys Gln
    2285                2290                2295

Thr Lys  Pro Gly Ile Cys Glu  Asn Gly Arg Cys Leu  Asn Thr Leu
    2300                2305                2310

Gly Ser  Tyr Thr Cys Glu Cys  Asn Asp Gly Phe Thr  Ala Ser Pro
    2315                2320                2325

Thr Gln  Asp Glu Cys Leu Asp  Asn Arg Glu Gly Tyr  Cys Phe Ser
    2330                2335                2340

Glu Val  Leu Gln Asn Met Cys  Gln Ile Gly Ser Ser  Asn Arg Asn
    2345                2350                2355

Pro Val  Thr Lys Ser Glu Cys  Cys Cys Asp Gly Gly  Arg Gly Trp
    2360                2365                2370

Gly Pro  His Cys Glu Ile Cys  Pro Phe Glu Gly Thr  Val Ala Tyr
    2375                2380                2385

Lys Lys  Leu Cys Pro His Gly  Arg Gly Phe Met Thr  Asn Gly Ala
    2390                2395                2400

Asp Ile  Asp Glu Cys Lys Val  Ile His Asp Val Cys  Arg Asn Gly
    2405                2410                2415

Glu Cys  Val Asn Asp Arg Gly  Ser Tyr His Cys Ile  Cys Lys Thr
    2420                2425                2430

Gly Tyr  Thr Pro Asp Ile Thr  Gly Thr Ala Cys Val  Asp Leu Asn
    2435                2440                2445

Glu Cys  Asn Gln Ala Pro Lys  Pro Cys Asn Phe Ile  Cys Lys Asn
    2450                2455                2460

Thr Glu  Gly Ser Tyr Gln Cys  Ser Cys Pro Lys Gly  Tyr Ile Leu
    2465                2470                2475

Gln Glu  Asp Gly Arg Ser Cys  Lys Asp Leu Asp Glu  Cys Ala Thr
    2480                2485                2490

Lys Gln  His Asn Cys Gln Phe  Leu Cys Val Asn Thr  Ile Gly Gly
    2495                2500                2505

Phe Thr  Cys Lys Cys Pro Pro  Gly Phe Thr Gln His  His Thr Ala
    2510                2515                2520

Cys Ile  Asp Asn Asn Glu Cys  Thr Ser Asp Ile Asn  Leu Cys Gly
    2525                2530                2535

Ser Lys  Gly Val Cys Gln Asn  Thr Pro Gly Ser Phe  Thr Cys Glu
    2540                2545                2550

Cys Gln  Arg Gly Phe Ser Leu  Asp Gln Ser Gly Ala  Ser Cys Glu
    2555                2560                2565
```

Asp Val Asp Glu Cys Glu Gly Asn His Arg Cys Gln His Gly Cys
2570 2575 2580

Gln Asn Ile Ile Gly Gly Tyr Arg Cys Ser Cys Pro Gln Gly Tyr
2585 2590 2595

Leu Gln His Tyr Gln Trp Asn Gln Cys Val Asp Glu Asn Glu Cys
2600 2605 2610

Leu Ser Ala His Val Cys Gly Gly Ala Ser Cys His Asn Thr Leu
2615 2620 2625

Gly Ser Tyr Lys Cys Met Cys Pro Thr Gly Phe Gln Tyr Glu Gln
2630 2635 2640

Phe Ser Gly Gly Cys Gln Asp Ile Asn Glu Cys Gly Ser Ser Gln
2645 2650 2655

Ala Pro Cys Ser Tyr Gly Cys Ser Asn Thr Glu Gly Gly Tyr Leu
2660 2665 2670

Cys Gly Cys Pro Pro Gly Tyr Phe Arg Ile Gly Gln Gly His Cys
2675 2680 2685

Val Ser Gly Met Gly Met Gly Arg Gly Gly Pro Glu Pro Pro Ala
2690 2695 2700

Ser Ser Glu Met Asp Asp Asn Ser Leu Ser Pro Glu Ala Cys Tyr
2705 2710 2715

Glu Cys Asp Gln Trp Leu Pro Gln Thr Gly Gln Glu Thr Glu Lys
2720 2725 2730

His Lys Arg Asn
2735

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Glu Thr Glu Lys His Lys Arg Asn
1 5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Ile Ser Leu Arg Gln Lys Pro Met
1 5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Arg Gly Arg Lys Arg Arg
1 5

<210> SEQ ID NO 37
<211> LENGTH: 23

<212> TYPE: RNA
<213> ORGANISM: Artificial Sequence
<220> FEATURE:
<223> OTHER INFORMATION: Synthetic

<400> SEQUENCE: 37
acggagaagc acgaacgaaa cgg 23

<210> SEQ ID NO 38
<211> LENGTH: 123
<212> TYPE: DNA
<213> ORGANISM: Artificial Sequence
<220> FEATURE:
<223> OTHER INFORMATION: Synthetic

<400> SEQUENCE: 38
cagggccctt aggtatctgc agacaaggag accctgatat acctggatgt cggaggcatc 60
agttttcgtt cgtgcttctc cgtttccggc ctcgttttgg gtagccgttg atcttacact 120
cat 123

<210> SEQ ID NO 39
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 39
gnnnnnnnnn nnnnnnnnnn ngg 23

<210> SEQ ID NO 40
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 40
nnnnnnnnnn nnnnnnnnnn ngg 23

<210> SEQ ID NO 41
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 41
ggnnnnnnnn nnnnnnnnnn nnngg 25

<210> SEQ ID NO 42
<211> LENGTH: 28
<212> TYPE: PRT
<213> ORGANISM: Artificial Sequence
<220> FEATURE:

<223> OTHER INFORMATION: Synthetic

<400> SEQUENCE: 42

Ala Ala Gln Ser His Leu Pro Ala Thr Arg Pro Glu Thr Glu Lys His
1 5 10 15

Glu Arg Asn Gly Cys Leu Arg His Pro Gly Arg Val
20 25

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Asp Gln Trp Leu Pro Gln Thr Gly Gln Glu Thr Glu Lys His Lys Arg
1 5 10 15

Asn

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
aggcggccca gagccacctg ccagc 25

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Tyr Pro Lys Arg Gly Arg Lys Arg Arg Ser Thr Asn Glu Asn
1 5 10

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Leu Pro Gln Thr Gly Gln Glu Thr Glu Lys His Lys Arg Asn
1 5 10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Lys His Glu Arg Asn Gly Cys Leu Arg His Pro Gly Arg Val
1 5 10

FIBRILLIN-1 MUTATIONS FOR MODELING NEONATAL PROGEROID SYNDROME WITH CONGENITAL LIPODYSTROPHY

CROSS-REFERENCE TO RELATED APPLICATIONS

This application is a continuation of application Ser. No. 15/663,410 filed Jul. 28, 2017, which claims the benefit of U.S. Application No. 62/368,924, filed Jul. 29, 2016, each of which is herein incorporated by reference in its entirety for all purposes.

REFERENCE TO A SEQUENCE LISTING SUBMITTED AS A TEXT FILE VIA EFS WEB

The Sequence Listing written in file 540642SEQLIST.txt is 184 kilobytes, was created on Dec. 17, 2019, and is hereby incorporated by reference.

BACKGROUND

More than 3000 mutations have been clinically identified in the Fibrillin-1 (FBN1) gene in humans. These mutations have been associated with a variety of conditions, including type I fibrillinopathies, Marfan syndrome, MASS syndrome, isolated ectopia lentis syndrome, thoracic aortic aneurysms, Weill-Marchesani syndrome, geleophysic and acromicric dysplasia, stiff skin syndrome, and neonatal progeroid syndrome with congenital lipodystrophy (NPSCL). Currently available transgenic non-human mammals engineered to have FBN1 mutations do not adequately reflect the symptoms of NPSCL.

SUMMARY

Methods and compositions are provided for modeling neonatal progeroid syndrome with congenital lipodystrophy. In one aspect, the invention provides a non-human mammal whose genome comprises afibrillin-1 (Fbn1) gene comprising a mutation, whereby expression of the gene results in a C-terminally truncated Fbn1 protein disposing the non-human mammal to develop one or more congenital lipodystrophy-like symptoms of neonatal progeroid syndrome. Optionally, the non-human mammal is heterozygous for the mutation. Optionally, the Fbn1 gene includes an Fbn1 promoter endogenous to the non-human mammal. Optionally, the mutation is a frameshift mutation.

In some non-human mammals, the mutation results in a premature termination codon. Optionally, the premature termination codon is in the penultimate or the final exon of the Fbn1 gene. Optionally, the premature termination codon is in the final exon or is less than about 55 base pairs upstream of the last exon-exon junction in the Fbn1 gene. Optionally, the premature termination codon is less than about 55 base pairs upstream of the last exon-exon junction in the Fbn1 gene. Optionally, the premature termination codon is in the final exon or is less than about 20 base pairs upstream of the last exon-exon junction in the Fbn1 gene. Optionally, the mutation is a splice site mutation resulting in the penultimate exon being skipped. Optionally, the mutation results in a premature termination codon in the last coding exon.

In some non-human mammals, the mutation disrupts a basic amino acid recognition sequence for proprotein convertases of the furin family. In some non-human mammals, the mutation results in ablation of the asprosin C-terminal cleavage product of pro-fibrillin-1. In some non-human mammals, the mutation results in disruption of the asprosin C-terminal cleavage product of pro-fibrillin-1. In some non-human mammals, the premature termination codon results in the encoded protein having a positively charged C-terminus.

In some non-human mammals, the encoded protein (i.e., the C-terminally truncated Fbn1 protein) is truncated at a position corresponding to a position between amino acids 2700 and 2790, between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the encoded protein is optimally aligned with SEQ ID NO: 30. Optionally, the encoded protein is truncated such that the last amino acid is at a position corresponding to amino acid 2737, amino acid 2738, or amino acid 2755 in SEQ ID NO: 30 when the encoded protein is optimally aligned with SEQ ID NO: 30.

In some non-human mammals, the encoded protein (i.e., the C-terminally truncated Fbn1 protein) has a C-terminus consisting of the sequence set forth in SEQ ID NO: 8, 42, or 43. In some non-human mammals, the encoded protein has a C-terminus consisting of the sequence set forth in SEQ ID NO: 8, 42, 43, 45, 46, or 47. Optionally, the encoded protein is truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43. Optionally, the encoded protein is truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43 or 46. Optionally, the encoded protein is truncated such that the last amino acid is at a position corresponding to amino acid 2738 in SEQ ID NO: 30 when the encoded protein is optimally aligned with SEQ ID NO: 30, and the C-terminus of the encoded protein consists of the sequence set forth in SEQ ID NO: 8. Optionally, the encoded protein is truncated such that the last amino acid is at a position corresponding to amino acid 2738 in SEQ ID NO: 30 when the encoded protein is optimally aligned with SEQ ID NO: 30, and the C-terminus of the encoded protein consists of the sequence set forth in SEQ ID NO: 8 or 45. Optionally, the encoded protein is truncated such that the last amino acid is at a position corresponding to amino acid 2755 in SEQ ID NO: 30 when the encoded protein is optimally aligned with SEQ ID NO: 30, and the C-terminus of the encoded protein consists of the sequence set forth in SEQ ID NO: 42. Optionally, the encoded protein is truncated such that the last amino acid is at a position corresponding to amino acid 2755 in SEQ ID NO: 30 when the encoded protein is optimally aligned with SEQ ID NO: 30, and the C-terminus of the encoded protein consists of the sequence set forth in SEQ ID NO: 42 or 47.

In some non-human mammals, the Fbn1 gene comprises a mutation in the penultimate exon. Optionally, the penultimate exon of the Fbn1 gene comprises mutations corresponding to the mutations in SEQ ID NO: 26, 27, or 28 relative to the wild type mouse Fbn1 penultimate exon sequence set forth in SEQ ID NO: 25 when the penultimate exon is optimally aligned with SEQ ID NO: 26, 27, or 28.

In some non-human mammals, all or part of the Fbn1 gene has been deleted and replaced with an orthologous human FBN1 gene sequence. Optionally, the mutation resulting in a C-terminal truncation of the encoded protein is located in the orthologous human FBN1 gene sequence. Optionally, the orthologous human FBN1 gene sequence is located at the endogenous non-human mammal Fbn1 locus.

In some non-human mammals, the protein encoded by the mutated Fbn1 gene consists of the sequence set forth in SEQ ID NO: 31, 32, or 33.

In some non-human mammals, the mammal is a rodent. Optionally, the rodent is a rat or a mouse.

In some non-human mammals, the mammal is a mouse. In some non-human mammals or mice, the mutation comprises an insertion or deletion in exon 64 of the endogenous mouse Fbn1 gene that causes a −1 frameshift and results in a premature termination codon at the 3' end of exon 64 or the 5' end of exon 65. Optionally, the mutation comprises an insertion in exon 64 that causes a −1 frameshift and results in a premature termination codon at the 5' end of exon 65. Optionally, the insertion is between positions corresponding to positions 8179 and 8180 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is optimally aligned with SEQ ID NO: 20. Optionally, the mutation comprises an insertion or deletion in exon 64 that causes a −1 frameshift and results in a premature termination codon at the 3' end of exon 64. Optionally, the mutation comprises an insertion between positions corresponding to positions 8209 and 8210 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20. Optionally, the mutation comprises a deletion starting at a position corresponding to position 8161 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20. Optionally, the C-terminally truncated Fbn1 protein has a positively charged C-terminus.

In some non-human mammals, the symptoms comprise one or more of the following: decreased body weight, decreased lean mass, decreased fat mass, decreased body fat percentage, increased food intake normalized by body weight, and increased kyphosis. In some non-human mammals, the symptoms comprise one or more of the following: decreased body weight, decreased lean mass, decreased fat mass, decreased white adipose tissue normalized by body weight, decreased white adipose tissue in combination with preserved brown adipose tissue normalized by body weight, decreased body fat percentage, increased food intake normalized by body weight, and increased kyphosis. Optionally, the non-human mammal has one or more of the following: normal glucose tolerance, normal serum cholesterol levels, normal serum triglyceride levels, and normal serum non-esterified fatty acid levels. Optionally, the non-human mammal has one or more of the following: increased metabolic rate, improved insulin sensitivity, normal glucose tolerance, normal serum cholesterol levels, normal serum triglyceride levels, and normal serum non-esterified fatty acid levels. Optionally, the symptoms comprise at least one of decreased fat mass and decreased body fat percentage and at least one of normal glucose tolerance, normal serum cholesterol levels, normal serum triglyceride levels, and normal serum non-esterified fatty acid levels. Optionally, the symptoms comprise decreased fat mass, decreased body fat percentage, normal glucose tolerance, normal serum cholesterol levels, normal serum triglyceride levels, and normal serum non-esterified fatty acid levels. Optionally, the symptoms comprise decreased white adipose tissue normalized by body weight and at least one of improved insulin sensitivity, normal glucose tolerance, normal serum cholesterol levels, normal serum triglyceride levels, and normal serum non-esterified fatty acid levels. Optionally, the symptoms comprise decreased white adipose tissue normalized by body weight and improved insulin sensitivity.

In another aspect, the invention provides a method of making any of the non-human mammals described herein, comprising: (a) contacting the genome of a non-human mammal pluripotent cell that is not a one-cell stage embryo with: (i) a Cas9 protein; and (ii) a first guide RNA that hybridizes to a first guide RNA recognition sequence within a target genomic locus in the Fbn1 gene, wherein the Fbn1 gene is modified to comprise the mutation resulting in a C-terminal truncation of the encoded protein; (b) introducing the modified non-human mammal pluripotent cell into a host embryo; and (c) implanting the host embryo into a surrogate mother to produce a genetically modified F0 generation non-human mammal in which the Fbn1 gene is modified to comprise the mutation resulting in a C-terminal truncation of the encoded protein, wherein the mutation produces congenital lipodystrophy-like symptoms in the F0 generation non-human mammal. Optionally, the pluripotent cell is an embryonic stem (ES) cell.

In some methods, step (a) further comprises contacting the genome of the non-human mammal pluripotent cell with a second guide RNA that hybridizes to a second guide RNA recognition sequence within the target genomic locus in the Fbn1 gene. In some methods, the method further comprises selecting a modified non-human mammal pluripotent cell after step (a) and before step (b), wherein the modified non-human mammal pluripotent cell is heterozygous for the mutation resulting in a C-terminal truncation of the encoded protein.

In some methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus. Optionally, the exogenous repair template further comprises a nucleic acid insert flanked by the 5' homology arm and the 3' homology arm. Optionally, the nucleic acid insert is homologous or orthologous to the target genomic locus. Optionally, the exogenous repair template is between about 50 nucleotides to about 1 kb in length. Optionally, the exogenous repair template is between about 80 nucleotides to about 200 nucleotides in length. Optionally, the exogenous repair template is a single-stranded oligodeoxynucleotide.

In another aspect, the invention provides a method of making any of the non-human mammals described herein, comprising: (a) contacting the genome of a non-human mammal one-cell stage embryo with: (i) a Cas9 protein; and (ii) a first guide RNA that hybridizes to a first guide RNA recognition sequence within a target genomic locus in the Fbn1 gene, wherein the Fbn1 gene is modified to comprise the mutation resulting in a C-terminal truncation of the encoded protein; and (b) implanting the modified non-human mammal one-cell stage embryo into a surrogate mother to produce a genetically modified F0 generation non-human mammal in which the Fbn1 gene is modified to comprise the mutation resulting in a C-terminal truncation of the encoded protein, wherein the mutation produces congenital lipodystrophy-like symptoms in the F0 generation non-human mammal.

In some methods, step (a) further comprises contacting the genome of the non-human one-cell stage embryo with a second guide RNA that hybridizes to a second guide RNA recognition sequence within the target genomic locus in the Fbn1 gene. In some methods, the method further comprises selecting a modified non-human mammal one-cell stage embryo after step (a) and before step (b), wherein the modified non-human one-cell stage embryo is heterozygous for the mutation resulting in a C-terminal truncation of the encoded protein.

In some methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus. Optionally, the exogenous repair template further comprises a nucleic acid insert flanked by the 5' homology arm and the 3' homology arm. Optionally, the nucleic acid insert is homologous or orthologous to the target genomic locus. Optionally, the exogenous repair template is between about 50 nucleotides to about 1 kb in length. Optionally, the exogenous repair template is between about 80 nucleotides to about 200 nucleotides in length. Optionally, the exogenous repair template is a single-stranded oligodeoxynucleotide.

In another aspect, the invention provides a method of screening a compound for activity for ameliorating congenital lipodystrophy-like symptoms, comprising: (a) contacting any subject non-human mammal described above with the compound; and (b) determining the presence of congenital lipodystrophy-like symptoms of the subject non-human mammal relative to a control non-human mammal not contacted with the compound, wherein the control non-human mammal comprises the same Fbn1 mutation as the subject non-human mammal; whereby activity for ameliorating congenital lipodystrophy-like symptoms is identified by decreased appearance of congenital lipodystrophy-like symptoms in the subject non-human mammal compared with the control non-human mammal.

In some methods, the symptoms comprise one or more of the following: decreased body weight, decreased lean mass, decreased fat mass, decreased body fat percentage, increased food intake normalized by body weight, and increased kyphosis. Optionally, the symptoms comprise at least one of decreased fat mass and decreased body fat percentage. Optionally, the symptoms comprise decreased fat mass and decreased body fat percentage. In some methods, the symptoms comprise one or more of the following: decreased body weight, decreased lean mass, decreased fat mass, decreased white adipose tissue normalized by body weight, decreased white adipose tissue in combination with preserved brown adipose tissue normalized by body weight, decreased body fat percentage, increased food intake normalized by body weight, and increased kyphosis. Optionally, the symptoms comprise decreased white adipose tissue normalized by body weight.

BRIEF DESCRIPTION OF THE FIGURES

FIG. 3 shows the nucleotide sequence (and encoded amino acid sequence) of a region in the penultimate exon of the wild type human FBN1 gene and the nucleotide and amino acid sequences for the corresponding regions in a mutant human FBN1 gene variant associated with neonatal progeroid syndrome with congenital lipodystrophy, a wild-type mouse Fbn1 gene, and an engineered mouse Fbn1 gene variant MAID 8502. FIG. 3 also shows the encoded amino acid sequence of a region in the penultimate exon of the mouse Fbn1 gene for the expected MAID 8502 variant and the MAID 8520 variant that was generated. The forward slash in the amino acid sequences between the "R" and the "S" indicates the furin cleavage site.

FIG. 8A shows body weight of wild type mice and Fbn1 gene variant MAID 8520 heterozygous mice on either a 21% fat breeder diet or a 60% high-fat diet. FIG. 8B shows fat mass (grams of fat mass and percentage of fat mass) of wild type mice and Fbn1 gene variant MAID 8520 heterozygous mice on either a 21% fat breeder diet or a 60% high-fat diet as measured by ECHOMRI™. FIG. 8C shows lean mass (grams of lean mass and percentage of lean mass) of wild type mice and Fbn1 gene variant MAID 8520 heterozygous mice on either a 21% fat breeder diet or a 60% high-fat diet as measured by ECHOMRI™. All mice were 31 weeks of age. Mice were on the 60% high-fat diet for 22 weeks at the time of scan. Asterisks indicate $p<0.0001$ by unpaired t-test.

FIG. 9A shows body weight for male wild type mice and Fbn1 gene variant MAID 8520 heterozygous mice on a chow diet. FIG. 9B shows overnight fasting glucose for male wild type mice and Fbn1 gene variant MAID 8520 heterozygous mice on a chow diet. FIG. 9C shows oral glucose tolerance for male wild type mice and Fbn1 gene variant MAID 8520 heterozygous mice on a chow diet.

FIG. 9D shows body weight for female wild type mice and Fbn1 gene variant MAID 8520 heterozygous mice on a chow diet. FIG. 9E shows overnight fasting glucose for female wild type mice and Fbn1 gene variant MAID 8520 heterozygous mice on a chow diet. FIG. 9F shows oral glucose tolerance for female wild type mice and Fbn1 gene variant MAID 8520 heterozygous mice on a chow diet.

FIG. 10A shows serum cholesterol levels for male wild type mice and Fbn1 gene variant MAID 8520 heterozygous mice on a chow diet. FIG. 10B shows triglyceride levels for male wild type mice and Fbn1 gene variant MAID 8520 heterozygous mice on a chow diet. FIG. 10C shows non-esterified fatty acids (NEFA-C) levels for male wild type mice and Fbn1 gene variant MAID 8520 heterozygous mice on a chow diet.

FIG. 10D shows serum cholesterol levels for female wild type mice and Fbn1 gene variant MAID 8520 heterozygous mice on a chow diet. FIG. 10E shows triglyceride levels for female wild type mice and Fbn1 gene variant MAID 8520 heterozygous mice on a chow diet. FIG. 10F shows non-esterified fatty acids (NEFA-C) levels for female wild type mice and Fbn1 gene variant MAID 8520 heterozygous mice on a chow diet.

FIG. 11A shows the body weights for 34-week-old female Fbn1 gene variant MAID 8520 heterozygous mice on a chow diet. FIGS. 11B-11D show the raw liver, brown adipose tissue (BAT) and visceral white adipose tissue (WAT) weights for each group. FIGS. 11E-11G show those weights as a percentage of body weight.

DEFINITIONS

Figures 1, 2:
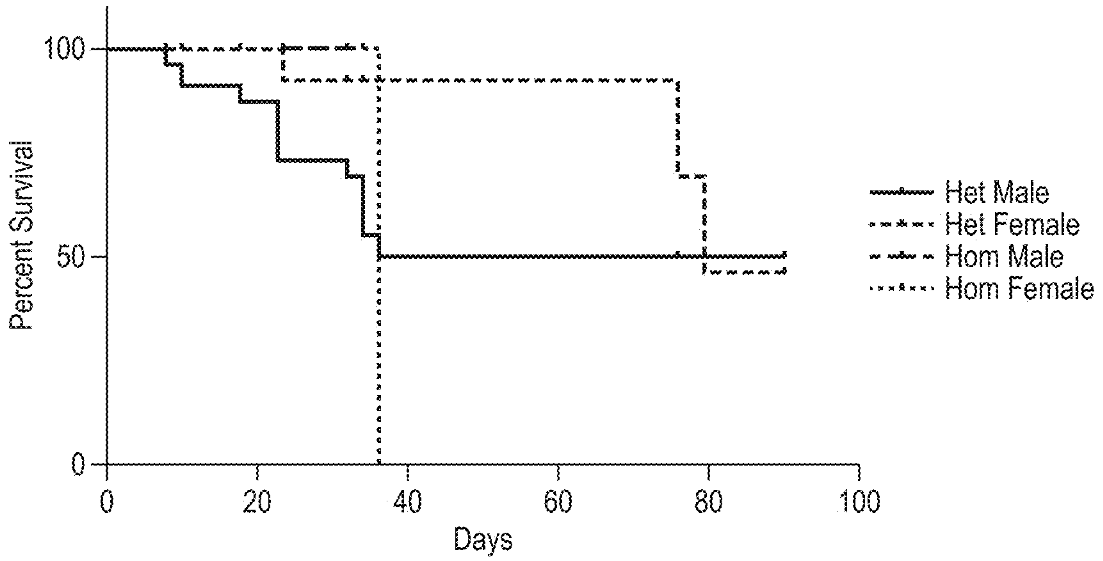
FIG. 1 shows the nucleotide sequence (and encoded amino acid sequence) of a region in the penultimate exon of the wild type human FBN1 gene and the nucleotide and amino acid sequences for the corresponding regions in a mutant human FBN1 gene variant associated with neonatal progeroid syndrome with congenital lipodystrophy, a wild-type mouse Fbn1 gene, and an engineered mouse Fbn1 gene variant MAID 8501. The forward slash in the amino acid sequences between the "R" and the "S" indicates the furin cleavage site.
FIG. 2 shows the percent survival of the male and female F0 founder mice heterozygous or homozygous for the engineered mouse Fbn1 gene variant MAID 8501.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "wild type" includes entities having a structure and/or activity as found in a normal (as contrasted with mutant, diseased, altered, or so forth) state or context. Wild type gene and polypeptides often exist in multiple different forms (e.g., alleles).

The term "isolated" with respect to proteins and nucleic acid includes proteins and nucleic acids that are relatively purified with respect to other bacterial, viral or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "Fbn1 locus" may refer to the specific location of an Fbn1 gene, Fbn1 DNA sequence, Fbn1-encoding sequence, or Fbn1 position on a chromosome of the genome of an organism that has been identified as to where such a sequence resides. An "Fbn1 locus" may comprise a regulatory element of an Fbn1 gene, including, for example, an enhancer, a promoter, 5' and/or 3' UTR, or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas9 proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "substantial identity" as used herein to refer to shared epitopes includes sequences that contain identical residues in corresponding positions. For example, two sequences can be considered to be substantially identical if at least 70%, 75%, 80%, 85%, 90%, 91%, 92%, 93%, 94%, 95%, 96%, 97%, 98%, 99% or more of their corresponding residues are identical over a relevant stretch of residues. The relevant stretch can be, for example, a complete sequence or can be at least 5, 10, 15, or more residues.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas9 protein" or "at least one Cas9 protein" can include a plurality of Cas9 proteins, including mixtures thereof.

Statistically significant means $p \leq 0.05$.

DETAILED DESCRIPTION

I. Overview

The present invention provides non-human animals comprising a mutation in the Fbn1 gene to model neonatal progeroid syndrome with congenital lipodystrophy (NPSCL). Also provided are methods of making such non-human animal models. The non-human animal models can be used for screening compounds for activity in inhibiting or reducing NPSCL or ameliorating NPSCL-like symptoms or screening compounds for activity potentially harmful in promoting or exacerbating NPSCL as well as to provide insights in to the mechanism of NPSCL and potentially new therapeutic and diagnostic targets.

II. Non-Human Animal Models of Neonatal Progeroid Syndrome with Congenital Lipodystrophy Provided herein are non-human animals (e.g., non-human mammals, such as rats or mice) comprising a mutation in the Fbn1 gene. Such non-human animals model neonatal progeroid syndrome with congenital lipodystrophy (NPSCL) and exhibit NPSCL-like symptoms (e.g., congenital lipodystrophy-like symptoms).

A. Neonatal Progeroid Syndrome with Congenital Lipodystrophy (NPSCL).

Neonatal progeroid syndrome (NPS) is characterized by congenital, partial lipodystrophy predominantly affecting the face and extremities. O'Neill et al. (2007) *Am. J. Med. Gen. A.* 143A:1421-1430, herein incorporated by reference in its entirety for all purposes. It is also referred to as neonatal progeroid syndrome with congenital lipodystrophy (NPSCL), marfanoid-progeroid syndrome, or marfanoid-progeroid-lipodystrophy (MPL) syndrome. It is characterized by congenital, extreme thinness due to a reduction in subcutaneous adipose tissue, predominantly affecting the face and extremities. See Hou et al. (2009) *Pediatrics and Neonatology* 50:102-109 and O'Neill et al. (2007) *Am. J. Med. Gen. A.* 143A:1421-1430, each of which is herein incorporated by reference in its entirety for all purposes. The phenotype is typically apparent at birth, and even before birth as intrauterine growth retardation, with thin skin and prominent vasculature due to paucity of subcutaneous fat. O'Neill et al. (2007). Patients display a body mass index (BMI) several standard deviations below normal for age, at all ages. O'Neill et al. (2007). Although NPS patients appear progeroid, due to facial dysmorphic features and reduced subcutaneous fat, they do not have the usual features of true progeria such as cataracts, premature greying of hair or insulin resistance. O'Neill et al. (2007). Patients can have normal fasting plasma glucose and insulin levels suggesting that they have normal insulin sensitivity and glucose handling. O'Neill et al. (2007).

The cardinal features of patients with NPSCL include: (1) congenital lipodystrophy; (2) premature birth with an accelerated linear growth disproportionate to the weight gain; and (3) a progeroid appearance with distinct facial features. See, e.g., Takenouchi et al. (2013) *Am. J. Med. Genet. Part A* 161A:3057-3062, herein incorporated by reference in its entirety for al purposes. Jacquinet et al. report the marfanoid-progeroid phenotype as including the following: intrauterine growth retardation and/or preterm birth, senile facial appearance and decreased subcutaneous fat at birth, and progressive marfanoid features. Aortic root dilation, ectopic lentis and dural ectasia can appear with time. Developmental milestones and intelligence appear to be normal. Jacquinet et al. (2014) *Eur. J. Med. Genet.* 57(5):203-234, herein incorporated by reference in its entirety for all purposes.

The phenotype observed in human NPSCL patients, unlike many lipodystrophic syndromes, is a normal metabolic profile in terms of glucose homeostasis and circulating lipids despite having no visceral adipose tissue. Human NPSCL patients have normal glucose homeostasis despite loss of white adipose tissue.

The non-human animal models disclosed herein exhibit NPSCL-like symptoms (e.g., congenital lipodystrophy-like symptoms). Such symptoms can include, for example, one or more of the following: decreased body weight, decreased lean mass, decreased fat mass, decreased white adipose tissue (e.g., normalized by body weight), decreased white adipose tissue in combination with preservation of brown adipose tissue (e.g., normalized by body weight), decreased body fat percentage, increased food intake normalized by body weight, and increased kyphosis. Such symptoms can include, for example, one or more of the following: decreased body weight, decreased lean mass, decreased fat mass, decreased body fat percentage, increased food intake normalized by body weight, and increased kyphosis. Such symptoms can be in combination with one or more of the following: increased metabolic rate, improved insulin sensitivity, normal glucose tolerance, normal serum cholesterol levels, normal serum triglyceride levels, and normal serum non-esterified fatty acid levels. Alternatively, such symptoms can be in combination with one or more of the following: normal glucose tolerance, normal serum cholesterol levels, normal serum triglyceride levels, and normal serum non-esterified fatty acid levels. For example, the symptoms can comprise at least one of decreased fat mass and decreased body fat percentage and at least one of normal glucose tolerance, normal serum cholesterol levels, normal serum triglyceride levels, and normal serum non-esterified fatty acid levels. Alternatively, the symptoms can comprise decreased fat mass, decreased body fat percentage, normal glucose tolerance, normal serum cholesterol levels, normal serum triglyceride levels, and normal serum non-esterified fatty acid levels. Other possible phenotypes include one or more of decreased liver weight, decreased brown adipose tissue (BAT) weight, decreased visceral white adipose tissue (WAT) weight, decreased WAT weight normalized to body weight, elevated metabolic rate normalized to body weight, increased energy expenditure, improved glucose tolerance, and improved insulin sensitivity on high-fat diet. For example, the symptoms can comprise decreased white adipose tissue (e.g., in combination with preserved brown adipose tissue) normalized by body weight in combination with at least one of improved metabolic rate, improved insulin sensitivity, normal glucose tolerance, normal serum cholesterol levels, normal serum triglyceride levels, and normal serum non-esterified fatty acid levels. For example, the symptoms can comprise decreased white adipose tissue (e.g., in combination with preserved brown adipose tissue) normalized by body weight in combination improved insulin sensitivity.

The decrease or increase can be statistically significant. For example, the decrease or increase can be by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100% compared with a control wild type non-human animal.

B. Fbn1 Mutations

NPSCL is associated with mutations in the FBN1 gene in humans. See, e.g., Takenouchi et al. (2013) *Am. J. Med. Genet. Part A* 161A:3057-3062; Graul-Neumann et al. (2010) *Am. J. Med. Genet. A.* 152A(11):2749-2755; Goldblatt et al. (2011) *Am. J. Med. Genet. A* 155A(4):717-720; Horn and Robinson (2011) *Am. J. Med. Genet. A.* 155A(4); 721-724; Jacquinet et al. (2014) *Eur. J. Med. Genet.* 57(5): 203-234; and Romere et al. (2016) *Cell* 165(3):566-579, each of which is herein incorporated by reference in its entirety for all purposes. FBN1 is a 230 kb gene with 65 coding exons (66 total exons) that encode the structural glycoprotein fibrillin-1, a major component of the microfibrils in elastic and non-elastic extracellular matrix. Profibrillin-1 is translated as a 2871-amino-acid long proprotein, which is cleaved at the C-terminus by the protease furin. This generates a 140-amino-acid long C-terminal cleavage product (i.e., asprosin), in addition to mature fibrillin-1 (an extracellular matrix component). An exemplary human fibrillin-1 sequence is assigned UniProt Accession No. P35555.

More than 3000 mutations have been clinically identified in the FBN1 gene. See, e.g., Wang et al. (2016) *Forensic Science International* 261:e1-e4 and www.umd/be/FBN1/, each of which is herein incorporated by reference in its entirety for all purposes. These mutations have been associated with a variety of conditions, including type I fibrillinopathies, Marfan syndrome, MASS syndrome, isolated ectopia lentis syndrome, thoracic aortic aneurysms, Weill-Marchesani syndrome, geleophysic and acromicric dysplasia, stiff skin syndrome, and neonatal progeroid syndrome with congenital lipodystrophy. See, e.g., Davis and Summers (2012) *Mol. Genet. Metab.* 107(4):635-647, herein incorporated by reference in its entirety for all purposes. The most common of these is the autosomal dominant Marfan syndrome comprising ocular, cardiovascular, and skeletal manifestations. See Loeys et al. (2010) *J. Med. Genet.* 47(7):476-485 and Jacquinet et al. (2014) *Eur. J. Med. Genet.* 57(5):203-234, each of which is herein incorporated by reference in its entirety for all purposes. Mutations in classical Marfan syndrome are scattered throughout the FBN1 gene with limited genotype-phenotype relationship. See, e.g., Faivre et al. (2007) *Am. J. Hum. Genet.* 81(3): 454-466 and Jacquinet et al. (2014) *Eur. J. Med. Genet.* 57(5):203-234, each of which is herein incorporated by reference in its entirety for all purposes.

The non-human animal models of NPSCL disclosed herein comprise a mutation in the Fbn1 gene that produces NPSCL-like symptoms (e.g., congenital lipodystrophy-like symptoms) in the non-human animal. The mutations can be in the endogenous Fbn1 gene in the non-human animal. Alternatively, the non-human animal can comprise a humanized Fbn1 locus in which all or part of the endogenous Fbn1 gene has been deleted and replaced with the corresponding orthologous sequence from the human FBN1 gene or other orthologous sequences from other mammals, such as non-human primates. The replacement by orthologous sequence can occur in a particular exon or intron to introduce a mutation from the orthologous sequences. The replacement can also be of all exons, or all exons and introns, or of all exons, introns and flanking sequences including regulatory sequences. Depending on the extent of replacement by orthologous sequences, regulatory sequences, such as a promoter, can be endogenous or supplied by the replacing orthologous sequence.

Preferably, the non-human animal is heterozygous for the mutation. Preferably the mutation results in a C-terminal truncation of the encoded protein. For example, the mutation can cause a frameshift. A frameshift mutation is a sequence change between the translation initiation codon (start codon) and termination codon (stop codon) in which, compared to a reference sequence, translation shifts to another frame. For example, the reading frame can be shifted one nucleotide in the 5' direction (−1 frameshift) or one nucleotide in the 3' direction (+1 frameshift). A protein encoded by a gene with a frameshift mutation will be identical to the protein encoded by the wild type gene from the N-terminus to the frameshift mutation, but different beyond that point. Such frameshifts can result in a premature termination codon. Such premature codons can be, for example, in the penultimate exon or the last exon. Optionally, the premature termination codon is less than about 100 base pairs upstream or less than about 55 base pairs upstream of the last exon-exon junction. For example, the premature termination codon can be less than about 100 base pairs, 90 base pairs, 80 base pairs, 70 base pairs, 60 base pairs, 55 base pairs, 50 base pairs, 40 base pairs, 30 base pairs, 25 base pairs, or 20 base pairs upstream of the last exon-exon junction within the penultimate coding exon. Alternatively, the premature termination codon can be in the last coding exon (e.g., as the result of a splice site mutation resulting in skipping of the penultimate coding exon). Optionally, the premature termination codon is within the last coding exon (e.g., exon 65 of mouse Fbn1) or is in the penultimate exon (e.g., exon 64 of mouse Fbn1), wherein if the premature termination codon is in the penultimate exon, it is less than about 55 base pairs (e.g., less than about 20 base pairs, such as 19 base pairs) upstream of the last exon-exon junction. Optionally, if the premature codon is within the last coding exon, it is less than about 100 base pairs, 90 base pairs, 80 base pairs, 70 base pairs, 60 base pairs, 55 base pairs, 50 base pairs, 40 base pairs, 30 base pairs, 25 base pairs, 20 base pairs, 15 base pairs, or 10 base pairs (e.g., 9 base pairs) downstream of the last exon-exon junction. Optionally, the premature termination codon is between positions corresponding to positions 8150 and 8300, 8160 and 8290, 8170 and 8280, 8180 and 8270, 8190 and 8260, 8200 and 8250, 8210 and 8300, 8210 and 8290, 8210 and 8280, 8210 and 8270, 8210 and 8260, 8210 and 8250, 8200 and 8300, 8200 and 8290, 8200 and 8280, 8200 and 8270, 8200 and 8260, 8200 and 8250, 8150 and 8245, 8160 and 8245, 8170 and 8245, 8180 and 8245, 8190 and 8245, 8200 and 8245, 8150 and 8250, 8160 and 8250, 8170 and 8250, 8180 and 8250, 8190 and 8250, 8200 and 8250, or 8210 and 8245 in the wild type mouse Fbn1 coding sequence set forth in SEQ ID NO: 20 when the Fbn1 gene comprising the mutation is optimally aligned with SEQ ID NO: 20.

The premature termination codon can result in a truncated protein with a positively charged C-terminus. Among the 20 common amino acids, five have a side chain which can be charged. At pH=7, two are negatively-charged (aspartic acid (Asp, D), and glutamic acid (Glu, E)) and three are positively charged (lysine (Lys, K), arginine (Arg, R), and histidine (His, H)). In some cases, the premature termination codon can result in a truncated protein with an extremely positively charged C-terminus (e.g., ETEKHKRN (SEQ ID NO: 34)). Alternatively, the premature termination codon can result in a truncated protein with a less positively charged C-terminus (e.g., ISLRQKPM (SEQ ID NO: 35)).

Optionally, the mutation disrupts a basic amino acid recognition sequence for proprotein convertases of the furin family (RGRKRR (SEQ ID NO: 36)). For example, the mutation can result in a protein truncated upstream of the furin recognition sequence, can mutate the furin recognition sequence, or can result in a frameshift upstream of the furin recognition sequence. Optionally, the mutation is within 100 base pairs of the basic amino acid recognition sequence for proprotein convertases of the furin family. For example, the mutation can be within about 90 base pairs, 80 base pairs, 70 base pairs, 60 base pairs, 50 base pairs, 40 base pairs, or 30 base pairs of the furin recognition sequence. As an example, such mutations can include insertions or deletions of nucleotides resulting in a frameshift in the penultimate exon or the last exon. As another example, such mutations can include donor splice site mutations that result in skipping of the penultimate exon and a subsequent frameshift that results in a premature termination codon in the last exon.

In some non-human animals, the mutation results in disruption or ablation (e.g., heterozygous ablation) of the C-terminal cleavage product (i.e., asprosin) of profibrillin-1. Disruption or ablation of the C-terminal cleavage product can result, for example, from disruption of the basic amino acid recognition sequence for proprotein convertases of the furin family. Alternatively, disruption or ablation of the C-terminal cleavage product can result, for example, from the mutation creating a premature termination codon such that the C-terminal cleavage product is truncated. Disruption of asprosin results in either decreased production of asprosin or production of asprosin with decreased activity. In some non-human animals, the Fbn1 gene comprises a mutation in the penultimate exon. For example, the penultimate exon of the Fbn1 gene can comprise mutations corresponding to the mutations in SEQ ID NO: 26, 27, or 28 (the penultimate exons from MAID alleles 8501, 8520, and 8502, respectively) relative to the penultimate exon from the wild type mouse Fbn1 (SEQ ID NO: 25) when the penultimate exon is optimally aligned with SEQ ID NO: 26, 27, or 28.

In some non-human animals, the Fbn1 protein encoded by the mutated Fbn1 gene is truncated at a position corresponding to a position between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the encoded protein is optimally aligned with SEQ ID NO: 30. For example, the encoded protein can be truncated such that the last amino acid is at a position corresponding to amino acid 2737, amino acid 2738, or amino acid 2755 in the wild type mouse Fbn1 protein set forth in SEQ ID NO: 30 when the encoded protein is optimally aligned with SEQ ID NO: 30. Likewise, the encoded protein can be truncated such that the last amino acid is at a position corresponding to the last amino acid of the truncated Fbn1 proteins encoded by the MAID 8501, 8502, and 8520 Fbn1 variants described herein.

As another example, the encoded protein can have a C-terminus consisting of the sequence set forth in SEQ ID NO: 8, 42, or 43, or the encoded protein can have a C-terminus corresponding to the C-terminus of the proteins encoded by the MAID 8501, 8502, and 8520 Fbn1 variants described herein. For example, the encoded protein can be truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43. As another example, the encoded protein can be truncated such that the last amino acid is at a position corresponding to amino acid 2738 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 8. As another example, the encoded protein can be truncated such that the last amino acid is at a position corresponding to amino acid 2755 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 42. Exemplary truncated Fbn1 proteins include SEQ ID NO: 31, 32 and 33.

An Fbn1 gene refers to any known gene encoding an Fbn1 protein, such as described in Swiss-Prot and GenBank databases, and including variants of these proteins as described in such databases or otherwise having at least 95, 96, 97, 98 or 99% identity to wild type sequences, including hybrids of such genes, and including any such gene or hybrid of such genes modified by a mutation to produce NPSCL-like symptoms (e.g., congenital lipodystrophy-like symptoms) as further described herein. If any variations are present other than residues mutated to produce NPSCL-like symptoms, the variations preferably do not affect coding sequences or if they do affect coding sequences preferably do so by introducing conservative substitutions.

In some of the non-human animals disclosed herein, the endogenous Fbn1 gene is mutated to produce NPSCL-like symptoms. Exemplary mouse Fibrillin-1 sequences are assigned Accession No. NM_007993.2 or UniProt Accession No. Q61554. Exemplary rat Fibrillin-1 sequences are assigned Accession No. NM_031825.1 or UniProt Accession No. Q9WUH8. Other exemplary Fibrillin-1 sequences include Accession Nos. NM_001001771.1 (pig), NM_001287085.1 (dog), and NM 174053.2 (cow). The mouse Fbn1 gene lies on the long arm of chromosome 15 at 15q15-q21.1. Megenis et al. (1991) *Genomics* 11:346-351, herein incorporated by reference in its entirety for all purposes. Like human FBN1, it is a very large gene that is highly fragmented into 65 exons. Pereira et al. (1993) *Hum. Mol. Genet.* 2:961-968, herein incorporated by reference in its entirety for all purposes.

Such mutations in the endogenous Fbn1 gene can correspond with mutations identified in the human FBN1 gene in patients diagnosed with NPSCL as disclosed elsewhere herein. A residue (e.g., nucleotide or amino acid) in an endogenous Fbn1 gene (or protein) can be determined to correspond with a residue in the human FBN1 gene (or protein) by optimally aligning the two sequences for maximum correspondence over a specified comparison window (e.g., the Fbn1 coding sequence), wherein the portion of the polynucleotide (or amino acid) sequence in the comparison window may comprise additions or deletions (i.e., gaps) as compared to the reference sequence (which does not comprise additions or deletions) for optimal alignment of the two sequences (see, e.g., discussion elsewhere herein with regard to sequence identity and complementarity). Two residues correspond if they are located at the same position when optimally aligned.

A specific example of a mutation in a mouse Fbn1 gene that produces NPSCL-like symptoms is c.8207_8208ins1bp (reference sequence NM_007993.2 or reference sequence SEQ ID NO: 20). Some non-human animals disclosed herein comprise an Fbn1 gene with a mutation corresponding to c.8207_8208ins1bp in NM_007993.2 or SEQ ID NO: 20 when the Fbn1 gene optimally aligned with NM_007933.2 or SEQ ID NO: 20. A specific example of mutations within a mouse Fbn1 gene sequence that can produce NPSCL-like symptoms are the mutations in SEQ ID NO: 21, 22, or 23 relative to SEQ ID NO: 20 (mouse WT Fbn1 cDNA), or the mutations in SEQ ID NO: 26, 27, or 28 relative to SEQ ID NO: 25 (penultimate exon of WT Fbn1 cDNA). Specific examples of mutated mouse Fbn1 proteins that can produce NPSCL-like symptoms are SEQ ID NOS: 31, 32, and 33.

In other non-human animals disclosed herein, all or part of the endogenous Fbn1 gene has been deleted and replaced with the corresponding sequence from the human Fbn1 gene. For example, the human Fbn1 gene sequence can be located at the endogenous Fbn1 locus (i.e., all or part of the endogenous Fbn1 locus has been humanized). In such non-human animals, the corresponding sequence of the human FBN1 gene can include a mutation that produces NPSCL-like symptoms. An exemplary human FBN1 cDNA sequence is assigned Accession No. NM_000138.3, and an exemplary human Fibrillin-1 protein sequence is assigned UniProt Accession No. P35555. When specific mutation positions in the human FBN1 gene are referred to herein, they are in reference to FBN1 cDNA NM_000138.3 (Ensembl transcript FBN1-201=ENST00000316623). Likewise, when human FBN1 gene introns or exons are referred to herein, they are in reference to reference sequence NM_000138.3 and ENST00000316623, with exon numbering starting from exon 2 according to the localization of the ATG start codon (i.e., exon numbering starting from the first coding exon). Numbering of mutation positions is based on the Human Genome Variation Society (HGVS) sequence variant nomenclature (varnomen.hgvs.org). The prefix “c” indicates that the reference sequence is a coding DNA reference sequence (based on a protein coding transcript). Numbering starts with “c.1” at the “A” of the “ATG” translation initiation (start) codon and ends with the last nucleotide of the translation termination (stop) codon (i.e., TAA, TAG, or TGA). Nucleotides at the 5' end of an intron are numbered relative to the last nucleotide of the directly upstream exon, followed by a “+” (plus) and their position in to the intron (e.g., c.87+1). Nucleotides at the 3' end of an intron are numbered relative to the first nucleotide of the directly downstream exon, followed by a “−” (minus) and their position out of the intron (e.g., c.88-3). Substitution mutations where, compared to the reference sequence, one nucleotide is replaced by one other nucleotide are in the format of “prefix” “position_substituted” “reference_nucleotide”>“new_nucleotide” (e.g., c.123A>G indicates that the reference sequence is a coding DNA reference sequence and the “A” at position 123 in the reference sequence is substituted with a “G.” Deletion mutations where, compared to a reference sequence, one or more nucleotides are not present are in the format of “prefix” “position(s)_deleted” “del” (e.g., c.123_127del indicates that nucleotides at positions 123-127 in the coding DNA reference sequence are deleted). Insertion mutations where, compared to the reference sequence, one or more nucleotides are inserted and where the insertion is not a copy of a sequence immediately 5' are in the format “prefix” “positions flanking” “ins” “inserted_sequence” (e.g., c.123_124insAGC indicates that the sequence AGC is inserted between positions 123 and 124 of the coding DNA reference sequence). Insertion/deletion (indel) mutations where, compared to a reference sequence, one or more nucleotides are replaced by one or more other nucleotides (and wherein the mutation is not a substitution, inversion, or conversion) are in the format “prefix” “position(s)_deleted” “delins” “inserted_sequence” (e.g., c.123_127delinsAG indicates that the sequence between positions 123 and 127 was deleted and replaced with the sequence “AG” in the coding DNA reference sequence).

Preferably, the mutation is between c.8100 and c.8300 or c.8150 and c.8250 in the human FBN1 sequence or corresponding positions in a non-human Fbn1 sequence when optimally aligned with the human FBN1 sequence. Exemplary mutations in the human FBN1 gene include insertions or deletions of nucleotides resulting in a frameshift. See, e.g., Takenouchi et al. (2013) *Am. J. Med. Genet. Part A* 161A:3057-3062; Graul-Neumann et al. (2010) *Am. J. Med. Genet. A.* 152A(11):2749-2755; and Goldblatt et al. (2011) *Am. J. Med. Genet. A* 155A(4):717-720, each of which is herein incorporated by reference in its entirety for all purposes. One example of such a mutation in the human FBN1 gene is c.8155_8156del. This is a deletion of two base pairs in coding exon 64 (the penultimate exon), which causes a frameshift with a subsequent premature termination codon 17 codons downstream of p.Lys2719. See, e.g., Graul-Neumann et al. (2010) *Am. J. Med. Genet. A.* 152A(11): 2749-2755. Another example of such a mutation in the human FBN1 gene that results in a frameshift resulting in the same premature termination codon is c.8156_8175del. See, e.g., Goldblatt et al. (2011) *Am. J. Med. Genet. A* 155A(4): 717-720. Yet another example of such a mutation in the human FBN1 gene that results in a frameshift resulting in the same premature termination codon is c.8175_8182de. See, e.g., Takenouchi et al. (2013) *Am. J. Med. Genet. Part A* 161A:3057-3062. Another example of such a mutation in the human FBN1 gene resulting in a premature termination codon in coding exon 64 is c.8206 8207insA. See, e.g., Romere et al. (2016) *Cell* 165(3):566-579. The non-human animals described herein can comprise an Fbn1 gene with mutations corresponding to any of these mutations when the Fbn1 gene sequence is optimally aligned with the human FBN1 gene corresponding to the cDNA sequence set forth in Accession No. NM_000138.3.

Other exemplary mutations in the human FBN1 gene include donor splice site mutations that result in skipping of the penultimate exon (exon 64) and a subsequent frameshift that results in a premature termination codon in the last exon (exon 65). See, e.g., Horn and Robinson (2011) *Am. J. Med.*

*Genet. A.* 155A(4):721-724 and Jacquinet et al. (2014) *Eur. J. Med. Genet.* 57(5):203-234, each of which is herein incorporated by reference in its entirety for all purposes. One example of such a mutation in the human FBN1 gene is c.8226+1G>A. See, e.g., Jacquinet et al. (2014) *Eur. J. Med. Genet.* 57(5):203-234. Another example of such a mutation in the human FBN1 gene is c.8226+1G>T. See, e.g., Horn and Robinson (2011) *Am. J. Med. Genet. A.* 155A(4):721-724 and Romere et al. (2016) *Cell* 165(3):566-579. These mutations affect the splice-donor site of intron 64, changing the highly conserved GT dinucleotide, and lead to skipping of coding exon 64 and the production of a stable mRNA that should allow synthesis of a truncated profibrillin-1 in which the C-terminal furin cleavage site is altered. Skipping of exon 64 results in a frameshift at the beginning of coding exon 65 and the generation of a premature termination codon at the ninth downstream codon.

The non-human animals described herein can comprise an Fbn1 gene with mutations corresponding to any of these mutations when the Fbn1 gene sequence is optimally aligned with the human FBN1 gene sequence corresponding to the cDNA sequence set forth in Accession No. NM_000138.3. Likewise, the non-human animals described herein can comprise an Fbn1 gene with mutations such that the mutant Fbn1 gene encodes an Fbn1 protein corresponding to any of the human FBN1 proteins encoded by any of the mutant human FBN1 genes described herein. Similarly, the encoded protein can be truncated such that the last amino acid is at a position corresponding to the last amino acid of the truncated Fbn1 proteins encoded by any of the mutant human FBN1 genes described herein, and/or can have a C-terminus identical to the C-terminus of the truncated Fbn1 proteins encoded by any of the mutant human FBN1 genes described herein.

Certain exemplary mutant Fbn1 alleles are mutant mouse Fbn1 alleles. For example, the mutation in the mutant mouse Fbn1 allele can comprise an insertion or deletion in the penultimate exon (exon 64) that causes a −1 frameshift and results in a premature termination codon at the 3' end of the penultimate exon (exon 64) or the 5' end of the final exon (exon 65) of Fbn1.

As one example, the mutation can comprise an insertion or a deletion in exon 64 that causes a −1 frameshift and results in a premature termination codon at the 5' end of exon 65, as in the MAID 8520 allele described in Example 2 and set forth in SEQ ID NO: 22. Optionally, the insertion or deletion is upstream of a position corresponding to position 8241 (e.g., an insertion between positions corresponding to positions 8179 and 8180) in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is optimally aligned with SEQ ID NO: 20.

As another example, the mutation can comprise an insertion or deletion in the penultimate exon (exon 64) that causes a −1 frameshift and results in a premature termination codon at the 3' end of the penultimate exon (exon 64), as in the MAID 8501 allele described in Example 1 and set forth in SEQ ID NO: 21 or the MAID 8502 allele described in Example 2 and set forth in SEQ ID NO: 23. Optionally, the insertion or deletion is upstream of a position corresponding to position 8214 (e.g., an insertion between positions corresponding to positions 8209 and 8210, or a deletion starting at a position corresponding to position 8161) in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20.

One exemplary mutant mouse Fbn1 allele is the MAID 8501 allele described in Example 1 and set forth in SEQ ID NO: 21. The protein encoded by the MAID 8501 allele is set forth in SEQ ID NO: 31. Using NM_007993.2 as a reference sequence, the mutation in this mutant Fbn1 allele is c.8213_8214delinsACT. This mutation, which was created by inserting an A between c.8212 and 8213 and making a G>T substitution at c.8214, results in a premature termination codon in the penultimate exon (exon 64) of Fbn1, 19 nucleotides upstream of the boundary between exons 64 and 65. The mutation is within the last 50 nucleotides (the last 24 nucleotides) of the penultimate exon and is predicted to escape mRNA nonsense-mediated decay (NMD), leading to expression of a mutant, truncated profibrillin protein.

Another exemplary mouse allele is the MAID 8502 allele described in Example 2 and set forth in SEQ ID NO: 23. The protein encoded by the MAID 8502 allele is set forth in SEQ ID NO: 33. This is a mutant Fbn1 allele corresponding to the human c.8155_8156del Fbn1 allele, which has a deletion of two base pairs in coding exon 64 (the penultimate exon) causing a frameshift with a subsequent premature termination codon 17 codons downstream of p.Lys2719. In the MAID 8502 allele, the deletion of two base pairs is 71 nucleotides upstream of the boundary between exons 64 and 65. The mutation results in a premature termination codon in the penultimate exon (exon 64) of mouse Fbn1, 19 nucleotides upstream of the boundary between exons 64 and 65.

Another exemplary mouse allele is the MAID 8520 allele described in Example 2 and set forth in SEQ ID NO: 22. The protein encoded by the MAID 8520 allele is set forth in SEQ ID NO: 32. Using NM_007993.2 as a reference sequence, the mutation in this mutant Fbn1 allele is 8179_8180insAGGCGGCCCAGAGCCACCTGCCAGC. This mutation was created through a 25-bp insertion (inserted sequence set forth in SEQ ID NO: 44) in the penultimate exon (exon 64), 54 nucleotides upstream of the boundary between exons 64 and 65. It results in a frameshift in the penultimate exon (exon 64) of mouse Fbn1. The mutation results in a premature termination codon in the final exon (exon 65) of mouse Fbn1, 9 nucleotides downstream of the boundary between exons 64 and 65.

Each of the above exemplary mouse Fbn1 alleles results in a frameshift mutation in the penultimate exon (exon 64) of the mouse Fbn1 gene. Each frameshift mutation results in a premature termination codon within either the 3' end of the penultimate exon (exon 64) or the 5' end of the final exon (exon 65) of the mouse Fbn1 gene. Because each mutation results in a premature termination codon, each mutation disrupts or ablates the C-terminal cleavage product (i.e., asprosin) of profibrillin-1 because the C-terminal cleavage product, if produced, will necessarily be truncated as well. In addition, each of the above exemplary mouse Fbn1 alleles results in a positively charged C-terminal end due to a greater number of lysines, arginines, and histidines relative to aspartic acids and glutamic acids. The last 14 amino acids of the Fbn1 proteins encoded by the MAID 8501, MAID 8502, and MAID 8520 alleles, which are set forth in SEQ ID NOS: 45, 46, and 47, respectively.

C. Non-Human Animals

Any suitable non-human animal can be used as a model of NPSCL as disclosed herein. Such non-human animals are preferably mammals, such as rodents (e.g., rats, mice, and hamsters). Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). The term "non-human" excludes humans.

Mice employed in the non-human animal models disclosed herein can be from any strain, including, for example, from a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice have a strain comprising 50% BALB/c, 25% C57BL/6, and 25% 129. Alternatively, the mice can comprise a strain or strain combination that excludes BALB/c.

Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10(8):836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Mice employed in the non-human animal models provided herein can also be from a mix of an aforementioned 129 strain and an aforementioned C57BL/6 strain (e.g., 50% 129 and 50% C57BL/6). Likewise, mice employed in the non-human animal models provided herein can be from a mix of aforementioned 129 strains or a mix of aforementioned BL/6 strains (e.g., the 129S6 (129/SvEvTac) strain).

Rats employed in the non-human animal models provided herein can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be from a strain derived from a mix of two or more strains recited above. For example, the rat can be from a DA strain or an ACI strain. The ACI rat strain is characterized as having black agouti, with white belly and feet and an $RT1^{avl}$ haplotype. Such strains are available from a variety of sources including Harlan Laboratories. The Dark Agouti (DA) rat strain is characterized as having an agouti coat and an $RT1^{avl}$ haplotype. Such rats are available from a variety of sources including Charles River and Harlan Laboratories. In some cases, the rats are from an inbred rat strain. See, e.g., US 2014/0235933 A1, herein incorporated by reference in its entirety for all purposes.

II. Generation of Animal Models of Neonatal Progeroid Syndrome with Congenital Lipodystrophy A. Generating Fbn1 Mutations in Cells Various methods are provided for modifying an Fbn1 gene in a genome within a cell (e.g., a pluripotent cell or a one-cell stage embryo) through use of nuclease agents and/or exogenous repair templates. The methods can occur in vitro, ex vivo, or in vivo. The nuclease agent can be used alone or in combination with an exogenous repair template. Alternatively, the exogenous repair template can be used alone or in combination with a nuclease agent.

Repair in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break.

Repair of a target nucleic acid (e.g., the Fbn1 gene) mediated by an exogenous repair template can include any process of exchange of genetic information between the two polynucleotides. For example, NHEJ can also result in the targeted integration of an exogenous repair template through direct ligation of the break ends with the ends of the exogenous repair template (i.e., NHEJ-based capture). Such NHEJ-mediated targeted integration can be preferred for insertion of an exogenous repair template when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous repair template and the cleaved genomic sequence, or via ligation of sticky ends (i.e., having 5' or 3' overhangs) using an exogenous repair template that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Repair can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Targeted genetic modifications to an Fbn1 gene in a genome can be generated by contacting a cell with an exogenous repair template comprising a 5' homology arm that hybridizes to a 5' target sequence at a target genomic locus within the Fbn1 gene and a 3' homology arm that hybridizes to a 3' target sequence at the target genomic locus within the Fbn1 gene. The exogenous repair template can recombine with the target genomic locus to generate the targeted genetic modification to the Fbn1 gene. Such methods can result, for example, in an Fbn1 gene modified to comprise a mutation resulting in a C-terminal truncation of the encoded protein. Examples of exogenous repair templates are disclosed elsewhere herein.

Targeted genetic modifications to an Fbn1 gene in a genome can also be generated by contacting a cell with a nuclease agent that induces one or more nicks or double-strand breaks at a recognition sequence at a target genomic locus within the Fbn1 gene. Such methods can result, for example, in an Fbn1 gene modified to comprise a mutation resulting in a C-terminal truncation of the encoded protein. Examples and variations of nuclease agents that can be used in the methods are described elsewhere herein.

For example, targeted genetic modifications to an Fbn1 gene in a genome can be generated by contacting a cell with a Cas protein and one or more guide RNAs that hybridize to one or more guide RNA recognition sequences within a target genomic locus in the Fbn1 gene. For example, such methods can comprise contacting a cell with a Cas protein and a guide RNA that hybridizes to a guide RNA recognition sequence within the Fbn1 gene. The Cas protein and the guide RNA form a complex, and the Cas protein cleaves the guide RNA recognition sequence. Cleavage by the Cas9 protein can create a double-strand break or a single-strand break (e.g., if the Cas9 protein is a nickase). Such methods can result, for example, in an Fbn1 gene modified to comprise a mutation resulting in a C-terminal truncation of the encoded protein. Examples and variations of Cas9 proteins and guide RNAs that can be used in the methods are described elsewhere herein.

Optionally, the cell can be further contacted with one or more additional guide RNAs that hybridize to additional guide RNA recognition sequences within the target genomic locus in the Fbn1 gene. By contacting the zygote with one or more additional guide RNAs (e.g., a second guide RNA that hybridizes to a second guide RNA recognition sequence), cleavage by the Cas protein can create two or more double-strand breaks or two or more single-strand breaks (e.g., if the Cas protein is a nickase).

Optionally, the cell can additionally be contacted with one or more exogenous repair templates which recombine with the target genomic locus in the Fbn1 gene to generate a targeted genetic modification. Examples and variations of exogenous repair templates that can be used in the methods are disclosed elsewhere herein.

The Cas protein, guide RNA(s), and exogenous repair template(s) can be introduced into the cell in any form and by any means as described elsewhere herein, and all or some of the Cas protein, guide RNA(s), and exogenous repair template(s) can be introduced simultaneously or sequentially in any combination.

In some such methods, the repair of the target nucleic acid (e.g., the Fbn1 gene) by the exogenous repair template occurs via homology-directed repair (HDR). Homology-directed repair can occur when the Cas protein cleaves both strands of DNA in the Fbn1 gene to create a double-strand break, when the Cas protein is a nickase that cleaves one strand of DNA in the target nucleic acid to create a single-strand break, or when Cas nickases are used to create a double-strand break formed by two offset nicks. In such methods, the exogenous repair template comprises 5' and 3' homology arms corresponding to 5' and 3' target sequences. The guide RNA recognition sequence(s) or cleavage site(s) can be adjacent to the 5' target sequence, adjacent to the 3' target sequence, adjacent to both the 5' target sequence and the 3' target sequence, or adjacent to neither the 5' target sequence nor the 3' target sequence. Optionally, the exogenous repair template can further comprise a nucleic acid insert flanked by the 5' and 3' homology arms, and the nucleic acid insert is inserted between the 5' and 3' target sequences. For example, the nucleic acid insert can comprise one or more modifications when compared with the wild type non-human animal Fbn1 sequence, or it can comprise all or part of a human FBN1 coding sequence comprising one or more modifications when compared with the wild type human FBN1 sequence. If no nucleic acid insert is present, the exogenous repair template can function to delete the genomic sequence between the 5' and 3' target sequences. Examples of exogenous repair templates are disclosed elsewhere herein.

Alternatively, the repair of the Fbn1 gene mediated by the exogenous repair template can occur via non-homologous end joining (NHEJ)-mediated ligation. In such methods, at least one end of the exogenous repair template comprises a short single-stranded region that is complementary to at least one overhang created by Cas-mediated cleavage in the Fbn1 gene. The complementary end in the exogenous repair template can flank a nucleic acid insert. For example, each end of the exogenous repair template can comprise a short single-stranded region that is complementary to an overhang created by Cas-mediated cleavage in the Fbn1 gene, and these complementary regions in the exogenous repair template can flank a nucleic acid insert. For example, the nucleic acid insert can comprise one or more modifications when compared with the wild type non-human animal Fbn1 sequence, or it can comprise all or part of a human FBN1 coding sequence comprising one or more modifications when compared with the wild type human FBN1 sequence.

Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the Fbn1 gene. Alternatively, such overhangs can be created by using paired Cas nickases. For example, the cell can be contacted with first and second nickases that cleave opposite strands of DNA, whereby the genome is modified through double nicking. This can be accomplished by contacting a cell with a first Cas protein nickase, a first guide RNA that hybridizes to a first guide RNA recognition sequence within the target genomic locus in the Fbn1 gene, a second Cas protein nickase, and a second guide RNA that hybridizes to a second guide RNA recognition sequence within target genomic locus in the Fbn1 gene. The first Cas protein and the first guide RNA form a first complex, and the second Cas protein and the second guide RNA form a second complex. The first Cas protein nickase cleaves a first strand of genomic DNA within the first guide RNA recognition sequence, the second Cas protein nickase cleaves a second strand of genomic DNA within the second guide RNA recognition sequence, and optionally the exogenous repair template recombines with the target genomic locus in the Fbn1 gene to generate the targeted genetic modification.

The first nickase can cleave a first strand of genomic DNA (i.e., the complementary strand), and the second nickase can cleave a second strand of genomic DNA (i.e., the non-complementary strand). The first and second nickases can be created, for example, by mutating a catalytic residue in the RuvC domain (e.g., the D10A mutation described elsewhere herein) of Cas9 or mutating a catalytic residue in the HNH domain (e.g., the H840A mutation described elsewhere herein) of Cas9. In such methods, the double nicking can be employed to create a double-strand break having staggered ends (i.e., overhangs). The first and second guide RNA recognition sequences can be positioned to create a cleavage site such that the nicks created by the first and second nickases on the first and second strands of DNA create a double-strand break. Overhangs are created when the nicks within the first and second CRISPR RNA recognition sequences are offset. The offset window can be, for example, at least about 5 bp, 10 bp, 20 bp, 30 bp, 40 bp, 50 bp, 60 bp, 70 bp, 80 bp, 90 bp, 100 bp or more. See, e.g., Ran et al. (2013) *Cell* 154:1380-1389; Mali et al. (2013) *Nat. Biotech.* 31:833-838; and Shen et al. (2014) *Nat. Methods* 11:399-404.

B. Nuclease Agents

Any nuclease agent that induces a nick or double-strand break into a desired recognition sequence can be used in the methods and compositions disclosed herein. A naturally occurring or native nuclease agent can be employed so long as the nuclease agent induces a nick or double-strand break in a desired recognition sequence. Alternatively, a modified or engineered nuclease agent can be employed. An "engineered nuclease agent" includes a nuclease that is engineered (modified or derived) from its native form to specifically recognize and induce a nick or double-strand break in the desired recognition sequence. Thus, an engineered nuclease agent can be derived from a native, naturally occurring nuclease agent or it can be artificially created or synthesized. The engineered nuclease can induce a nick or double-strand break in a recognition sequence, for example, wherein the recognition sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a recognition sequence or other DNA can be referred to herein as "cutting" or "cleaving" the recognition sequence or other DNA.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition sequence and hence retain nick or double-strand-break-inducing activity. For example, any of the nuclease agents described herein can be modified from a native endonuclease sequence and designed to recognize and induce a nick or double-strand break at a recognition sequence that was not recognized by the native nuclease agent. Thus, some engineered nucleases have a specificity to induce a nick or double-strand break at a recognition sequence that is different from the corresponding native nuclease agent recognition sequence. Assays for nick or double-strand-break-inducing activity are known and generally measure the overall activity and specificity of the endonuclease on DNA substrates containing the recognition sequence.

The term "recognition sequence for a nuclease agent" includes a DNA sequence at which a nick or double-strand break is induced by a nuclease agent. The recognition sequence for a nuclease agent can be endogenous (or native) to the cell or the recognition sequence can be exogenous to the cell. A recognition sequence that is exogenous to the cell is not naturally occurring in the genome of the cell. The recognition sequence can also exogenous to the polynucleotides of interest that one desires to be positioned at the target locus. In some cases, the recognition sequence is present only once in the genome of the host cell.

Active variants and fragments of the exemplified recognition sequences are also provided. Such active variants can comprise at least 65%, 70%, 75%, 80%, 85%, 90%, 91%, 92%, 93%, 94%, 95%, 96%, 97%, 98%, 99% or more sequence identity to the given recognition sequence, wherein the active variants retain biological activity and hence are capable of being recognized and cleaved by a nuclease agent in a sequence-specific manner. Assays to measure the double-strand break of a recognition sequence by a nuclease agent are known in the art (e.g., TAQMAN® qPCR assay, Frendewey et al. (2010) *Methods in Enzymology* 476:295-307, herein incorporated by reference in its entirety for all purposes).

The length of the recognition sequence can vary, and includes, for example, recognition sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

The recognition sequence of the nuclease agent can be positioned anywhere in or near the target genomic locus. The recognition sequence can be located within a coding region of a gene (e.g., the Fbn1 gene), or within regulatory regions that influence the expression of the gene. A recognition sequence of the nuclease agent can be located in an intron, an exon, a promoter, an enhancer, a regulatory region, or any non-protein coding region.

One type of nuclease agent that can be employed in the various methods and compositions disclosed herein is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50:21617-21622; Scholze & Boch (2010) *Virulence* 1:428-432; Christian et al. (2010) *Genetics* 186:757-761; Li et al. (2011) *Nucleic Acids Res.* 39(1):359-372; and Miller et al. (2011) *Nature Biotechnology* 29:143-148, each of which is herein incorporated by reference in its entirety for all purposes.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes. In various embodiments, TAL effector nucleases are engineered that cut in or near a target nucleic acid sequence in, for example, a genomic locus of interest, wherein the target nucleic acid sequence is at or near a sequence to be modified by a an exogenous repair template. The TAL nucleases suitable for use with the various methods and compositions provided herein include those that are specifically designed to bind at or near target nucleic acid sequences to be modified by exogenous repair templates as described elsewhere herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

Another example of a nuclease agent that can be employed in the various methods and compositions disclosed herein is a zinc-finger nuclease (ZFN). In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US 2006/0246567; US 2008/0182332; US 2002/0081614; US 2003/0021776; WO 2002/057308 A2; US 2013/0123484; US 2010/0291048; WO 2011/017293 A2; and Gaj et al. (2013) *Trends in Biotechnology* 31(7):397-405, each of which is herein incorporated by reference in its entirety for all purposes.

Another type of nuclease agent that can be employed in the various methods and compositions disclosed herein is a meganuclease. Meganucleases have been classified into four families based on conserved sequence motifs: the LAGLIDADG, GIY-YIG, H-N-H, and His-Cys box families. These motifs participate in the coordination of metal ions and hydrolysis of phosphodiester bonds. Meganucleases are notable for their long recognition sequences and for tolerating some sequence polymorphisms in their DNA substrates. Meganuclease domains, structure, and function are known. See, e.g., Guhan and Muniyappa (2003) *Crit Rev Biochem Mol Biol.* 38:199-248; Lucas et al. (2001) *Nucleic Acids Res.* 29:960-969; Jurica and Stoddard, (1999) *Cell Mol Life Sci* 55:1304-1326; Stoddard (2006) *Q Rev Biophys* 38:49-95; and Moure et al. (2002) *Nat Struct Biol* 9:764. In some examples, a naturally occurring variant and/or engineered derivative meganuclease is used. Methods for modifying the kinetics, cofactor interactions, expression, optimal conditions, and/or recognition sequence specificity are known, and methods for screening for activity are known. See, e.g., Epinat et al., (2003) *Nucleic Acids Res.* 31:2952-2962; Chevalier et al. (2002) *Mol. Cell* 10:895-905; Gimble et al. (2003) *Mol. Biol.* 334:993-1008; Seligman et al. (2002) *Nucleic Acids Res.* 30:3870-3879; Sussman et al. (2004) *J. Mol. Biol.* 342:31-41; Rosen et al. (2006) *Nucleic Acids Res.* 34:4791-4800; Chames et al. (2005) *Nucleic Acids Res.* 33:e178; Smith et al. (2006) *Nucleic Acids Res.* 34:e149; Gruen et al. (2002) *Nucleic Acids Res.* 30:e29; Chen and Zhao (2005) *Nucleic Acids Res* 33:e154; WO 2005/105989; WO 2003/078619; WO 2006/097854; WO 2006/097853; WO 2006/097784; and WO 2004/031346, each of which is herein incorporated by reference in its entirety for all purposes.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-Ppol, PI-PspI, F-SceI, F-SceII, F-SuvI, F-TeeI, F-TevII, I-AmaI, I-AniI, I-ChuI, I-Cmoel, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TeeI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, a meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Suitable nuclease agents also include restriction endonucleases, which include Type I, Type II, Type III, and Type IV endonucleases. Type I and Type III restriction endonucleases recognize specific recognition sequences but typically cleave at a variable position from the nuclease binding site, which can be hundreds of base pairs away from the cleavage site (recognition sequence). In Type II systems, the restriction activity is independent of any methylase activity, and cleavage typically occurs at specific sites within or near to the binding site. Most Type II enzymes cut palindromic sequences. However, Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example, in the REBASE database (webpage at rebase.neb.com; Roberts et al. (2003) *Nucleic Acids Res.* 31:418-420; Roberts et al. (2003) *Nucleic Acids Res.* 31:1805-1812; and Belfort et al. (2002) in *Mobile DNA II, pp.* 761-783, Eds. Craigie et al., (ASM Press, Washington, D.C.), each of which is herein incorporated by reference in its entirety for all purposes.

Other suitable nuclease agents for use in the methods and compositions described herein include CRISPR-Cas systems, which are described elsewhere herein.

The nuclease agent may be introduced into the cell by any means known in the art. A polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally, or constitutively expressed within the cell. For example, the polynucleotide encoding the nuclease agent can be contained in an expression cassette and be operably linked to a conditional promoter, an inducible promoter, a constitutive promoter, or a tissue-specific promoter. Such promoters are discussed in further detail elsewhere herein. Alternatively, the nuclease agent can be introduced into the cell as an mRNA encoding a nuclease agent.

A polynucleotide encoding a nuclease agent can be stably integrated in the genome of the cell and operably linked to a promoter active in the cell. Alternatively, a polynucleotide encoding a nuclease agent can be in a targeting vector or in a vector or a plasmid that is separate from the targeting vector comprising the insert polynucleotide.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

C. CRISPR-Cas Systems

The methods disclosed herein can utilize Clustered Regularly Interspersed Short Palindromic Repeats (CRISPR)/CRISPR-associated (Cas) systems or components of such systems to modify a genome within a cell. CRISPR-Cas systems include transcripts and other elements involved in the expression of, or directing the activity of, Cas genes. A CRISPR-Cas system can be a type I, a type II, or a type III system. Alternatively a CRISPR/Cas system can be, for example, a type V system (e.g., subtype V-A or subtype V-B). The methods and compositions disclosed herein can employ CRISPR-Cas systems by utilizing CRISPR complexes (comprising a guide RNA (gRNA) complexed with a Cas protein) for site-directed cleavage of nucleic acids.

The CRISPR-Cas systems used in the methods disclosed herein are non-naturally occurring. A “non-naturally occurring” system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR-Cas systems employ non-naturally occurring CRISPR complexes comprising a gRNA and a Cas protein that do not naturally occur together.

(1) Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf2 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the Fbn1 gene (e.g., a double-strand break with blunt ends), or it can be a nickase that creates a single-strand break in the Fbn1 gene.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Preferably, the Cas protein is a Cas9 protein or is derived from a Cas9 protein from a type II CRISPR-Cas system. Cas9 proteins are from a type II CRISPR-Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Additional examples of the Cas9 family members are described in WO 2014/131833, herein incorporated by reference in its entirety for all purposes. Cas9 from *S. pyogenes* (assigned SwissProt accession number Q99ZW2) is a preferred enzyme. Cas9 from *S. aureus* (assigned UniProt accession number J7RUA5) is another preferred enzyme.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is a preferred enzyme.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a guide RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null Cas protein). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas9 proteins can also be tethered to exogenous repair templates or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous repair template or labeled nucleic acid can be tethered to the C-terminus, the N-terminus, or to an internal region within the Cas9 protein. Preferably, the exogenous repair template or labeled nucleic acid is tethered to the C-terminus or the N-terminus of the Cas9 protein. Likewise, the Cas9 protein can be tethered to the 5' end, the 3' end, or to an internal region within the exogenous repair template or labeled nucleic acid. That is, the exogenous repair template or labeled nucleic acid can be tethered in any orientation and polarity. Preferably, the Cas9 protein is tethered to the 5' end or the 3' end of the exogenous repair template or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

(2) Guide RNAs

A "guide RNA" or "gRNA" is an RNA molecule that binds to a Cas protein (e.g., Cas9 protein) and targets the Cas protein to a specific location within a target DNA (e.g., the Fbn1 gene). Guide RNAs can comprise two segments: a "DNA-targeting segment" and a "protein-binding segment." "Segment" includes a section or region of a molecule, such as a contiguous stretch of nucleotides in an RNA. Some gRNAs comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve cleavage. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. In systems in which only a crRNA is needed, the crRNA can be the gRNA. The crRNA additionally provides the single-stranded DNA-targeting segment that hybridizes to a guide RNA recognition sequence. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA (e.g., the Fbn1 gene) in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR-Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the guide RNA recognition sequence within the target DNA can be at least 60% over about 20 contiguous nucleotides. As an example, the percent complementarity between the DNA-targeting sequence and the guide RNA recognition sequence within the target DNA is 100% over the 14 contiguous nucleotides at the 5' end of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the guide RNA recognition sequence within the target DNA is 100% over the seven contiguous nucleotides at the 5' end of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-target sequence are complementary to the target DNA. For example, the DNA-targeting sequence can be 20 nucleotides in length and can comprise 1, 2, or 3 mismatches with the target DNA (the guide RNA recognition sequence). Preferably, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising an exogenous repair template and/or a vector comprising a nucleic acid encoding a Cas protein. Alternatively, it can be in a vector or a plasmid that is separate from the vector comprising an exogenous repair template and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

(3) Guide RNA Recognition Sequences

The term "guide RNA recognition sequence" includes nucleic acid sequences present in a target DNA (e.g., the Fbn1 gene) to which a DNA-targeting segment of a gRNA will bind, provided sufficient conditions for binding exist. For example, guide RNA recognition sequences include sequences to which a guide RNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A guide RNA recognition sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence of the nickase on the first strand is separated from the guide RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA recognition sequence. Optionally, the guide RNA recognition sequence can be flanked on the 3' end by the PAM. Alternatively, the guide RNA recognition sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-CC$N_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT (SEQ ID NO: 146) or NNGRR (SEQ ID NO: 147), where N can A, G, C, or T, and R can be G or A. In some cases (e.g., for FnCpf1), the PAM sequence can be upstream of the 5' end and have the sequence 5'-TTN-3'.

Examples of guide RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as G$N_{19}$NGG (SEQ ID NO: 39) or $N_{20}$NGG (SEQ ID NO: 40) (see, e.g., WO 2014/165825, herein incorporated by reference in its entirety for all purposes). The guanine at the 5' end can facilitate transcription by RNA polymerase in cells. Other examples of guide RNA recognition sequences can include two guanine nucleotides at the 5' end (e.g., GG$N_{20}$NGG; SEQ ID NO: 41) to facilitate efficient transcription by T7 polymerase in vitro. See, e.g., WO 2014/065596, herein incorporated by reference in its entirety for all purposes. Other guide RNA recognition sequences can have between 4-22 nucleotides in length of SEQ ID NOS: 39-41, including the 5' G or GG and the 3' GG or NGG. Yet other guide RNA recognition sequences can have between 14 and 20 nucleotides in length of SEQ ID NOS: 39-41.

The guide RNA recognition sequence can be any nucleic acid sequence endogenous or exogenous to a cell. The guide RNA recognition sequence can be a sequence coding a gene product (e.g., a protein) or a non-coding sequence (e.g., a regulatory sequence) or can include both.

D. Exogenous Repair Templates

The methods and compositions disclosed herein can utilize exogenous repair templates to modify an Fbn1 gene following cleavage of the Fbn1 gene with a nuclease agent. For example, the cell can be a one-cell stage embryo, and the exogenous repair template can be less 5 kb in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein (e.g., a targeting vector having a length of at least 10 kb or having 5' and 3' homology arms having a sum total of at least 10 kb). Using exogenous repair templates in combination with nuclease agents may result in more precise modifications within the Fbn1 gene by promoting homology-directed repair.

In such methods, the nuclease agent cleaves the Fbn1 gene to create a single-strand break (nick) or double-strand break, and the exogenous repair template recombines the Fbn1 gene via non-homologous end joining (NHEJ)-mediated ligation or through a homology-directed repair event. Optionally, repair with the exogenous repair template removes or disrupts the nuclease cleavage site so that alleles that have been targeted cannot be re-targeted by the nuclease agent.

Exogenous repair templates can comprise deoxyribonucleic acid (DNA) or ribonucleic acid (RNA), they can be single-stranded or double-stranded, and they can be in linear or circular form. For example, an exogenous repair template can be a single-stranded oligodeoxynucleotide (ssODN). See, e.g., Yoshimi et al. (2016) *Nat. Commun.* 7:10431, herein incorporated by reference in its entirety for all purposes. An exemplary exogenous repair template is between about 50 nucleotides to about 5 kb in length, is between about 50 nucleotides to about 3 kb in length, or is between about 50 to about 1,000 nucleotides in length. Other exemplary exogenous repair templates are between about 40 to about 200 nucleotides in length. For example, an exogenous repair template can be between about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Alternatively, an exogenous repair template can be between about 50 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Alternatively, an exogenous repair template can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. Alternatively, an exogenous repair template can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein.

In one example, an exogenous repair template is an ssODN that is between about 80 nucleotides and about 200 nucleotides in length. In another example, an exogenous repair templates is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous repair templates can include modifications or sequences that provide for additional desirable features (e.g., modified or regulated stability; tracking or detecting with a fluorescent label; a binding site for a protein or protein complex; and so forth). Exogenous repair templates can comprise one or more fluorescent labels, purification tags, epitope tags, or a combination thereof. For example, an exogenous repair template can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous repair template that has been directly integrated into a cleaved Fbn1 gene having protruding ends compatible with the ends of the exogenous repair template. The label or tag can be at the 5' end, the 3' end, or internally within the exogenous repair template. For example, an exogenous repair template can be conjugated at 5' end with the IR700 fluorophore from Integrated DNA Technologies (5'IRDYE®700).

Exogenous repair templates can also comprise nucleic acid inserts including segments of DNA to be integrated in the Fbn1 gene. Integration of a nucleic acid insert in the Fbn1 gene can result in addition of a nucleic acid sequence of interest in the Fbn1 gene, deletion of a nucleic acid sequence of interest in the Fbn1 gene, or replacement of a nucleic acid sequence of interest in the Fbn1 gene (i.e., deletion and insertion). Some exogenous repair templates are designed for insertion of a nucleic acid insert in the Fbn1 gene without any corresponding deletion in the Fbn1 gene. Other exogenous repair templates are designed to delete a nucleic acid sequence of interest in the Fbn1 gene without any corresponding insertion of a nucleic acid insert. Yet other exogenous repair templates are designed to delete a nucleic acid sequence of interest in the Fbn1 gene and replace it with a nucleic acid insert.

The nucleic acid insert or the corresponding nucleic acid in the Fbn1 gene being deleted and/or replaced can be various lengths. An exemplary nucleic acid insert or corresponding nucleic acid in the Fbn1 gene being deleted and/or replaced is between about 1 nucleotide to about 5 kb in length or is between about 1 nucleotide to about 1,000 nucleotides in length. For example, a nucleic acid insert or a corresponding nucleic acid in the Fbn1 gene being deleted and/or replaced can be between about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Likewise, a nucleic acid insert or a corresponding nucleic acid in the Fbn1 gene being deleted and/or replaced can be between about 1 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Likewise, a nucleic acid insert or a corresponding nucleic acid in the Fbn1 gene being deleted and/or replaced can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. A nucleic acid being deleted from the Fbn1 gene can also be between about 1 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, about 90 kb to about 100 kb, about 100 kb to about 200 kb, about 200 kb to about 300 kb, about 300 kb to about 400 kb, about 400 kb to about 500 kb, about 500 kb to about 600 kb, about 600 kb to about 700 kb, about 700 kb to about 800 kb, about 800 kb to about 900 kb, about 900 kb to about 1 Mb or longer. Alternatively, a nucleic acid being deleted from the Fbn1 gene can be between about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster, a rabbit, a pig, a bovine, a deer, a sheep, a goat, a cat, a dog, a ferret, a primate (e.g., marmoset, rhesus monkey), a domesticated mammal, an agricultural mammal, a turtle, or any other organism of interest.

The nucleic acid insert can comprise a sequence that is homologous or orthologous to all or part of the Fbn1 gene (e.g., a portion of the gene encoding a particular motif or region of the Fibrillin-1 protein). The homologous sequence can be from a different species or the same species. For example, the nucleic acid insert can comprise a sequence that comprises one or more point mutations (e.g., 1, 2, 3, 4, 5, or more) compared with a sequence targeted for replacement in the Fbn1 gene. In some cases, the nucleic acid insert is a human Fbn1 sequence. This can result in humanization of all or part of the Fbn1 locus in the non-human animal if insertion of the nucleic acid insert results in replacement of all or part of the Fbn1 non-human nucleic acid sequence with the corresponding orthologous human nucleic acid sequence (i.e., the nucleic acid insert is inserted in place of the corresponding non-human DNA sequence at its endogenous genomic locus). The inserted human sequence can further comprise one or more mutations in the human Fbn1 gene.

The nucleic acid insert or the corresponding nucleic acid in the Fbn1 gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

The nucleic acid insert can also comprise a conditional allele. The conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Nucleic acid inserts can also comprise a polynucleotide encoding a selection marker. Alternatively, the nucleic acid inserts can lack a polynucleotide encoding a selection marker. The selection marker can be contained in a selection cassette. Optionally, the selection cassette can be a self-deleting cassette. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. Exemplary selection markers include neomycin phosphotransferase ($neo^r$), hygromycin B phosphotransferase ($hyg^r$), puromycin-N-acetyltransferase ($puro^r$), blasticidin S deaminase ($bse^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A given cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternatively, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In one example, the site-specific recombination sites flank a polynucleotide encoding a selection marker and/or a reporter gene contained within the nucleic acid insert. Following integration of the nucleic acid insert in the Fbn1 gene, the sequences between the site-specific recombination sites can be removed. Optionally, two exogenous repair templates can be used, each with a nucleic acid insert comprising a site-specific recombination site. The exogenous repair templates can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example in the REBASE database (webpage at rebase.neb.com; Roberts et al., (2003) *Nucleic Acids Res.* 31:418-420; Roberts et al., (2003) *Nucleic Acids Res.* 31:1805-1812; and Belfort et al. (2002) in Mobile DNA II, pp. 761-783, Eds. Craigie et al., (ASM Press, Washington, D.C.)).

(1) Repair Templates for Non-Homologous-End-Joining-Mediated Insertion

Some exogenous repair templates have short single-stranded regions at the 5' end and/or the 3' end that are complementary to one or more overhangs created by Cas-protein-mediated cleavage at the target genomic locus (e.g., in the Fbn1 gene). These overhangs can also be referred to as 5' and 3' homology arms. For example, some exogenous repair templates have short single-stranded regions at the 5' end and/or the 3' end that are complementary to one or more overhangs created by Cas-protein-mediated cleavage at 5' and/or 3' target sequences at the target genomic locus. Some such exogenous repair templates have a complementary region only at the 5' end or only at the 3' end. For example, some such exogenous repair templates have a complementary region only at the 5' end complementary to an overhang created at a 5' target sequence at the target genomic locus or only at the 3' end complementary to an overhang created at a 3' target sequence at the target genomic locus. Other such exogenous repair templates have complementary regions at both the 5' and 3' ends. For example, other such exogenous repair templates have complementary regions at both the 5' and 3' ends e.g., complementary to first and second overhangs, respectively, generated by Cas-mediated cleavage at the target genomic locus. For example, if the exogenous repair template is double-stranded, the single-stranded complementary regions can extend from the 5' end of the top strand of the repair template and the 5' end of the bottom strand of the repair template, creating 5' overhangs on each end. Alternatively, the single-stranded complementary region can extend from the 3' end of the top strand of the repair template and from the 3' end of the bottom strand of the template, creating 3' overhangs.

The complementary regions can be of any length sufficient to promote ligation between the exogenous repair template and the Fbn1 gene. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). Preferably, the nicks within the first and second guide RNA recognition sequences and/or the third and fourth guide RNA recognition sequences can be offset nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous repair template can be designed with single-stranded complementary regions that are complementary to the overhangs created by the nicks within the first and second guide RNA recognition sequences and by the nicks within the third and fourth guide RNA recognition sequences. Such an exogenous repair template can then be inserted by non-homologous-end-joining-mediated ligation.

(2) Repair Templates for Insertion by Homology-Directed Repair

Some exogenous repair templates comprise homology arms. If the exogenous repair template also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the Fbn1 gene, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25 to about 30, about 30 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the Fbn1 gene. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternatively, for example, they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

When a nuclease agent is used in combination with an exogenous repair template, the 5' and 3' target sequences are preferably located in sufficient proximity to the nuclease cleavage site so as to promote the occurrence of a homologous recombination event between the target sequences and the homology arms upon a single-strand break (nick) or double-strand break at the nuclease cleavage site. The term “nuclease cleavage site” includes a DNA sequence at which a nick or double-strand break is created by a nuclease agent (e.g., a Cas9 protein complexed with a guide RNA). The target sequences within the Fbn1 gene that correspond to the 5' and 3' homology arms of the exogenous repair template are “located in sufficient proximity” to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous repair template can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous repair template and the nuclease cleavage site can vary. For example, target sequences can be located 5' to the nuclease cleavage site, target sequences can be located 3' to the nuclease cleavage site, or the target sequences can flank the nuclease cleavage site.

In cells other than one-cell stage embryos, the exogenous repair template can be a “large targeting vector” or “LTVEC,” which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; and 7,105,348; and in WO 2002/036789, each of which is herein incorporated by reference in its entirety for all purposes. LTVECs can be in linear form or in circular form.

LTVECs can be of any length and are typically at least 10 kb in length. For example, an LTVEC can be from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR The sum total of the 5' homology arm and the 3' homology arm in an LTVEC is typically at least 10 kb. As an example, the 5' homology arm can range from about 5 kb to about 100 kb and/or the 3' homology arm can range from about 5 kb to about 100 kb. Each homology arm can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can be, for example, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.

LTVECs can comprise nucleic acid inserts having nucleic acid sequences larger than those typically used by other approaches intended to perform homologous recombination in cells. For example, an LTVEC can comprise a nucleic acid insert ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, or greater.

E. Contacting the Genome of a Cell and Introducing Nucleic Acids into Cells

Contacting the genome of a cell can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) and/or one or more exogenous repair templates into the cell, provided that if the cell is a one-cell stage embryo, for example, the exogenous repair template can be less than 5 kb in length. Contacting the genome of cell (i.e., contacting a cell) can comprise introducing only one of the above components, one or more of the components, or all of the components into the cell. "Introducing" includes presenting to the cell the nucleic acid or protein in such a manner that the sequence gains access to the interior of the cell. The introducing can be accomplished by any means, and one or more of the components (e.g., two of the components, or all of the components) can be introduced into the cell simultaneously or sequentially in any combination. For example, an exogenous repair template can be introduced prior to the introduction of a nuclease agent, or it can be introduced following introduction of nuclease agent (e.g., the exogenous repair template can be administered about 1, 2, 3, 4, 8, 12, 24, 36, 48, or 72 hours before or after introduction of the nuclease agent). See, e.g., US 2015/0240263 and US 2015/0110762, each of which is herein incorporated by reference in its entirety for all purposes.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs.

For example, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

In some methods, DNA encoding a nuclease agent (e.g., a Cas protein and a guide RNA) and/or DNA encoding an exogenous repair template can be introduced into a cell via DNA minicircles. See, e.g., WO 2014/182700, herein incorporated by reference in its entirety for all purposes. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

Transfection protocols as well as protocols for introducing nucleic acids or proteins into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a one-cell stage embryo) can also be accomplished by microinjection. In one-cell stage embryos, microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a protein or a DNA encoding a DNA encoding a Cas protein is preferably into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a nuclease agent protein is injected into the cytoplasm, the protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, N.Y.: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some cases, the cells employed in the methods and compositions have a DNA construct stably incorporated into their genome. In such cases, the contacting can comprise providing a cell with the construct already stably incorporated into its genome. For example, a cell employed in the methods disclosed herein may have a preexisting Cas-encoding gene stably incorporated into its genome (i.e., a Cas-ready cell). "Stably incorporated" or "stably introduced" or "stably integrated" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

F. Types of Targeted Genetic Modifications

Various types of targeted genetic modifications can be introduced using the methods described herein. Such targeted modifications can include, for example, additions of one or more nucleotides, deletions of one or more nucleotides, substitutions of one or more nucleotides, a point mutation, a knockout of a polynucleotide of interest or a portion thereof, a knock-in of a polynucleotide of interest or a portion thereof, a replacement of an endogenous nucleic acid sequence with a heterologous, exogenous, homologous, or orthologous nucleic acid sequence, a domain swap, an exon swap, an intron swap, a regulatory sequence swap, a gene swap, or a combination thereof. For example, at least 1, 2, 3, 4, 5, 7, 8, 9, 10 or more nucleotides can be changed (e.g., deleted, inserted, or substituted) to form the targeted genomic modification. The deletions, insertions, or replacements can be of any size, as disclosed elsewhere herein. See, e.g., Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Such targeted genetic modifications can result in disruption of a target genomic locus, can introduce disease-causing mutations or disease-causing alleles, can result in humanization of a target genomic locus (i.e., replacement of a non-human nucleic acid sequence with a homologous or an orthologous human nucleic acid sequence), can create conditional alleles, and so forth. Disruption can include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation), and it can result in inactivation (i.e., loss of function) or loss of an allele.

The targeted genetic modification can be, for example, a biallelic modification or a monoallelic modification. Preferably, the targeted genetic modification is a monoallelic modification. Biallelic modifications include events in which the same modification is made to the same locus on corresponding homologous chromosomes (e.g., in a diploid cell), or in which different modifications are made to the same locus on corresponding homologous chromosomes. In some methods, the targeted genetic modification is a monoallelic modification. A monoallelic modification includes events in which a modification is made to only one allele (i.e., a modification to the Fbn1 gene in only one of the two homologous chromosomes). Homologous chromosomes include chromosomes that have the same genes at the same loci but possibly different alleles (e.g., chromosomes that are paired during meiosis). The term allele includes any of one or more alternative forms of a genetic sequence. In a diploid cell or organism, the two alleles of a given sequence typically occupy corresponding loci on a pair of homologous chromosomes.

A monoallelic mutation can result in a cell that is heterozygous for the targeted Fbn1 modification. Heterozygosity includes situation in which only one allele of the Fbn1 gene (i.e., corresponding alleles on both homologous chromosomes) have the targeted modification.

A biallelic modification can result in homozygosity for a targeted modification. Homozygosity includes situations in which both alleles of the Fbn1 gene (i.e., corresponding alleles on both homologous chromosomes) have the targeted modification. For example, the biallelic modification can be generated when a Cas protein cleaves a pair of first and second homologous chromosomes within a first guide RNA recognition sequence (i.e., at a first cleavage site within the first guide RNA recognition sequence), thereby generating end sequences in the first and second homologous chromosomes. The end sequences in each of the first and second homologous chromosomes can then undergo a repair process mediated by an exogenous repair template to form a genome with a biallelic modification comprising the targeted genetic modification. For example, if the exogenous repair template comprises a nucleic acid insert, the nucleic acid insert can be inserted in the Fbn1 gene in the pair of first and second homologous chromosomes, thereby resulting in a homozygous modified genome.

Alternatively, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele). For example, in the allele without the targeted modification, a double-strand break created by the Cas protein may have been repaired by non-homologous end joining (NHEJ)-mediated DNA repair, which generates a mutant allele comprising an insertion or a deletion of a nucleic acid sequence and thereby causes disruption of that genomic locus. For example, a biallelic modification can result in compound heterozygosity if the cell has one allele with the targeted modification and another allele that is not capable of being expressed. Compound heterozygosity includes hemizygosity. Hemizygosity includes situations in which only one allele (i.e., an allele on one of two homologous chromosomes) of the target locus is present. For example, a biallelic modification can result in hemizygosity for a targeted modification if the targeted modification occurs in one allele with a corresponding loss or deletion of the other allele.

G. Identifying Cells with Targeted Genetic Modifications

The methods disclosed herein can further comprise identifying a cell having a modified Fbn1 gene. Various methods can be used to identify cells having a targeted genetic modification, such as a deletion or an insertion. Such methods can comprise identifying one cell having the targeted genetic modification in the Fbn1 gene. Screening can be done to identify such cells with modified genomic loci.

The screening step can comprise a quantitative assay for assessing modification of allele (MOA) (e.g., loss-of-allele (LOA) and/or gain-of-allele (GOA) assays) of a parental chromosome. For example, the quantitative assay can be carried out via a quantitative PCR, such as a real-time PCR (qPCR). The real-time PCR can utilize a first primer set that recognizes the target genomic locus and a second primer set that recognizes a non-targeted reference locus. The primer set can comprise a fluorescent probe that recognizes the amplified sequence.

The screening step can also comprise a retention assay, which is an assay used to distinguish between correct targeted insertions of a nucleic acid insert into a target genomic locus from random transgenic insertions of the nucleic acid insert into genomic locations outside of the target genomic locus. Conventional assays for screening for targeted modifications, such as long-range PCR or Southern blotting, link the inserted targeting vector to the targeted locus. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/0178879 and Frendewey et al. (2010) *Methods Enzymol.* 476:295-307, each of which is herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

Because paired gRNAs can create large Cas-mediated deletions at a target genomic locus, it can be useful augment standard LOA and GOA assays to verify correct targeting by LTVECs (i.e., in cells other than one-cell stage embryos). For example, LOA and GOA assays alone may not distinguish correctly targeted cell clones from clones in which a large Cas-induced deletion of the target genomic locus coincides with random integration of a LTVEC elsewhere in the genome, particularly if the GOA assay employs a probe against a selection cassette within the LTVEC insert. Because the selection pressure in the targeted cell is based on the selection cassette, random transgenic integration of the LTVEC elsewhere in the genome will generally include the selection cassette and adjacent regions of the LTVEC but will exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, generally the 3' homology arm but not the 5' homology arm will be transgenically integrated with the selection cassette. Alternatively, if the selection cassette adjacent to the 5' homology arm, generally the 5' homology arm but not the 3' homology arm will be transgenically integrated with the selection cassette. As an example, if LOA and GOA assays are used to assess targeted integration of the LTVEC, and the GOA assay utilizes probes against the selection cassette, a heterozygous deletion at the target genomic locus combined with a random transgenic integration of the LTVEC will give the same readout as a heterozygous targeted integration of the LTVEC at the target genomic locus. To verify correct targeting by the LTVEC, retention assays can be used, alone or in conjunction with LOA and/or GOA Assays.

Retention assays determine copy numbers of a DNA template in the 5' target sequence (corresponding to the 5' homology arm of the LTVEC) and/or the 3' target sequence (corresponding to the 3' homology arm of the LTVEC). In particular, determining the copy number of a DNA template in the target sequence corresponding to the homology arm that is adjacent to the selection cassette is useful. In diploid cells, copy numbers greater than two generally indicate transgenic integration of the LTVEC randomly outside of the target genomic locus rather than at the target genomic locus, which is undesirable. Correctly targeted clones will retain a copy number of two. In addition, copy numbers of less than two in such retention assays generally indicate large Cas-mediated deletions extending beyond the region targeted for deletion, which are also undesirable. See, e.g., US 2016/0145646 and WO 2016/081923, each of which is herein incorporated by reference in its entirety for all purposes.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening, particularly in one-cell stage embryos that have been modified. Next-generation sequencing can also be referred to as "NGS" or "massively parallel sequencing" or "high throughput sequencing." Such NGS can be used as a screening tool in addition to the MOA assays and retention assays to define the exact nature of the targeted genetic modification and to detect mosaicism. Mosaicism refers to the presence of two or more populations of cells with different genotypes in one individual who has developed from a single fertilized egg (i.e., zygote). In the methods disclosed herein, it is not necessary to screen for targeted clones using selection markers. For example, the MOA and NGS assays described herein can be relied on without using selection cassettes.

H. Methods of Making Genetically Modified Non-Human Animals

Genetically modified non-human animals can be generated employing the various methods disclosed herein. Any convenient method or protocol for producing a genetically modified organism, including the methods described herein, is suitable for producing such a genetically modified non-human animal. Such methods starting with genetically modifying a pluripotent cell such as an embryonic stem (ES) cell generally comprise: (1) modifying the genome of a pluripotent cell that is not a one-cell stage embryo using the methods described herein; (2) identifying or selecting the genetically modified pluripotent cell; (3) introducing the genetically modified pluripotent cell into a host embryo; and (4) implanting and gestating the host embryo comprising the genetically modified pluripotent cell in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be, for example, an ES cell (e.g., a rodent ES cell, a mouse ES cell, or a rat ES cell) as discussed elsewhere herein. See, e.g., U.S. Pat. No. 7,294,754, herein incorporated by reference in its entirety for all purposes.

Alternatively, such methods starting with genetically modifying a one-cell stage embryo generally comprise: (1) modifying the genome of a one-cell stage embryo using the methods described herein; (2) identifying or selecting the genetically modified embryo; and (3) implanting and gestating the genetically modified embryo in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of a non-human animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal that comprise the targeted genetic modification. It is recognized that depending on the method used to generate the F0 animal, the number of cells within the F0 animal that have the targeted genetic modification will vary. The introduction of the donor ES cells into a pre-morula stage embryo from a corresponding organism (e.g., an 8-cell stage mouse embryo) via, for example, the VELOCIMOUSE® method allows for a greater percentage of the cell population of the F0 animal to comprise cells having the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted genetic modification. In addition, at least one or more of the germ cells of the F0 animal can have the targeted genetic modification.

I. Types of Non-Human Animals and Cells

The methods provided herein employ non-human animals and cells and embryos from non-human animals. Such non-human animals are preferably mammals, such as rodents (e.g., rats, mice, and hamsters). Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). The term "non-human" excludes humans.

A non-human animal cell employed in the methods provided herein can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The non-human animal cells employed in the methods provided herein can also include one-cell stage embryos (i.e., fertilized oocytes or zygotes). Such one-cell stage embryos can be from any genetic background (e.g., BALB/c, C57BL/6, 129, or a combination thereof), can be fresh or frozen, and can be derived from natural breeding or in vitro fertilization.

Mice and mouse cells employed in the methods provided herein can be from any strain, including, for example, a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse or mouse cell employed in the methods provided herein can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice or mouse cells can have a strain comprising 50% BALB/c, 25% C57BL/6, and 25% 129. Alternatively, the mice or mouse cells can comprise a strain or strain combination that excludes BALB/c.

Examples of 129 strains and C57BL strains are disclosed elsewhere herein. Mice and mouse cells employed in the methods provided herein can also be from a mix of an aforementioned 129 strain and an aforementioned C57BL/6 strain (e.g., 50% 129 and 50% C57BL/6). Likewise, mice and mouse cells employed in the methods provided herein can be from a mix of aforementioned 129 strains or a mix of aforementioned BL/6 strains (e.g., the 129S6 (129/SvEvTac) strain). A specific example of a mouse ES cell is a VGF1 mouse ES cell. VGF1 mouse ES cells (also known as F1H4) were derived from hybrid embryos produced by crossing a female C57BL/6NTac mouse to a male 12956/SvEvTac mouse. See, e.g., Auerbach et al. (2000) *Biotechniques* 29, 1024-1028, herein incorporated by reference in its entirety for all purposes.

Rats or rat cells employed in the methods provided herein can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats or rat cells can also be obtained from a strain derived from a mix of two or more strains recited above. For example, the rat or rat cell can be from a DA strain or an ACI strain. The ACI rat strain is characterized as having black agouti, with white belly and feet and an $RT1^{avl}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{avl}$ haplotype. Such rats are available from a variety of sources including Charles River and Harlan Laboratories. Examples of rat ES cell lines from a DA rat are the DA.2B rat ES cell line and the DA.2C rat ES cell line. In some cases, the rats or rat cells are from an inbred rat strain. See, e.g., US 2014/0235933 A1, herein incorporated by reference in its entirety for all purposes.

Cells that have been implanted into a host embryo can be referred to as "donor cells." The donor cell can be from the same strain as the host embryo or from a different strain. Likewise, the surrogate mother can be from the same strain as the donor cell and/or the host embryo, or the surrogate mother can be from a different strain as the donor cell and/or the host embryo.

A variety of host embryos can be employed in the methods and compositions disclosed herein. For example, a donor cell (e.g., donor ES cell) can be introduced into a pre-morula stage embryo (e.g., an 8-cell stage embryo) from a corresponding organism. See, e.g., U.S. Pat. No. 7,576,259; 7,659,442; 7,294,754; and US 2008/0078000, each of which is herein incorporated by reference in its entirety for all purposes. In other methods, the donor cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo (e.g., an aggregated morula stage embryo), an uncompacted morula stage embryo, or a compacted morula stage embryo. When employing a mouse embryo, the host embryo stage can be a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York, herein incorporated by reference in its entirety for all purposes. For example, the Theiler Stage can be selected from TS1, TS2, TS3, and TS4. In some methods, the host embryo comprises a zona pellucida, and the donor cell is an ES cell that is introduced into the host embryo through a hole in the zona pellucida. In other methods, the host embryo is a zona-less embryo.

III. Methods of Screening Compounds

The non-human animals having the Fbn1 mutations described herein can be used for screening compounds for activity potentially useful in inhibiting or reducing neonatal progeroid syndrome with congenital lipodystrophy (NPSCL) or ameliorating NPSCL-like symptoms (e.g., congenital lipodystrophy-like symptoms) or screening compounds for activity potentially harmful in promoting or exacerbating NPSCL. Compounds having activity inhibiting or reducing NPSCL or ameliorating NPSCL-like symptoms are potentially useful as therapeutics or prophylactics against NPSCL. Compounds having activity promoting or exacerbating NPSCL are identified as toxic and should be avoided as therapeutics or in other circumstances in which they may come into contact with humans (e.g., in foods, agriculture, construction, or water supply).

Examples of compounds that can be screened include antibodies, antigen-binding proteins, site-specific DNA binding proteins (e.g., CRISPR-Cas complexes), polypeptides, beta-turn mimetics, polysaccharides, phospholipids, hormones, prostaglandins, steroids, aromatic compounds, heterocyclic compounds, benzodiazepines, oligomeric N-substituted glycines, and oligocarbamates. Large combinatorial libraries of the compounds can be constructed by the encoded synthetic libraries (ESL) method described in WO 1995/012608, WO 1993/006121, WO 1994/008051, WO 1995/035503, and WO 1995/030642, each of which is herein incorporated by reference in its entirety for all purposes. Peptide libraries can also be generated by phage display methods. See, e.g., U.S. Pat. No. 5,432,018, herein incorporated by reference in its entirety for all purposes. Use of libraries of guide RNAs for targeting CRISPR-Cas systems to different genes are disclosed, e.g., in WO 2014/204727, WO 2014/093701, WO 2015/065964, and WO 2016/011080, each of which is herein incorporated by reference in its entirety for all purposes.

Animal-based assays generally involve administering a compound to the Fbn1 mutant non-human animal and assessing symptoms closely resembling those of NPSCL in humans for change in response. The change can be assessed from levels of the symptom before and after contacting the non-human animal with the compound or by performing a control experiment performed with a control animal having the same Fbn1 mutation (e.g., wild type cohort sibling) without the compound.

Suitable NPSCL-like signs or symptoms that can be monitored include body weight, lean mass, fat mass, white adipose mass (e.g., normalized by body weight), body fat percentage, food intake normalized by body weight, and kyphosis, as disclosed elsewhere herein. For example, white adipose tissue mass (e.g., normalized by body weight) can be monitored. These symptoms can be monitored in combination with one or more of the following: glucose tolerance, serum cholesterol levels, serum triglyceride levels, and serum non-esterified fatty acid levels. Likewise, these symptoms can be monitored in combination with one or more of the following: glucose tolerance, serum cholesterol levels, serum triglyceride levels, serum non-esterified fatty acid levels, liver weight, brown adipose tissue (BAT) weight, visceral white adipose tissue (WAT) weight, WAT weight normalized to body weight, metabolic rate normalized to body weight, energy expenditure, and insulin sensitivity on high-fat diet. For example, exacerbation of such NPSCL-like symptoms can result in one or more of decreased body weight, decreased lean mass, decreased fat mass, decreased white adipose tissue (e.g., normalized by body weight), decreased body fat percentage, increased food intake normalized by body weight, and increased kyphosis compared to the levels of the symptoms before contacting with the compound or compared to the levels of symptoms in the control non-human animal. Such decreases or increases can occur with one or more of decreased liver weight, preserved brown adipose tissue (BAT) weight (e.g., normalized by body weight), decreased visceral white adipose tissue (WAT) weight, decreased WAT weight normalized to body weight, elevated metabolic rate normalized to body weight, increased energy expenditure, improved glucose tolerance, and improved insulin sensitivity on high-fat diet. Such decreases or increases can occur with one or more of the following remaining normal: glucose tolerance, serum cholesterol levels, serum triglyceride levels, and serum non-esterified fatty acid levels. Alternatively, amelioration of such NPSCL-like symptoms can result in one or more of increased body weight, increased lean mass, increased fat mass, increased body fat percentage, decreased food intake normalized by body weight, and decreased kyphosis compared to the levels of the symptoms before contacting with the compound or compared to the levels of symptoms in the control non-human animal. Such decreases or increases can occur with one or more of increased liver weight, preserved or altered brown adipose tissue (BAT) weight (e.g., normalized by body weight), increased visceral white adipose tissue (WAT) weight, increased WAT weight normalized to body weight, decreased metabolic rate normalized to body weight, decreased energy expenditure, decreased glucose tolerance, and decreased insulin sensitivity on high-fat diet. Such symptoms can be assayed as described in the examples provided herein. The decrease or increase can be statistically significant. For example, the decrease or increase can be by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100%.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
|---|---|---|
| 1 | DNA | Human WT FBN1 Nucleic Acid Fragment in FIG. 1 |
| 2 | Protein | Human WT FBN1 Protein Fragment in FIG. 1 |
| 3 | DNA | Human Variant FBN1 Fragment in FIG. 1 |
| 4 | Protein | Human Variant FBN1 Protein Fragment in FIG. 1 |
| 5 | DNA | Mouse WT Fbn1 Nucleic Acid Fragment from FIG. 1 |
| 6 | Protein | Mouse WT Fbn1 Protein Fragment from FIG. 1 |
| 7 | DNA | Mouse Fbn1 Variant MAID 8501 Nucleic Acid Fragment from FIG. 1 |
| 8 | Protein | Mouse Fbn1 Variant MAID 8501 Protein Fragment from FIG. 1 |
| 9 | DNA | Human WT FBN1 Nucleic Acid Fragment in FIG. 3 |
| 10 | Protein | Human WT FBN1 Protein Fragment in FIG. 3 |
| 11 | DNA | Human Variant FBN1 Nucleic Acid Fragment in FIG. 3 |
| 12 | Protein | Human Variant FBN1 Protein Fragment in FIG. 3 |

TABLE 1-continued

| Description of Sequences. | | |
|---|---|---|
| SEQ ID NO | Type | Description |
| 13 | DNA | Mouse WT Fbn1 Nucleic Acid Fragment from FIG. 3 |
| 14 | Protein | Mouse WT Fbn1 Protein Fragment from FIG. 3 |
| 15 | DNA | Mouse Fbn1 Variant MAID 8502 Nucleic Acid Fragment from FIG. 3 |
| 16 | Protein | Mouse Fbn1 Variant MAID 8502 Protein Fragment from FIG. 3 |
| 17 | Protein | Mouse Fbn1 Variant MAID 8520 Protein Fragment from FIG. 3 |
| 18 | Protein | Mouse Fbn1 Variant MAID 8502 Protein Fragment from FIG. 3 |
| 19 | DNA | Human WT FBN1 cDNA |
| 20 | DNA | Mouse WT Fbn1 cDNA |
| 21 | DNA | Mouse Fbn1 cDNA with MAID 8501 Mutations |
| 22 | DNA | Mouse Fbn1 cDNA with MAID 8520 Mutations |
| 23 | DNA | Mouse Fbn1 cDNA with MAID 8502 Mutations |
| 24 | DNA | Human WT Penultimate FBN1 Exon |
| 25 | DNA | Mouse WT Penultimate Fbn1 Exon |
| 26 | DNA | Mouse Penultimate Fbn1 Exon with MAID 8501 Mutations |
| 27 | DNA | Mouse Penultimate Fbn1 Exon with MAID 8520 Mutations |
| 28 | DNA | Mouse Penultimate Fbn1 Exon with MAID 8502 Mutations |
| 29 | Protein | Human WT FBN1 Protein |
| 30 | Protein | Mouse WT Fbn1 Protein |
| 31 | Protein | MAID 8501 Protein |
| 32 | Protein | MAID 8520 Protein |
| 33 | Protein | MAID 8502 Protein |
| 34 | Protein | Extremely Positively Charged C-Terminus |
| 35 | Protein | Less Positively Charged C-Terminus |
| 36 | Protein | Amino Acid Recognition Sequence for Furin Family Proteases |
| 37 | DNA | mGA for MAID 8501 |
| 38 | DNA | Donor for MAID 8501 |
| 39 | DNA | Generic Guide RNA Recognition Sequence v1 |
| 40 | DNA | Generic Guide RNA Recognition Sequence v2 |
| 41 | DNA | Generic Guide RNA Recognition Sequence v3 |
| 42 | Protein | C-terminus of MAID 8520 Protein |
| 43 | Protein | C-terminus of MAID 8502 Protein |
| 44 | DNA | Insertion in MAID 8520 Allele |
| 45 | Protein | Final 14 Amino Acids of Protein Encoded by MAID 8501 Allele |
| 46 | Protein | Final 14 Amino Acids of Protein Encoded by MAID 8502 Allele |
| 47 | Protein | Final 14 Amino Acids of Protein Encoded by MAID 8520 Allele |

EXAMPLES

Example 1

Generation of MAID 8501 Fbn1 Mutant Mice with Truncated C-Terminus

A mutant Fbn1 mouse allele was generated to recreate a human mutant FBN1 allele. Using NM_007993.2 as a reference sequence, the mutation is c.8213 8214delinsACT. This mutation, which was created by inserting an A between c.8212 and 8213 and making a G>T substitution at c.8214, results in a premature termination codon in the penultimate exon of Fbn1. The mutant allele is indicated as MAID 8501. See FIG. 1. The mutation is within the last 50 nucleotides of the penultimate exon and is predicted to escape mRNA nonsense-mediated decay (NMD), leading to expression of a mutant, truncated profibrillin protein.

To generate the mutant allele, CRISPR/Cas9 components were introduced into a C57BL/6 one-cell stage embryo via pronuclear injection or cytoplasmic mRNA piezo injections together with a donor template. The sequence of the guide RNA DNA-targeting sequence is set forth in SEQ ID NO: 37, and the sequence of the donor is set forth in SEQ ID NO: 38. NGS was used to screen for correctly targeted clones. The targeting results are set forth in Table 2.

TABLE 2

| Targeting results for MAID 8501. | | | | | | |
|---|---|---|---|---|---|---|
| Deliv- | | Concentration (ng/μL) | Monoallelic Mutation | | Biallelic Mutation | |
| ery | Cas9 | Cas9/sgRNA/Donor | NHEJ | HR | NHEJ | HR |
| PNI | Protein | 40/40/15 | 18% | 12% | 17% | 3% |
| CI | mRNA | 100/50/100 | 36% | 24% | 19% | 10% |

F0 founder mice were generated following microinjection of embryos into pseudopregnant female mice. As shown in FIG. 2, no male or female mice homozygous for the MAID 8501 Fbn1 mutation survived past 40 days, whereas male and female heterozygous mice survived much longer.

Example 2

Generation of MAID 8520 Fbn1 Mutant Mice with Truncated C-Terminus

In another experiment, a guide RNA sequence and donor sequence were designed to generate a mutant Fbn1 allele corresponding to the human c.8155_8156del Fbn1 allele, which has a deletion of two base pairs in coding exon 64 (the penultimate exon) causing a frameshift with a subsequent premature termination codon 17 codons downstream of p.Lys2719. The predicted mutant allele is indicated as MAID 8502. See FIG. 3.

To generate the mutant allele, CRISPR/Cas9 components were introduced into a C57BL/6 one-cell stage embryo via pronuclear injection or cytoplasmic mRNA piezo injections together with a donor template. One clone that was generated had the MAID 8520 mutant allele shown in FIG. 3 rather than the expected MAID 8502 allele. The MAID 8520 mutant allele also results in a premature termination of the encoded Fbn1 protein as shown in FIG. 3.

Figure 4:
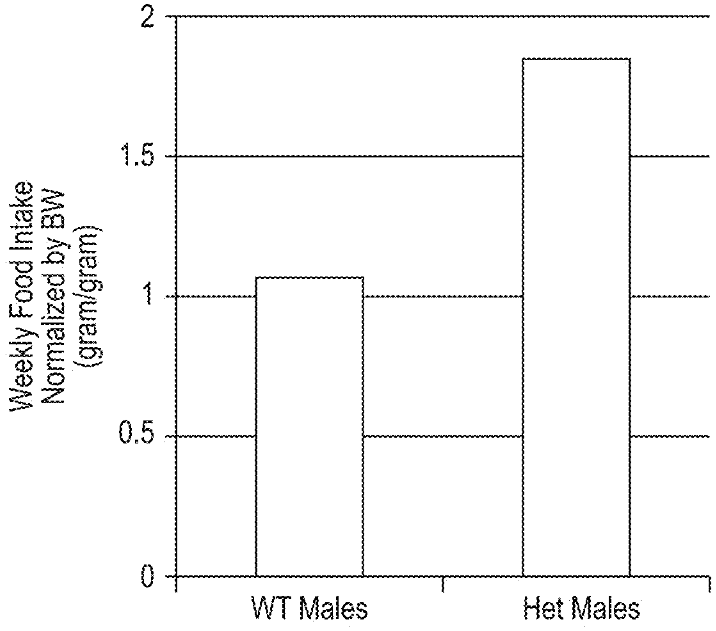
FIG. 4 shows the weekly food intake normalized by body weight for male wild type mice and F1 generation mice heterozygous for the engineered mouse Fbn1 gene variant MAID 8520.
Figure 5:
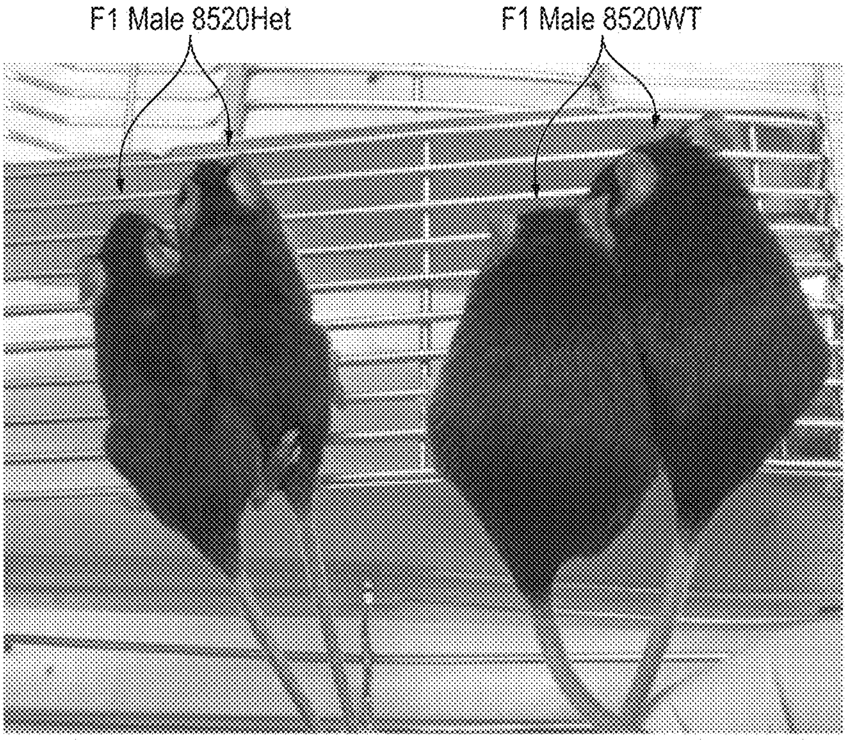
FIG. 5 shows 3-month old male F1 male wild type mice and 3-month old F1 male mice heterozygous for the engineered mouse Fbn1 gene variant MAID 8520.
Figure 6:
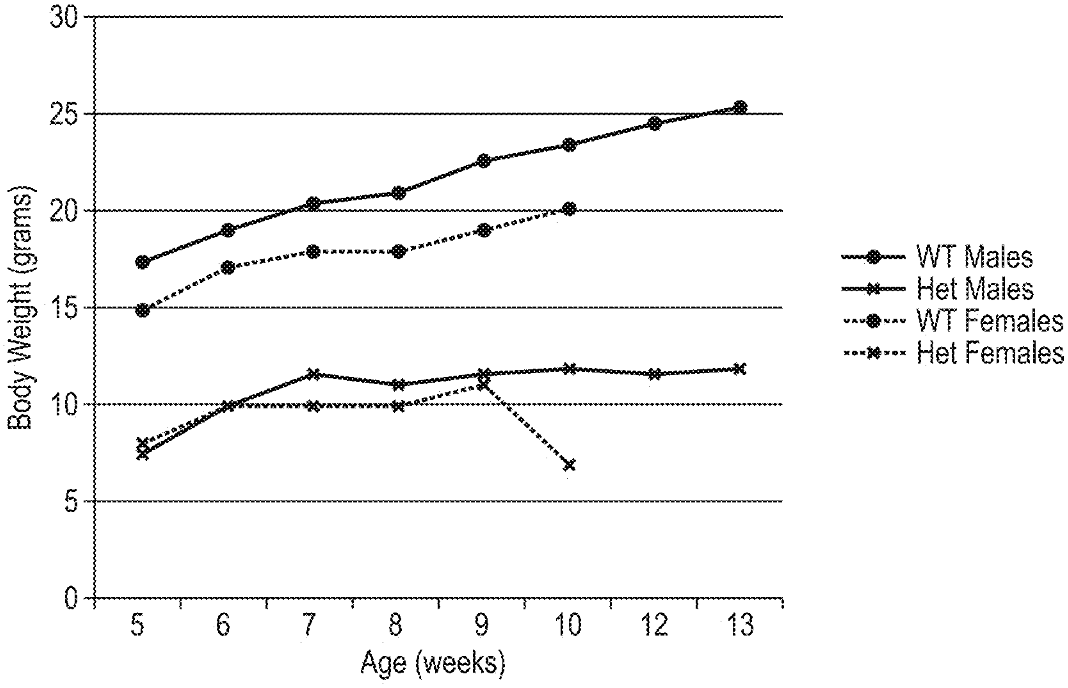
FIG. 6 shows the body weights of F1 mice by age, including wild type male mice, wild type female mice, and male and female mice heterozygous for the engineered mouse Fbn1 gene variant MAID 8520.
Figure 7E:
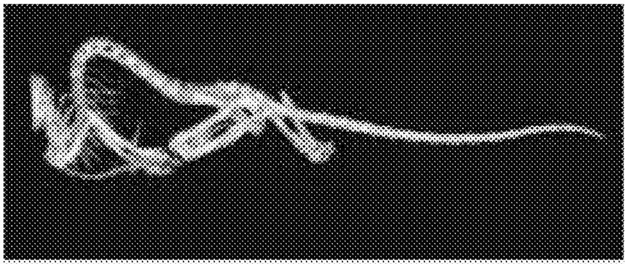
FIGS. 7A-7E show skeletons of wild type female mice (FIGS. 7A and 7B) and Fbn1 gene variant MAID 8520 heterozygous mice (FIGS. 7C-7E) showing uCT images of spinal kyphosis.
Figure 7D:
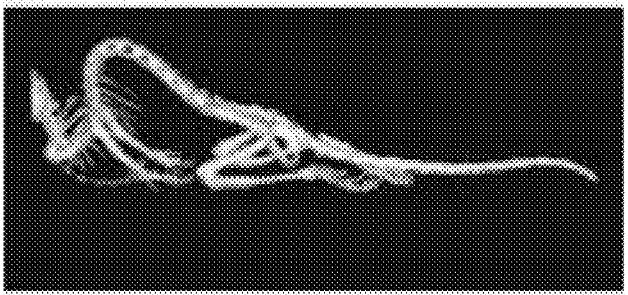
Figure 7C:
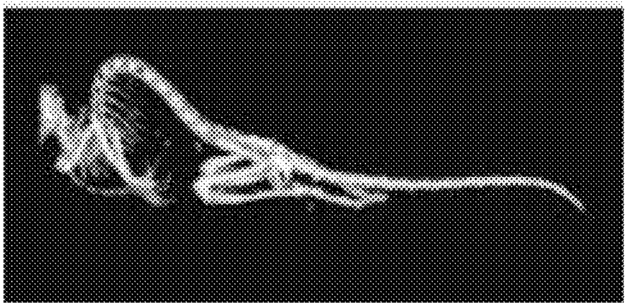
Figure 7B:
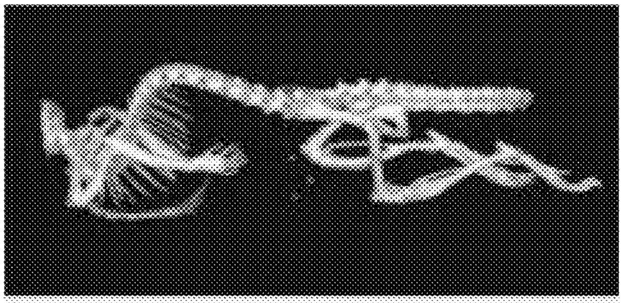
Figure 7A:
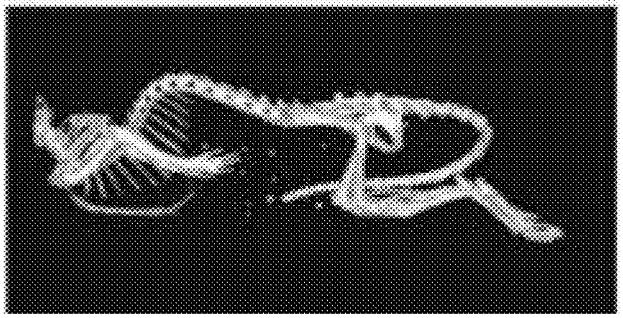

F0 founder mice were generated following microinjection of embryos into pseudopregnant female mice, and F1 generation mice were subsequently produced. Compared to wild type mice, the mice heterozygous for the Fbn1 mutation ate much more when normalized by body weight. See, e.g., FIG. 4, showing weekly food intake normalized by body weight (gram for gram), where heterozygous males ate approximately 1.7-fold more food than their wild type counterparts when normalized by body weight. Despite the increased food intake, the body weights of the male and female mice heterozygous for the Fbn1 mutation were consistently lower than the corresponding wild type mice over time. See, e.g., FIG. 5, showing two 3-month-old male F1 heterozygous mice on the left-hand side, and two 3-month-old wild type male F1 mice on the right-hand side. See also FIG. 6, showing the body weights of the F1 offspring from age 5 weeks to age 13 weeks. For example, whereas the body weights of the heterozygous mutant males were approximately 7 grams at 5 weeks and 12 grams at 13 weeks, the body weights of the corresponding wild type males were approximately 18 grams at 5 weeks and 25 grams at 13 weeks. These trends were also observed in the female mice.

Figure 8A:
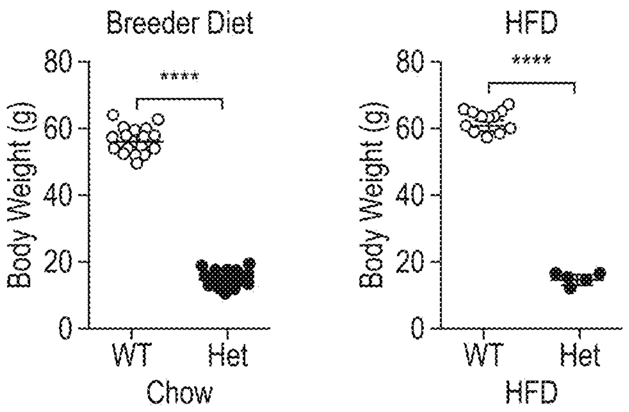
FIGS. 8A-8C show assays related to body weight and fat mass.
Figure 8B:
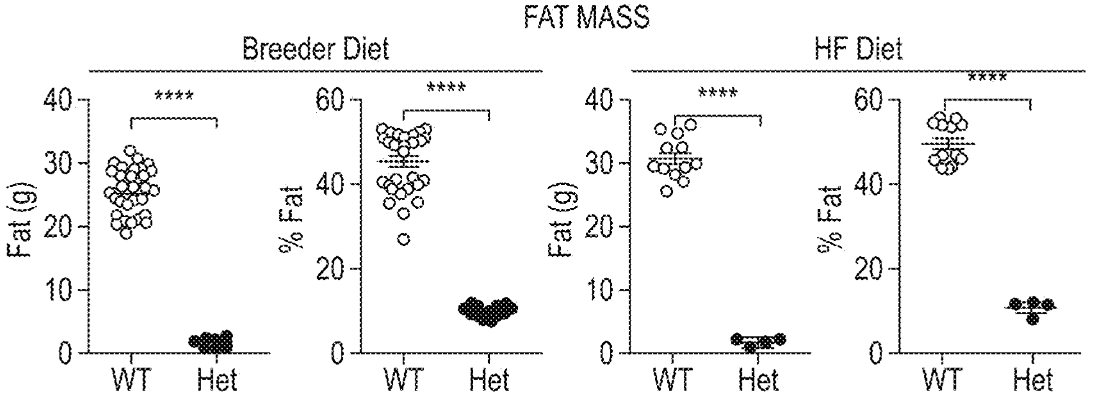
Figure 8C:
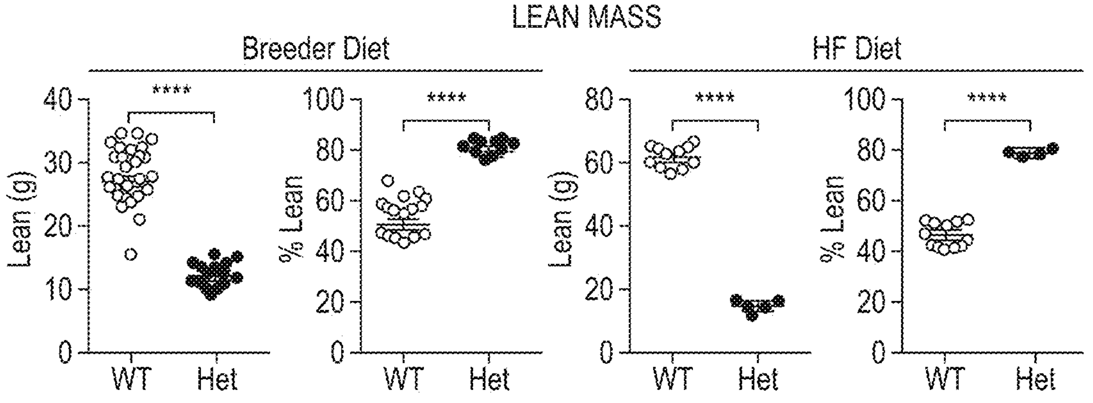
Figures 9A, 9B, 9C, 9D, 9E, 9F:
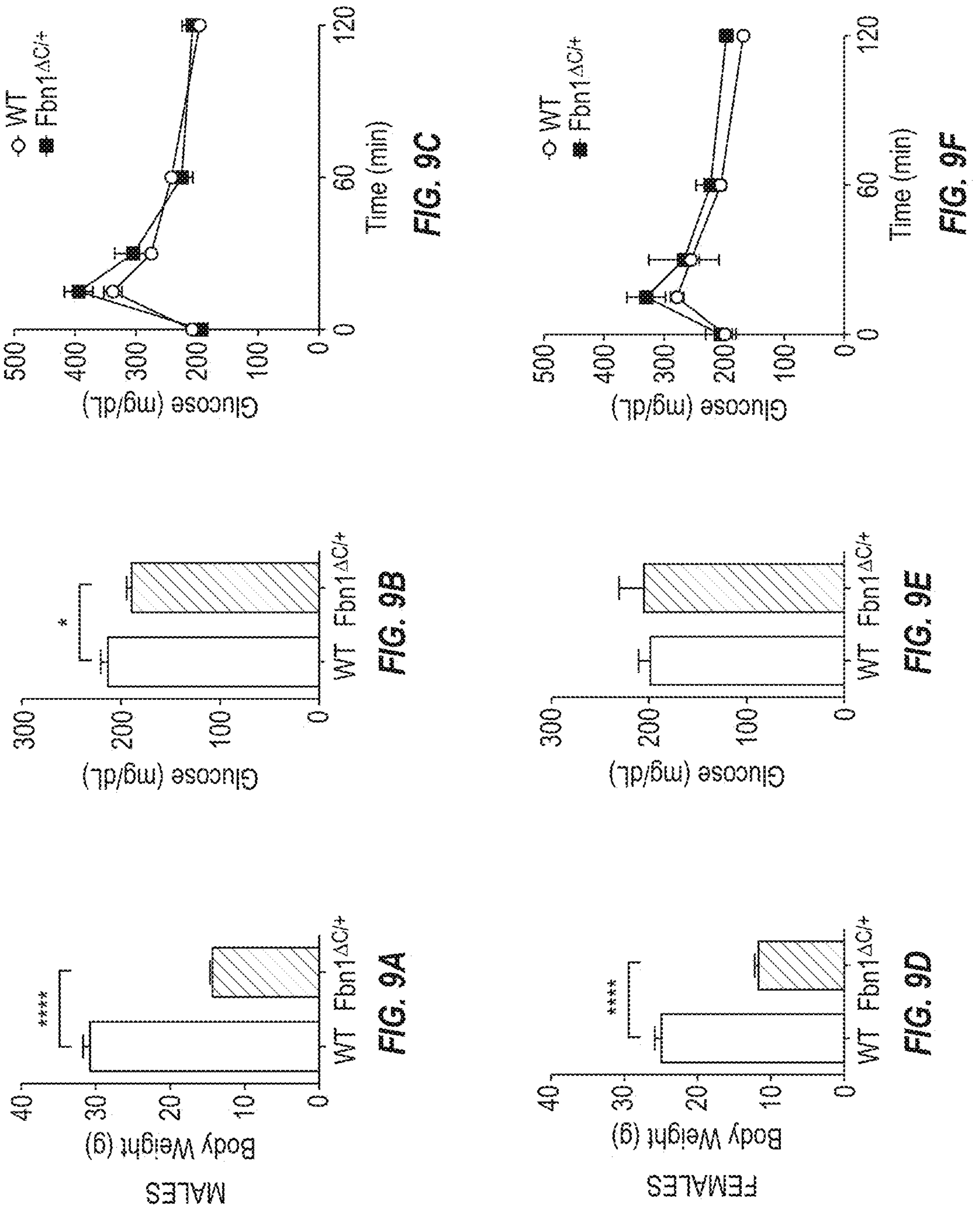
FIGS. 9A-9C show assays related to glucose homeostasis in male mice.
FIGS. 9D-9F show assays related to glucose homeostasis in female mice.
Figures 10A, 10B, 10C, 10D, 10E, 10F:
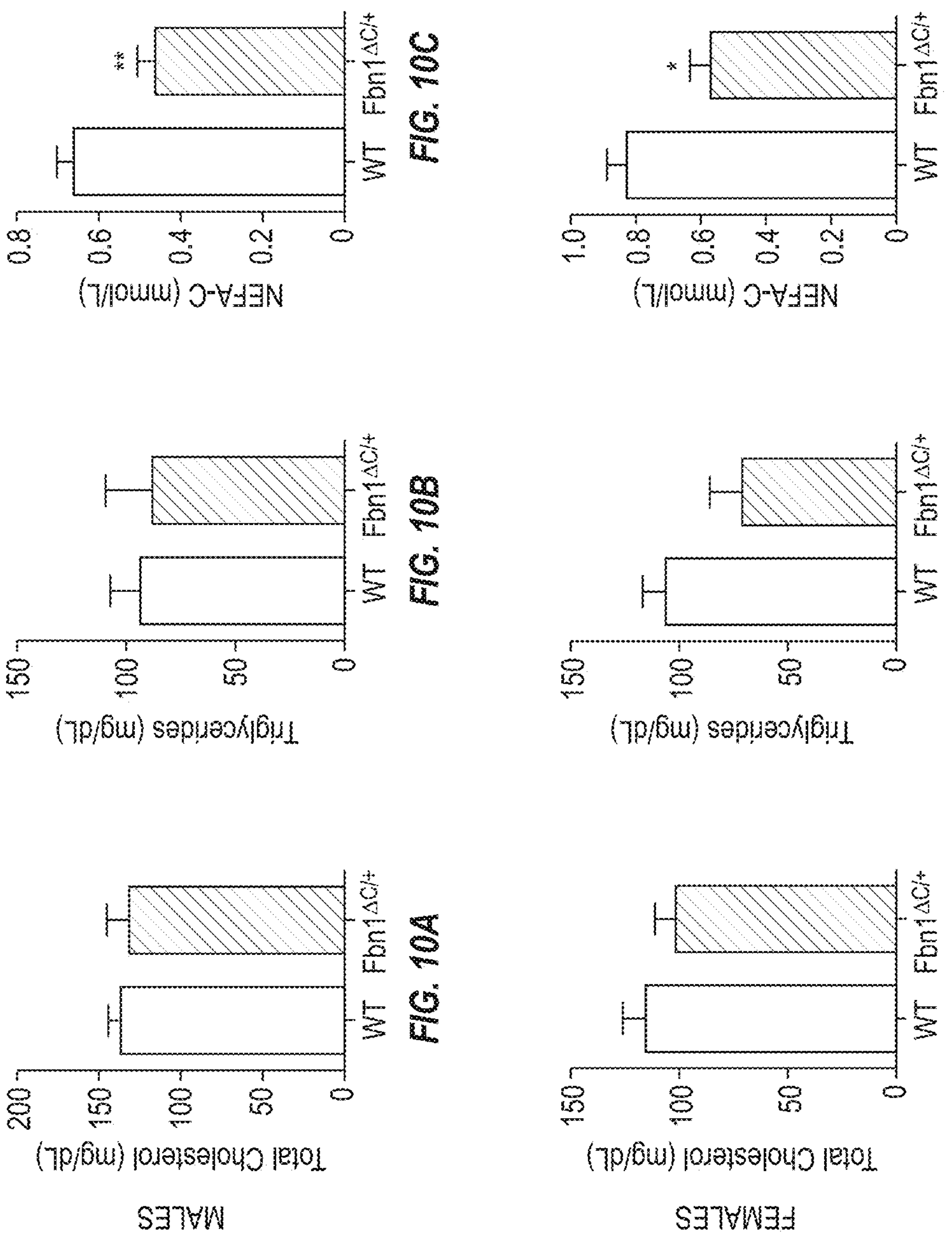
FIGS. 10A-10C show assays related to circulating lipids in male mice.
FIGS. 10D-10F show assays relating to circulating lipids in female mice.
Figure 11A:
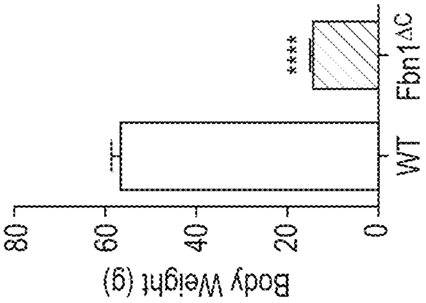
FIGS. 11A-11G show terminal liver and fat pad weights relative to body weights.
Figure 11B:
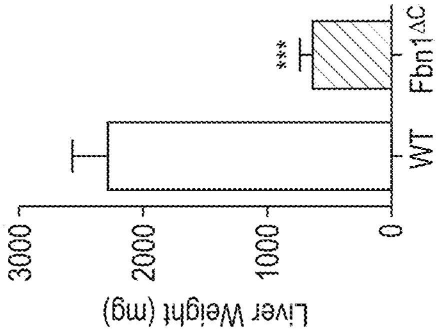
Figure 11C:
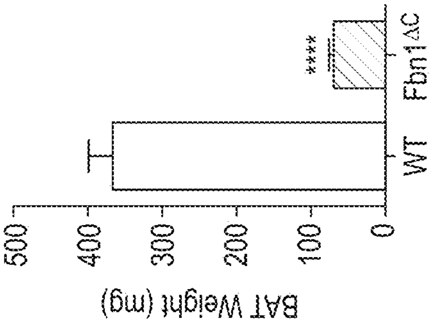
Figure 11D:
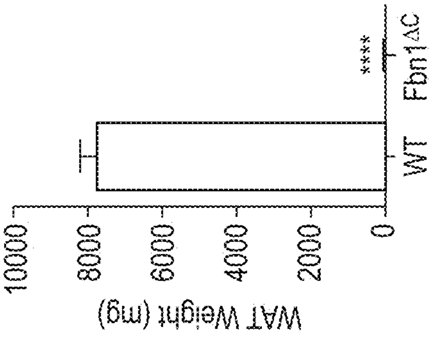
Figure 11E:
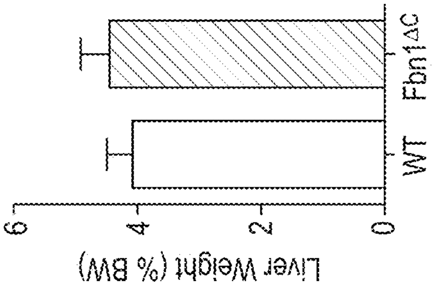
Figure 11F:
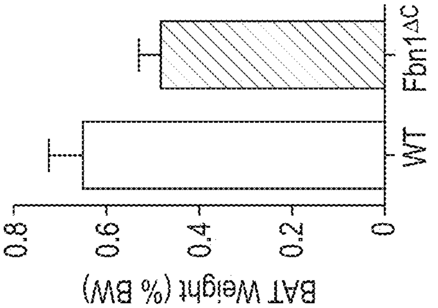
Figure 11G:
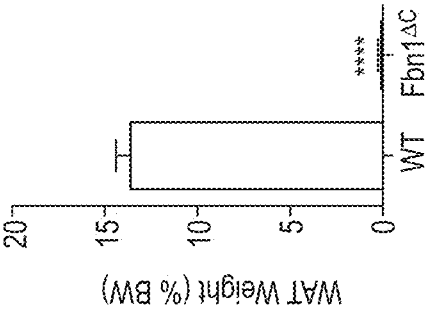
Figures 12A, 12B, 12C, 12D, 12E, 12F, 12G, 12H:
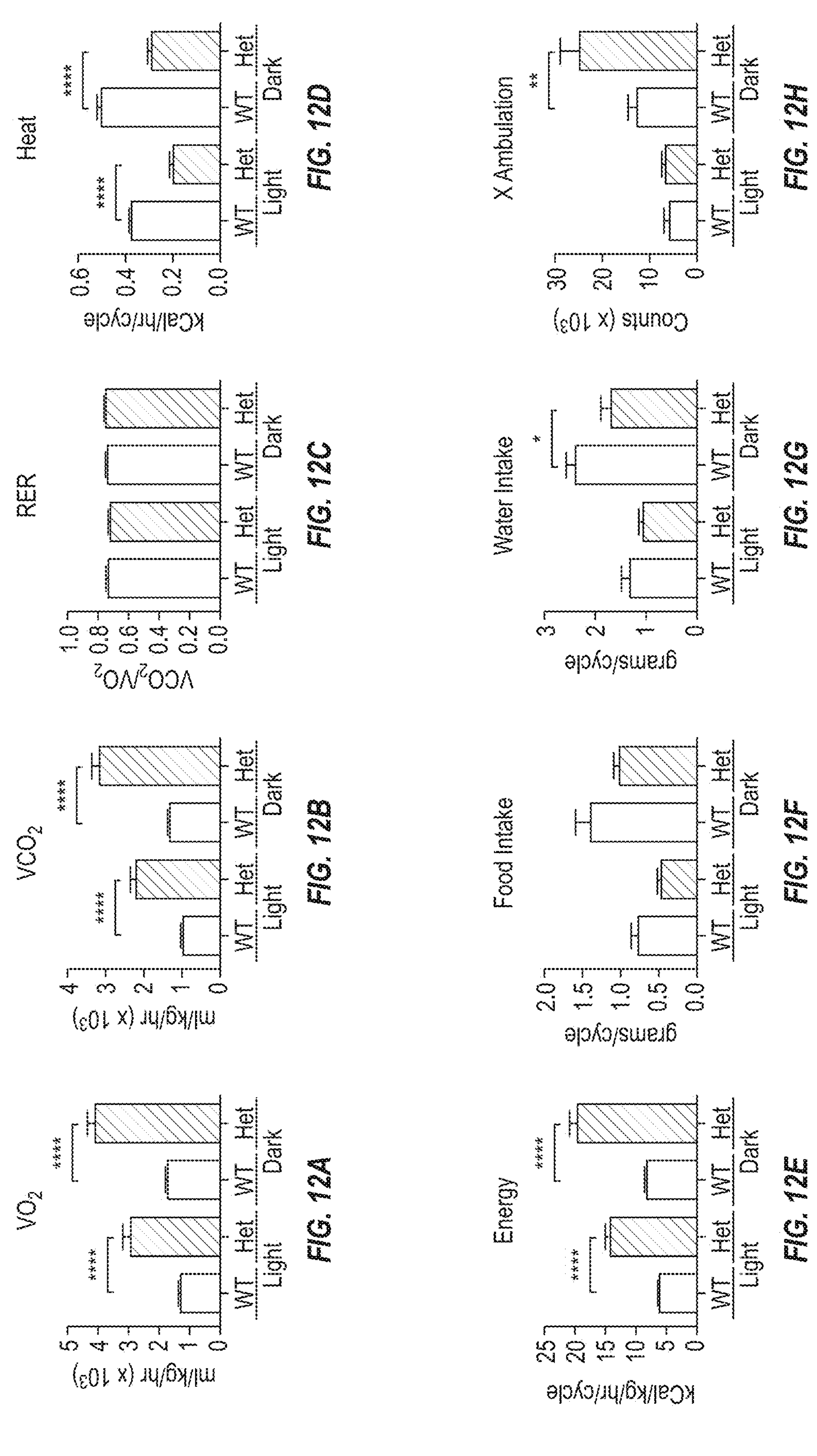
FIGS. 12A-12H show metabolic cage data from a Columbia Instruments Oxymax CLAMS system of female Fbn1 gene variant MAID 8520 heterozygous mice placed on a 60% high-fat diet for 12 weeks.
Figure 13A:
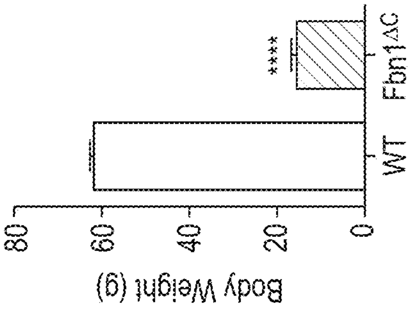
FIGS. 13A-13D show an insulin tolerance test of female Fbn1 gene variant MAID 8520 heterozygous mice placed on a 60% high-fat diet for 20 weeks.
Figure 13B:
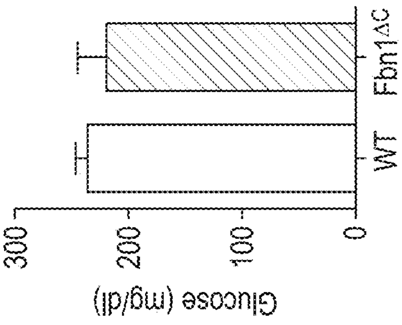
Figure 13C:
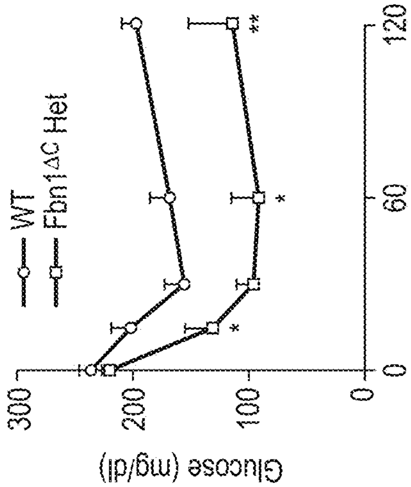
Figure 13D:
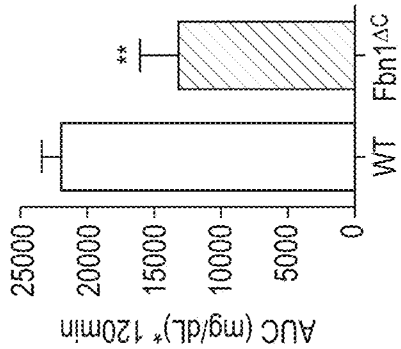

Further analysis of the heterozygous females compared to the wild type females showed kyphosis (i.e., exaggerated forward rounding of the back) in the heterozygous mutant females when compared to the wild type females. See FIGS. 7A-7E. Likewise, the heterozygous females had very little fat compared to their wild type counterparts. As shown in FIGS. 8A-8C, the heterozygous mutant female mice had statistically significant lower levels of body weight, lean mass, and fat mass as measured by ECHOMRI™, which is used to measure fat and lean mass in rodents. These differences held even if the mice were fed a 60% high-fat diet for 21 weeks. Despite the absence of body fat, heterozygous mutant females and corresponding wild type females showed similar glucose tolerance (oral glucose tolerance, given 2 mg/kg after an overnight fast) on a chow diet and no elevations in serum cholesterol, triglycerides, and non-esterified fatty acids (measured by ADVIA). See, e.g., FIGS. 9A-9F and 10A-10F, respectively.

Further analysis of the heterozygous mutant females showed preservation of the brown adipose tissue (BAT) depot despite near complete loss of the visceral white adipose. See FIGS. 11A-11H. The preservation of BAT led us to examine the energy expenditure of the heterozygous mutant females after 12 weeks of 60% high-fat diet feeding. See FIGS. 12A-12H. Metabolic cage analysis using a Columbia Instruments Oxymax CLAMS system showed the mice had an elevated metabolic rate normalized to body weight as indicated by their $VO_2$, $VCO_2$ and energy expenditure (Energy). After 20 weeks on a high-fat diet, these mice also exhibited improved glucose tolerance. See FIGS. 13A-13D.

The mice heterozygous for the C-terminal deletion in Fibrillin-1 are lean with great reduction of white fat depots, but they have preserved brown adipose, increased energy expenditure, similar glucose tolerance, improved insulin sensitivity on high-fat diet, and no elevation in serum lipids compared to wild type mice. This recapitulates the FBN1 phenotype observed in human NPSCL patients in that, unlike many lipodystrophic syndromes, these particular mice have a normal metabolic profile in terms of glucose homeostasis and circulating lipids despite having no visceral adipose tissue. Many other models of FBN1 mutant mice have grossly normal heterozygotes while the homozygotes have early postnatal or embryonic death. See, e.g., Pereira et al. (1999) *Proc. Natl. Acad. Sci. U.S.A.* 96(7):3819-3823, herein incorporated by reference in its entirety for all purposes. Our model shows a dominant heterozygous phenotype, which recapitulates many of the features of the human patients, allowing us to study therapeutic options. In particular, our model shows a loss of white adipose tissue while brown adipose tissue is preserved in combination with an improvement in insulin sensitivity despite the loss of white adipose tissue. Human NPSCL patients have normal glucose homeostasis despite loss of white adipose tissue, which our model reflects. Preservation of brown adipose tissue is likely the mechanism underlying the maintained/improved insulin sensitivity, as this may allow the mice to burn off the excess fat they are not able to store.

We claim:

1. An isolated mouse one-cell stage embryo whose genome comprises a mutation in the penultimate exon of the endogenous fibrillin-1 (Fbn1) gene, wherein the mutation results in disruption or ablation of the asprosin C-terminal cleavage product of pro-fibrillin-1, wherein expression of the mutant Fbn1 gene results in a C-terminally truncated Fbn1 protein, and wherein a mouse generated from the isolated mouse one-cell stage embryo exhibits decreased body weight, decreased lean mass, and decreased fat mass when compared to a wild-type mouse.

2. The isolated mouse one-cell stage embryo of claim 1, wherein the mutant Fbn1 gene is operably linked to the endogenous Fbn1 promoter.

3. The isolated mouse one-cell stage embryo of claim 1, wherein the mutation is a frameshift mutation.

4. The isolated mouse one-cell stage embryo of claim 1, wherein the mutation results in a premature termination codon, wherein the premature termination codon is in the penultimate or the final exon of the Fbn1 gene.

5. The isolated mouse one-cell stage embryo of claim 4, wherein the premature termination codon is in the final exon or is less than 55 base pairs upstream of the last exon-exon junction in the Fbn1 gene.

6. The isolated mouse one-cell stage embryo of claim 1, wherein the mutation disrupts a basic amino acid recognition sequence for proprotein convertases of the furin family, and wherein the mutation is within about 50 base pairs of the furin recognition sequence.

7. The isolated mouse one-cell stage embryo of claim 1, wherein the C-terminally truncated Fbn1 protein has a positively charged C-terminus.

8. The isolated mouse one-cell stage embryo of claim 1, wherein the C-terminally truncated Fbn1 protein is truncated at a position corresponding to a position between amino acids 2700 and 2790, between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the C-terminally truncated Fbn1 protein is aligned with SEQ ID NO: 30.

9. The isolated mouse one-cell stage embryo of claim 8, wherein:

(I) the C-terminally truncated Fbn1 protein is truncated such that the last amino acid is at a position corresponding to amino acid 2737, amino acid 2738, or amino acid 2755 in the wild type mouse Fbn1 protein set forth in SEQ ID NO: 30 when the C-terminally truncated Fbn1 protein is aligned with SEQ ID NO: 30;

(II) the C-terminally truncated Fbn1 protein is truncated such that the last amino acid is at a position corresponding to amino acid 2737 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 43 or 46;

(III) the C-terminally truncated Fbn1 protein is truncated such that the last amino acid is at a position corresponding to amino acid 2738 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 8 or 45; or (IV) the C-terminally truncated Fbn1 protein is truncated such that the last amino acid is at a position corresponding to amino acid 2755 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 42 or 47.

10. The isolated mouse one-cell stage embryo of claim 1, wherein the C-terminally truncated Fbn1 protein has a C-terminus consisting of the sequence set forth in SEQ ID NO: 8, 42, 43, 45, 46, or 47.

11. The isolated mouse one-cell stage embryo of claim 1, wherein mRNA expressed from the Fbn1 gene escapes mRNA nonsense-mediated decay.

12. The isolated mouse one-cell stage embryo of claim 1, wherein the mutated penultimate exon of the Fbn1 gene comprises the mutations in SEQ ID NO: 26, 27, or 28 relative to the wild type mouse Fbn1 penultimate exon sequence set forth in SEQ ID NO: 25.

13. The isolated mouse one-cell stage embryo of claim 1, wherein the C-terminally truncated Fbn1 protein consists of the sequence set forth in SEQ ID NO: 31, 32, or 33.

14. The isolated mouse one-cell stage embryo of claim 1, wherein the penultimate exon is exon 64, and the mutation comprises an insertion or deletion that causes a −1 frameshift and results in a premature termination codon at the 3' end of exon 64 or the 5' end of exon 65.

15. The isolated mouse one-cell stage embryo of claim 14, wherein:

(I) the mutation comprises an insertion in exon 64 that causes a −1 frameshift and results in a premature termination codon at the 5' end of exon 65;

(II) the mutation comprises an insertion or deletion in exon 64 that causes a −1 frameshift and results in a premature termination codon at the 3' end of exon 64; or (III) the C-terminally truncated Fbn1 protein has a positively charged C-terminus.

16. The isolated mouse one-cell stage embryo of claim 15, wherein:

(I) the insertion is between positions corresponding to positions 8179 and 8180 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is aligned with SEQ ID NO: 20;

(II) the mutation comprises an insertion between positions corresponding to positions 8209 and 8210 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is aligned with SEQ ID NO: 20; or (III) the mutation comprises a deletion starting at a position corresponding to position 8161 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is aligned with SEQ ID NO: 20.

17. The isolated mouse one-cell stage embryo of claim 1, wherein the mouse generated from the isolated mouse one-cell stage embryo exhibits one or more of the following: decreased white adipose tissue normalized by body weight, decreased white adipose tissue in combination with preserved brown adipose tissue normalized by body weight, decreased body fat percentage, increased food intake normalized by body weight, and increased kyphosis.

18. The isolated mouse one-cell stage embryo of claim 17, wherein the mouse generated from the isolated mouse one-cell stage embryo exhibits:

(I) one or more of the following: increased metabolic rate, improved insulin sensitivity, normal glucose tolerance, normal serum cholesterol levels, normal serum triglyceride levels, and normal serum non-esterified fatty acid levels; or (II) decreased white adipose tissue normalized by body weight and at least one of improved insulin sensitivity, normal glucose tolerance, normal serum cholesterol levels, normal serum triglyceride levels, and normal serum non-esterified fatty acid levels.

19. A method of making a mouse whose genome comprises a mutation in the penultimate exon of the fibrillin-1 (Fbn1) gene, the method comprising implanting and gestating the isolated mouse one-cell stage embryo of claim 1 in a surrogate mother, such that a genetically modified mouse is obtained whose genome comprises the mutation in the penultimate exon of the endogenous Fbn1 gene, wherein the mutation results in disruption or ablation of the asprosin C-terminal cleavage product of pro-fibrillin-1, wherein expression of the mutant Fbn1 gene results in a C-terminally truncated Fbn1 protein, and wherein the mouse exhibits decreased body weight, decreased lean mass, and decreased fat mass compared to a wild-type mouse.

20. The method of claim 19, further comprising introducing a Cas9 protein, a guide RNA, and a donor template into an isolated mouse one-cell stage embryo, such that the mouse one-cell stage embryo of claim 1 is obtained.

* * * * *